United States Patent
Pfister et al.

(10) Patent No.: US 9,914,760 B2
(45) Date of Patent: Mar. 13, 2018

(54) METHODS OF IDENTIFYING, ISOLATING AND USING ODORANT AND AROMA RECEPTORS

(71) Applicants: Patrick Pfister, New York, NY (US); Matthew E. Rogers, New York, NY (US); Khalid Jerod Parris, Brooklyn, NY (US)

(72) Inventors: Patrick Pfister, New York, NY (US); Matthew E. Rogers, New York, NY (US); Khalid Jerod Parris, Brooklyn, NY (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/318,641

(22) Filed: Jun. 28, 2014

(65) Prior Publication Data

US 2015/0005177 A1    Jan. 1, 2015

Related U.S. Application Data

(60) Provisional application No. 61/841,282, filed on Jun. 29, 2013, provisional application No. 61/921,664, filed on Dec. 30, 2013.

(51) Int. Cl.
| | | |
|---|---|---|
| *C12Q 1/68* | (2018.01) | |
| *C07K 14/705* | (2006.01) | |
| *G01N 33/50* | (2006.01) | |

(52) U.S. Cl.
CPC .......... *C07K 14/705* (2013.01); *C12Q 1/6809* (2013.01); *G01N 33/5058* (2013.01); *C12Q 2600/136* (2013.01); *G01N 2333/705* (2013.01); *G01N 2500/04* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 4,434,084 A | 2/1984 | Hicks et al. | |
| 5,891,646 A | 4/1999 | Barak et al. | |
| 6,492,143 B1 | 12/2002 | Reed et al. | |
| 6,818,747 B2 | 11/2004 | Yao et al. | |
| 7,041,457 B2 | 5/2006 | Yao et al. | |
| 7,138,242 B2 | 11/2006 | Reed et al. | |
| 7,291,485 B2 | 11/2007 | Yao et al. | |
| 7,351,814 B2 | 4/2008 | Reed et al. | |
| 7,374,878 B2 | 5/2008 | Stryer et al. | |
| 7,425,445 B2 | 9/2008 | Matsunami et al. | |
| 7,541,151 B2 | 6/2009 | Barak et al. | |
| 7,615,610 B2 | 11/2009 | Shenoy et al. | |
| 7,691,564 B2 | 4/2010 | Devreotes et al. | |
| 7,691,592 B2 | 4/2010 | Matsunami et al. | |
| 7,838,288 B2 | 11/2010 | Matsunami et al. | |
| 7,858,394 B2 | 12/2010 | Wunder | |
| 7,879,565 B2 | 2/2011 | Matsunami et al. | |
| 7,981,602 B2 | 7/2011 | Mastroianni et al. | |
| 8,298,781 B2 | 10/2012 | Matsunami et al. | |
| 8,637,259 B1 | 1/2014 | Chatelain et al. | |
| 8,993,526 B2 | 3/2015 | Chatelain et al. | |
| 9,012,153 B2 | 4/2015 | Kumihashi et al. | |
| 9,068,226 B2 | 6/2015 | Matsunami et al. | |
| 9,233,082 B2 | 1/2016 | Kato et al. | |
| 9,249,453 B2 * | 2/2016 | Kato ................. | G01N 33/5058 |
| 9,284,575 B2 | 3/2016 | Marengo et al. | |
| 9,526,680 B2 | 12/2016 | Kato et al. | |
| 2003/0207337 A1 | 11/2003 | Han et al. | |
| 2007/0003980 A1 | 1/2007 | Woods et al. | |
| 2010/0248390 A1 | 9/2010 | Matsunami et al. | |

FOREIGN PATENT DOCUMENTS

| | | |
|---|---|---|
| WO | WO/2001/68805 A2 | 9/2001 |
| WO | WO2002/055557 A2 | 7/2002 |
| WO | WO2014/210585 A2 | 12/2014 |

OTHER PUBLICATIONS

Young et al., Genome Biology, vol. 4 (2003) pp. R71.1-R71.15.*
NCBI reference sequence, NP_666878, dated Sep. 1, 2013.*
International Search Report, application PCT/US2014/044770, dated Feb. 2, 2015.
Van Brunt A. et al., "Mus musculus BAC clone RP23-367E13 from 14 complete sequence," NCBI Accession No. AC133958, Sep. 22, 2002.
Church et al., PLOS Biology, vol. 7, No. 5, May 26, 2009, e100112, pp. 1-16.
Metzker, "Sequencing Technologies-the next generation," Nature Reviews Genetics, vol. 11, No. 1, Jan. 1, 2010, pp. 31-46.
Young et al., Genome Biology, Biomed Central Ltd, vol. 4, No. 11, Oct. 7, 2003, p. R71.1-R71.15.
Anonymous, "Human GPCR Polynucleotide SEQ ID No. 203," Accession No. GSN:ABZ42971, Mar. 6, 2003.
Anonymous, "Olfactory receptor family 52 subfamily N member 2 (OR 52N2), MCR cDNA," Accession No. GSN:AJF46831, Nov. 1, 2007.
Anonymous, "Olfactory receptor family 52 subfamily N member 2 (OR52N2) MCR protein," Accession No. GSP:AJF47196, Nov. 1, 2007.
Anonymous, "Human GPCRX cDNA #12," Accession No. GSN:ABQ88054, Sep. 18, 2002.

(Continued)

*Primary Examiner* — James S Ketter

(57) ABSTRACT

Provided here are new methods to identify specific families of mammalian odorant receptors for odorants or aroma, particularly indole and skatole malodors and their use in assays that may be used to discover compounds that modulate (blocking, enhancing, masking or mimicking compounds) their activity. Orphan mouse odorant receptors are identified from olfactory sensory neurons that respond to target compounds. The resulting receptors as well as their human counterparts can be screened in assays against test compounds to confirm their identity as odorant or aroma receptors, particularly malodor receptors and subsequently discover for example modulators that inhibit the perception of the malodor in humans.

4 Claims, 8 Drawing Sheets

(56) References Cited

OTHER PUBLICATIONS

Anonymous, "Human G protein coupled receptor X (GPCRX) protein SEQ ID No. 23," Accession No. GSN:ADC79337, Jan. 1, 2004.
Anonymous: "Sequence 1482 from Patent WO0127158," Accession No. EPOP:AX242734, Sep. 26, 2001.
Anonymous: Accession No. EM_STD:BC153189, Sep. 14, 2007.
Anonymous: "Odorant receptor identification related protein, SEQ ID No. 671," Accession No. GSP:AYJ84827, Nov. 25, 2010.
Anonymous: Accession No. UNIPROT:Q9NZP5, Oct. 10, 2003.
Kazushige Touhara, "Deorphanizing vertebrate olfactory receptors: Recent advances in odorant-response assays," Neurochemistry International, 51 (2007) 132-139.
Saito, et al, "Odor Coding by a Mammalian Receptor Repertoire," Sci Signal. Author manuscript; available in PMC Nov. 6, 2009.
Peterlin, et al, "The state of the art of odorant receptor deorphanization: a report from the orphanage," J. Gen. Physiol. (2014) vol. 143 No. 5 527-542.
Min Lu, et al, "Endoplasmic reticulum degradation impedes olfactory G-protein coupled receptor functional expression," BMC Cell Biology 2004, 5:34 doi:10.1186/1471-2121-5-34.
Adipietro, et al, "Functional Evolution of Odorant Receptors," PLoS Genetics Jul. 2012 vol. 8 Issue 7 e1002821.
Araneda, et al, "A pharmacological profile of the aldehyde receptor repertoire in rat olfactory epithelium," The Physiological Society 2004 J Physiol 555.3 (2004) pp. 743-756.
International Preliminary Report on Patentability for PCT/US2014/044770, dated Jan. 13, 2016.
Korean Office Action dated May 30, 2017 issued in corresponding Korean Application No. 10-2011-0027011 (English translation provided).

* cited by examiner

A

B

C

| | Olfr738 (SEQ ID NO: 30) | Olfr739 (SEQ ID NO: 32) | Olfr740 (SEQ ID NO: 2) | Olfr741 (SEQ ID NO: 4) | Olfr742 (SEQ ID NO: 34) | Olfr743 (SEQ ID NO: 6) | Olfr744 (SEQ ID NO: 36) | Olfr736 (SEQ ID NO: 28) | Olfr745 (SEQ ID NO: 8) | Olfr746 (SEQ ID NO: 38) | Olfr747 (SEQ ID NO: 40) | Olfr748 (SEQ ID NO: 42) | Olfr749 (SEQ ID NO: 44) | OR11G2 (SEQ ID NO: 14) | OR11H1 (SEQ ID NO: 46) | OR11H2 (SEQ ID NO: 48) | OR11H4 (SEQ ID NO: 50) | OR11H6 (SEQ ID NO: 16) | OR11H7 (SEQ ID NO: 52) | OR11H12 (SEQ ID NO: 54) |
|---|---|---|---|---|---|---|---|---|---|---|---|---|---|---|---|---|---|---|---|---|
| Olfr738 (SEQ ID NO: 30) | 100.0% | 83.3% | 83.9% | 81.3% | 82.9% | 80.7% | 81.4% | 62.1% | 60.9% | 59.1% | 61.3% | 58.5% | 62.2% | 78.1% | 57.0% | 59.3% | 59.5% | 58.4% | 58.8% | 57.6% |
| Olfr739 (SEQ ID NO: 32) | | 100.0% | 90.3% | 87.1% | 90.3% | 89.0% | 79.8% | 62.1% | 61.5% | 57.2% | 61.9% | 57.5% | 61.9% | 74.2% | 57.0% | 59.0% | 57.7% | 58.1% | 56.6% | 57.6% |
| Olfr740 (SEQ ID NO: 2) | | | 100.0% | 86.1% | 89.3% | 87.7% | 81.1% | 62.7% | 60.3% | 58.8% | 62.2% | 58.8% | 62.2% | 76.2% | 57.6% | 59.6% | 58.3% | 58.4% | 58.1% | 58.2% |
| Olfr741 (SEQ ID NO: 4) | | | | 100.0% | 94.2% | 80.9% | 78.3% | 60.1% | 57.9% | 55.6% | 59.1% | 56.2% | 59.1% | 72.9% | 53.9% | 55.8% | 54.9% | 56.3% | 55.9% | 54.2% |
| Olfr742 (SEQ ID NO: 34) | | | | | 100.0% | 83.5% | 79.8% | 60.8% | 59.4% | 57.5% | 60.6% | 58.1% | 61.0% | 73.6% | 55.5% | 57.4% | 56.7% | 57.8% | 57.2% | 56.1% |
| Olfr743 (SEQ ID NO: 6) | | | | | | 100.0% | 78.9% | 61.4% | 60.0% | 57.8% | 61.9% | 58.8% | 61.6% | 74.9% | 55.8% | 57.7% | 56.7% | 58.1% | 56.6% | 56.4% |
| Olfr744 (SEQ ID NO: 36) | | | | | | | 100.0% | 58.1% | 57.9% | 58.8% | 60.3% | 57.5% | 60.9% | 77.7% | 55.0% | 57.2% | 57.7% | 56.3% | 57.5% | 55.6% |
| Olfr736 (SEQ ID NO: 28) | | | | | | | | 100.0% | 60.0% | 57.8% | 59.1% | 58.0% | 59.4% | 60.8% | 58.2% | 60.8% | 59.8% | 59.6% | 58.4% | 58.8% |
| Olfr745 (SEQ ID NO: 8) | | | | | | | | | 100.0% | 60.6% | 63.6% | 59.4% | 64.8% | 57.9% | 60.6% | 60.9% | 64.5% | 81.5% | 58.4% | 60.9% |
| Olfr746 (SEQ ID NO: 38) | | | | | | | | | | 100.0% | 65.9% | 92.0% | 66.8% | 60.0% | 54.1% | 56.6% | 65.7% | 59.0% | 79.2% | 54.7% |
| Olfr747 (SEQ ID NO: 40) | | | | | | | | | | | 100.0% | 64.3% | 67.1% | 60.3% | 58.0% | 60.3% | 62.7% | 62.6% | 67.5% | 58.3% |
| Olfr748 (SEQ ID NO: 42) | | | | | | | | | | | | 100.0% | 65.6% | 60.3% | 53.3% | 55.8% | 64.1% | 58.1% | 78.3% | 53.9% |
| Olfr749 (SEQ ID NO: 44) | | | | | | | | | | | | | 100.0% | 61.0% | 57.4% | 60.0% | 83.6% | 64.1% | 68.1% | 58.0% |
| OR11G2 (SEQ ID NO: 14) | | | | | | | | | | | | | | 100.0% | 57.0% | 59.0% | 57.4% | 57.2% | 57.5% | 57.6% |
| OR11H1 (SEQ ID NO: 46) | | | | | | | | | | | | | | | 100.0% | 85.0% | 57.7% | 60.6% | 53.1% | 98.7% |
| OR11H2 (SEQ ID NO: 48) | | | | | | | | | | | | | | | | 100.0% | 59.5% | 60.9% | 55.6% | 94.4% |
| OR11H4 (SEQ ID NO: 50) | | | | | | | | | | | | | | | | | 100.0% | 62.6% | 66.3% | 58.3% |
| OR11H6 (SEQ ID NO: 16) | | | | | | | | | | | | | | | | | | 100.0% | 58.4% | 60.9% |
| OR11H7 (SEQ ID NO: 52) | | | | | | | | | | | | | | | | | | | 100.0% | 53.7% |
| OR11H12 (SEQ ID NO: 54) | | | | | | | | | | | | | | | | | | | | 100.0% |

Figure 8

| | Olfr665 (SEQ ID NO: 10) | Olfr666 (SEQ ID NO: 56) | Olfr667 (SEQ ID NO: 58) | Olfr668 (SEQ ID NO: 60) | Olfr669 (SEQ ID NO: 62) | Olfr658 (SEQ ID NO: 64) | Olfr659 (SEQ ID NO: 66) | Olfr503 (SEQ ID NO: 68) | OR52N1 (SEQ ID NO: 70) | OR52N4 (SEQ ID NO: 72) | OR52N5 (SEQ ID NO: 74) | OR52N2 (SEQ ID NO: 12) |
|---|---|---|---|---|---|---|---|---|---|---|---|---|
| Olfr665 (SEQ ID NO: 10) | 100.0% | 77.0% | 72.0% | 75.4% | 70.0% | 68.7% | 65.2% | 65.9% | 66.8% | 65.7% | 54.6% | 75.0% |
| Olfr666 (SEQ ID NO: 56) | | 100.0% | 84.0% | 97.4% | 75.1% | 74.6% | 69.2% | 69.3% | 74.6% | 73.8% | 60.3% | 88.4% |
| Olfr667 (SEQ ID NO: 58) | | | 100.0% | 82.8% | 69.3% | 70.1% | 66.3% | 65.5% | 71.1% | 69.3% | 55.5% | 79.1% |
| Olfr668 (SEQ ID NO: 60) | | | | 100.0% | 74.2% | 73.0% | 68.3% | 67.8% | 74.0% | 72.2% | 60.9% | 87.5% |
| Olfr669 (SEQ ID NO: 62) | | | | | 100.0% | 72.4% | 69.8% | 69.6% | 70.9% | 70.4% | 71.2% | 73.8% |
| Olfr658 (SEQ ID NO: 64) | | | | | | 100.0% | 82.7% | 93.4% | 73.3% | 87.3% | 58.5% | 72.4% |
| Olfr659 (SEQ ID NO: 66) | | | | | | | 100.0% | 79.6% | 67.0% | 79.5% | 54.7% | 68.0% |
| Olfr503 (SEQ ID NO: 68) | | | | | | | | 100.0% | 69.9% | 82.6% | 55.4% | 68.1% |
| OR52N1 (SEQ ID NO: 70) | | | | | | | | | 100.0% | 71.9% | 56.2% | 74.4% |
| OR52N4 (SEQ ID NO: 72) | | | | | | | | | | 100.0% | 56.0% | 71.6% |
| OR52N5 (SEQ ID NO: 74) | | | | | | | | | | | 100.0% | 59.7% |
| OR52N2 (SEQ ID NO: 12) | | | | | | | | | | | | 100.0% |

Figure 9

METHODS OF IDENTIFYING, ISOLATING AND USING ODORANT AND AROMA RECEPTORS

FIELD

The technical field is directed to odorant and aroma receptors and assays that can be used to identify odorant and/or aroma compounds and more specifically inhibitors or counteractants of malodor compounds such as indole, or skatole.

BACKGROUND

Olfaction is one of the most complex and poorly understood of human sensory systems. From olfactory receptor (OR) activation to perception, there are many steps that still require further investigation. If we can understand how the OR code for individual odorants and mixtures translates into perception then we can exploit this knowledge to bring significant benefit in several areas. These areas include odor modulators like malodor counteractants that block the perception of unpleasant odors, new flavor and fragrance ingredients that replace non-biodegradable or toxic compounds, and odor enhancers that would limit our reliance on difficult to source compounds from natural sources. The 'olfactory code' combinatorial paradigm is centered on the observation that any single OR may be activated by multiple odorants, and conversely most odorants are capable of activating several ORs. In the mouse genome there are ~1,200 distinct ORs. Humans, by contrast, have ~400. In both cases, the repertoire of ORs is activated by many thousands of odorants in the world, and it is this combinatorial complexity that allows for the breadth of olfactory sensations we can perceive. However, odorants or ligands for only 95 mouse (~8%) and 41 human ORs (~10%) have been identified as of 2014 using traditional deorphanization methods. In addition, the physiological relevance of most ligands for the human ORs, essentially identified in vitro, has not been tested.

Different OR de-orphanization methods have been described in the literature [e.g. Touhara (2007) Deorphanizing vertebrate olfactory receptors: Recent advances in odorant-response assays Neurochem Int 51, 132-139, Saito et al (2009) Odor coding by a Mammalian receptor repertoire. Sci Signal 2, ra9, and Peterlin et al. (2014), The State of the Art of Odorant Receptor Deorphanization: a Report from the Orphanage, J Gen Physiol; 143(5): 527-42]. Many of these methods rely exclusively on cell-based assays where the OR is expressed in non-olfactory cells that are suitable for high-throughput screening. However, ORs are often retained in the endoplasmic reticulum of such heterologous cells. Failing to traffic to the cell surface, the ORs are thus unable to interact with the odorant [Min et al. (2004) Endoplasmic reticulum degradation impedes olfactory G-protein coupled receptor functional expression. BMC Cell Biol 5, 34]. Thus, a systematic approach where hundreds to thousands of different cell lines, where each cell line possess a unique OR protein that can be assessed for odorant activity, is not a suitable approach for comprehensive decoding of the combinatoral interactions between odorants and ORs since many or most of the receptors do not function properly in such cell lines. There is therefore a need for new methods that can rapidly and reliably identify the relatively small subset of ORs, within the entire repertoire of ORs that exist in an organism, that are specifically activated or inhibited by one or more odorants. There is a further need for a method to involve the identification of ORs from the olfactory neurons themselves, where the ORs are presumed to be fully functional, thus circumventing the well-known challenges of OR assays in non-olfactory cells.

Malodor compounds such as indole, skatole (3-methyl indole), and p-cresol generate unpleasant odors that arise for example from latrines and other "bathroom" sources that contain fecal matter. Hence, malodor counteractants that mask or reduce the perceived intensity or modify the perceived quality for example of human smell of the compounds are desirable. Odorant receptors and more particularly malodor receptors have a need to be identified. Receptors that bind to indole and skatole have also been identified and compounds that bind to those receptors have been discovered and reported as potential modulators of malodor. However, the rapid identification of the complete repertoire of receptors that bind to malodors, particularly indole or skatole receptors continues to be desirable due to the numerous ORs that exist in mammals. Assays that rely on new malodor receptors to identify new potent compounds that bind to these receptors are further desired.

SUMMARY

Provided herein is a method of identifying olfactory receptors that are activated by an odorant or aroma compound comprising:
  a) dissociating an isolated olfactory epithelium containing native olfactory neurons into single cells from a non-human mammal species wherein each neuron expresses an olfactory receptor;
  b) loading the olfactory cells with an indicator dye that allows for the measurement of odorant or aroma receptor binding activity of the olfactory receptors;
  c) contacting the olfactory receptors with odorant or aroma compounds sequentially;
  d) measuring changes of odorant or aroma-induced neuronal activity;
  e) isolating one or more olfactory neurons that were activated by a odorant or aroma compound;
  f) isolating or isolating and amplifying the mRNA of the isolated olfactory receptors;
  g) sequencing at least a portion of the transcriptome of the mRNA by Next-Generation Sequencing; and
  h) determining the identity of a group of olfactory receptors selected from the group consisting of odorant and aroma receptors by comparing the sequence of the transcriptome to a reference genome sequence of the same species and other vertebrate species.

Further provided herein is a method of identifying olfactory receptors that are activated by a malodor compound comprising:
  a) dissociating an isolated olfactory epithelium containing native olfactory neurons into single cells from a non-human mammal species wherein each neuron expresses an olfactory receptor;
  b) loading the olfactory cells with an indicator dye that allows for the measurement of malodor receptor binding activity of the olfactory receptors;
  c) contacting the olfactory receptors with malodor compounds sequentially;
  d) measuring changes of odorant-induced neuronal activity;
  e) isolating one or more olfactory neurons that were activated by a malodor compound;
  f) isolating or isolating and amplifying the mRNA of the isolated olfactory receptors;

g) sequencing at least a portion of the transcriptome of the mRNA by Next-Generation Sequencing; and h) determining the identity of a group of malodor olfactory receptors by comparing the sequence of the transcriptome to a reference genome sequence of the same species and other vertebrate species.

Further provided herein is an isolated nucleic acid sequence having at least 60% sequence identity with a nucleic acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83 and SEQ ID NO: 85.

Also provided herein is an isolated nucleic acid sequence as describe above which encodes a polypeptide having at least 60% sequence identify with a polypeptide having an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

Further provided herein is an isolated polypeptide comprising an amino acid sequence having at least 60% sequence identify with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

Still yet further provided is a cell that is recombinantly modified to express a polypeptide, described above.

Further provided are assays for identifying compounds that bind to indole and/or skatole odorant receptors. In particular, provided herein is a method for identifying a compound that blocks, inhibits, modulates, and/or enhances the activity of an olfactory receptor that is activated by a compound selected from the group consisting of indole and skatole comprising a) contacting the receptor, or a chimera or fragment with a compound;

b) assaying whether the compound has an effect on the activity of the receptor; wherein the receptor is a polypeptide described above.

In one embodiment the activity of the compound is determined by comparing its binding to that of indole and/or skatole. In another embodiment, the receptor is contacted with a compound in the presence of skatole and/or indole under conditions that allow for the binding of the compound along with skatole and/or indole to the receptor.

In a further embodiment, provided herein, when a functional assay is used to measure binding activity, the step of measuring a signaling activity of receptors provided herein may comprise detecting a change in the level of a second messenger. In another embodiment, the measurement of a signalling activity is provided wherein the step of measuring a signaling activity comprises the measurement of guanine nucleotide binding/coupling or exchange, adenylate cyclase activity, cAMP, Protein Kinase C activity, Protein Kinase A activity phosphatidylinosotol breakdown, diacylglycerol, inositol triphosphate, intracellular calcium, calcium flux, arachidonic acid, MAP kinase activity, tyrosine kinase activity, melanophore assay, receptor initialization assay, FRET, BRET, or reporter gene expression. In a particular embodiment provided herein, the measuring of signaling activity comprises using a fluorescence or luminescence assay. Fluorescence and luminescence assays may comprise the use of Ca2+ sensitive fluorophores including Fluo-3, Fluo-4 or Fura dyes (Molecular Probes); Calcium 3 assay kit family (Molecular Devices) and aequorin.

DETAILED DESCRIPTION OF THE DRAWINGS

FIG. 1 displays a schematic overview of the malodor receptor de-orphanization process FIG. 2 displays Ca2+ imaging traces that are shown for 6 independent olfactory sensory neurons specifically activated by both indole and skatole (50 µM each).

FIG. 3 shows malodor receptor genes identified using the procedures outlined herein.

FIGS. 4A and 4B display human and additional mouse malodor receptors within the Olfr740 (4A) and Olfr665 (4B) families identified using the procedures outlined herein FIGS. 5A to 5E show the indole and skatole activity of mouse ORs Olfr743, Olfr746, and Olfr740 in HEK293T cells.

FIG. 8 shows the pairwise amino acid identities for the mouse Olfr740 family and their predicted human orthologs.

FIG. 9 shows the pairwise amino acid identities for the mouse Olfr665 family and their predicted human orthologs.

DETAILED DESCRIPTION

Figure 1:
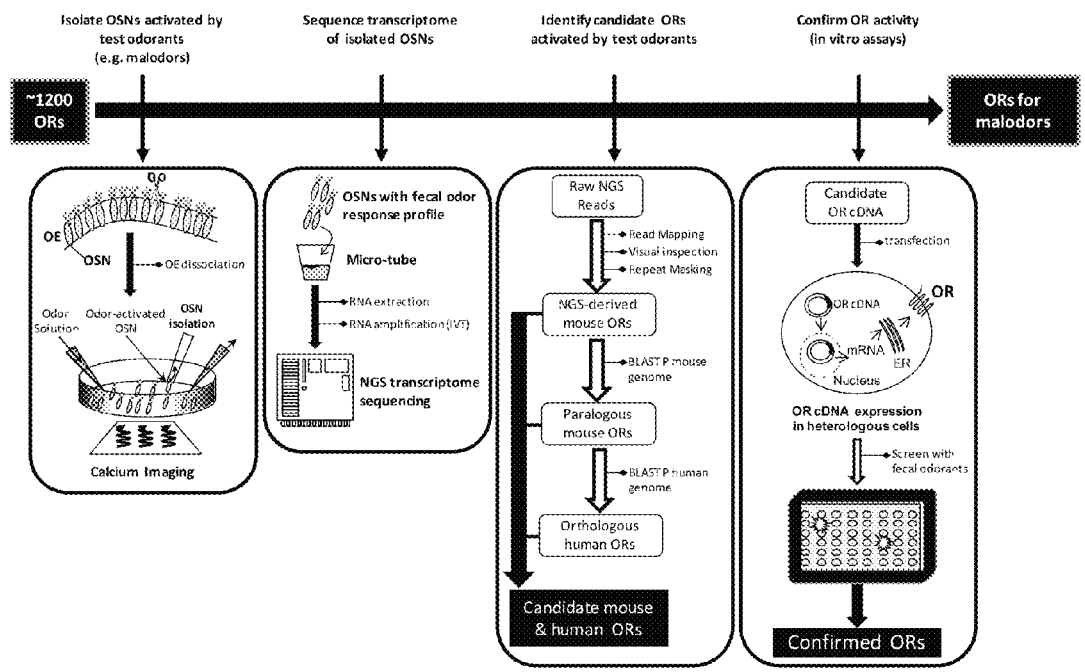

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Definitions

The following terms have the meanings ascribed to them unless specified otherwise.

"OR" refers to one or more members of a family of G protein-coupled receptors that are expressed in olfactory cells. Olfactory receptor cells can also be identified on the basis of morphology or by the expression of proteins specifically expressed in olfactory cells. OR family members may have the ability to act as receptors for olfactory transduction.

"Indole" and/or "skatole OR" refers to a member of the family of G protein-coupled receptors that is expressed in an olfactory cell, which receptors bind and/or are activated by indole and/or skatole in a binding or activity assay for identifying ligands that bind and modulate GPCRs by activating, inhibiting or enhancing their activity. Such assays are described below. Indole and/or skatole receptors herein will include fragments, variants, including synthetic and naturally occurring, and chimeras that respond to or bind indole and/or skatole.

"OR" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase.

"OR" polypeptides are considered as such if they pertain to the 7-transmembrane-domain G protein-coupled receptor superfamily encoded by a single ~1 kb long exon and exhibit characteristic olfactory receptor-specific amino acid motifs. The predicted seven domains are called "transmembrane" or "TM" domains TM I to TM VII connected by three predicted "internal cellular loop" or "IC" domains IC I to IC III, and three predicted "external cellular loop" or "EC" domains EC I to EC III. The motifs are defined as, but not restricted to, the MAYDRYVAIC motif overlapping TM III and IC II, the FSTCSSH motif overlapping IC III and TM VI, the PML-NPFIY motif in TM VII as well as three conserved C residues in EC II, and the presence of highly conserved GN residues in TM I [Zhang and Firestein (2002), The Olfactory Receptor Gene Superfamily of the Mouse. Nature Neuroscience: 5(2):124-33; Malnic et al., The Human Olfactory Receptor Gene Family: PNAS: 101(8):2584-9].

The "N terminal domain" region starts at the N-terminus and extends to a region close to the start of the first predicted transmembrane region. "Transmembrane domain," which comprises the seven predicted "transmembrane regions," refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods, as described in Kyte & Doolittle, J. Mol. Biol., 157:105-32 (1982), or in Stryer. The general secondary and tertiary structure of transmembrane domains, in particular the seven transmembrane domains of G protein-coupled receptors such as olfactory receptors, are known in the art. Thus, primary structure sequence can be designed or predicted based on known transmembrane domain sequences, as described in detail below. These transmembrane domains are useful for in vitro ligand-binding assays, both soluble and solid phase.

The phrase "functional assay" in the context of assays for testing compounds that modulate OR family member mediated olfactory transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction receptor-ligand interactions, second messenger concentrations (e.g., cAMP, cGMP IP3, or intracellular Ca2+), assays performed in vitro, in vivo, and ex vivo. It also includes other physiological effects such as increases or decreases of neurotransmitter or hormone release. Included herein are functional assays for a compound that increases or decreases a parameter that is indirectly or directly under the influence of an OR family member, e.g., functional, physical and chemical effects. Such functional assays or effects can be measured by any means known to those skilled in the art, e.g., changes in spectroscopic characteristics (e.g., fluorescence, luminescence, absorbance, refractive index), hydrodynamic (e.g., shape), chromatographic, solubility properties, patch clamping, voltage-sensitive dyes, whole cell currents, radioisotope efflux, inducible markers, oocyte OR gene expression; tissue culture cell OR expression; transcriptional activation of OR genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "blockers," "activators," "counteractants" and "modulators" of OR genes or proteins are used interchangeably to refer to inhibitory, activating, or modulating molecules identified using ex vivo, in vitro and in vivo assays for olfactory transduction, e.g., ligands, agonists, antagonists, inverse agonists and their homologs and mimics. Inhibitors and blockers are compounds that, e.g., bind to, partially or totally block stimulation, decrease, prevent, delay activation, inactivate, desensitize, or down regulate olfactory transduction, e.g., antagonists. Activators are compounds that, e.g., bind to, stimulate, increase, open, activate, facilitate, enhance activation, sensitize, or up regulate olfactory transduction, e.g., agonists. Modulators include compounds that, e.g., alter the interaction of a receptor with: extracellular proteins that bind activators or inhibitors (e.g., odorant-binding proteins, lipocalin and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors. Modulators can include genetically modified versions of OR family members, e.g., with altered activity, as well as naturally occurring and synthetic ligands, antagonists, agonists, small chemical molecules and the like. Such assays for inhibitors and activators include, e.g., expressing OR family members in cells or cell membranes, applying putative modulator compounds, in the presence or absence of flavor or fragrance molecules, e.g., perfumery raw materials, perfume formulations, or malodors, and then determining the functional effects on olfactory transduction, as described above. Samples or assays comprising OR family members that are treated with a potential activator, inhibitor, or modulator are compared to control samples without the inhibitor, activator, or modulator to examine the extent of modulation. Control samples (untreated with modulators) are assigned a relative OR activity value of 100%. Inhibition of an OR is achieved when the OR activity value relative to the control is about 80%, optionally 50% or 25-0%. Activation of an OR is achieved when the OR activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention in vivo, ex vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions or single nucleotide polymorphisms) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" means also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome (e.g. stable expression). The expression systems can have the ability to self-replicate or not, i.e., drive only transient expression in a cell. The term includes recombinant expression "cassettes" which contain only the minimum elements needed for transcription of the recombinant nucleic acid.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa, HEK-293, and the like, e.g., cultured cells, explants, and cells in vivo.

In one embodiment provided herein is an isolated nucleic acid sequence having at least 60%, 65%, 70%, 75%, 80%, 85%, 90%, 95% or 98% sequence identity with a nucleic acid sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83 and SEQ ID NO: 85.

In one embodiment provided herein is an isolated nucleic acid sequence as described above which encodes a polypeptide having at least 60%, 65%, 70%, 75%, 80%, 85%, 90%, 95% or 98% sequence identity with a polypeptide having an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO:

32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

In a further embodiment provided herein is an isolated polypeptide comprising an amino acid sequence having at least 60%, 65%, 70%, 75%, 80%, 85%, 90%, 95% or 98% sequence identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86, or a biologically active fragment of such a polypeptide.

A method enables one skilled in the art to rapidly identify the relatively small subset of odorant receptors (ORs), within the total population of ~1,200 ORs that exist in the rodent genome, whose human genetic counterparts likely encode a specific odor characteristic in humans. FIG. 1 is a schematic overview of the method. Intact mouse olfactory epithelium (OE) tissue is dissociated by mechanical and enzymatic treatment into single cells. The resulting individual olfactory sensory neurons (OSNs) are plated onto glass coverslips and loaded with a calcium indicator dye (e.g., Fura-2) to detect cell activity. The coverslips are then placed in a perfusion chamber and bathed in a physiological salt solution. Malodorous test odorants are diluted in physiological saline and perfused over the cells. OSN activity is then detected by monitoring the changes in intracellular calcium flux via a change in Fura-2 fluorescence and a fluorescent microscope. Importantly, in some instances, only one or two of ~1200 possible OR genes are expressed in a given OSN. This means that the activity of a given OSN is driven exclusively by a single type, or two types, of OR protein(s) expressed on the cell surface. A semi-automated calcium imaging system with a finely controlled odorant injection system and a movable stage allows for monitoring of >1,500 OSNs in a single experiment. With ~1,200 OR genes in mouse, this throughput ensures a representative sampling of the entire OR repertoire. One or more OSNs that respond to one or more test odorant are collected using a glass micropipette and displaced in a microtube for subsequent RNA extraction, amplification, and Next-Generation Sequencing (NGS) of OSN transcriptomes. NGS-based transcriptome sequencing from very small amounts of starting material (<100 cells) has been reported in the literature. However, it has not yet been applied for the specific purpose of G-Protein Coupled Receptor (GPCR) deorphanization to the best of our knowledge; in particular olfactory receptors. Using the methods described herein, multiple OSNs can be pooled in the same microtube if desired. Raw sequence reads are then mapped to a reference genome, visually inspected for proper alignment and annotation, and analyzed for false-positive mapping due to, for example, genome repeat sequences. The result is a list of candidate mouse ORs that are likely activated by the same malodorous test odorant(s) used to screen mouse OSNs. The candidate mouse OR protein sequences are then used to query (e.g., BLASTP) public mouse genome databases to obtain a full list of candidate mouse OR sequences. These candidates are related by sequence homology (i.e. paralogous) to the NGS-derived OR sequences originally identified from the neurons that were activated by indole and/or skatole. The full list of mouse paralogs (NGS and BLASTP-derived) are then used to query public human genome databases to obtain a list candidate human OR sequences that are related (i.e. orthologous) to the mouse OR sequences. The result is a complete list of candidate mouse and human ORs that are likely activated by the test odorants. To confirm the activity of the resulting candidate ORs genes, cDNAs of said genes can be cloned into available expression vectors and transfected into cultured cells that are amenable to high-throughput screening (e.g. HEK293T). The resulting cell lines, each containing a recombinantly expressed candidate OR cDNA, can then be screened in a cell-based activity assay with the test odorants used in calcium imaging and other structurally- or organoleptically-related odorants.

In a particular embodiment olfactory epithelium containing native olfactory neurons from a non-human mammal (e.g., mouse) are isolated and dissociated into single cells according to for example Araneda et al. (2004), A Pharmacological Profile of the Aldehyde Receptor Repertoire in Rat Olfactory Epithelium. Journal of Physiology: 555:743-756. In a particular embodiment, each neuron expresses only one or two receptors at a time. The olfactory tissue used to generate olfactory neurons is, in one embodiment, from a non-human mammal that has publically available data concerning the receptors and associated sequences. This includes mouse, rat and hamster tissue. The dissociation protocol should be optimized in order to ensure high rate of surviving recordable neurons. In a particular embodiment a minimum of approximately 1,500 distinct sensory neurons are recorded.

In a further embodiment, the indicator is selected from a fluorescent calcium indicator dye, a calcium indicator protein, a fluorescent cAMP indicator, a cAMP response element (CRE) mediated reporter protein, a biochemical cAMP HTRF assay, a beta-arrestin assay, or an electrophysiological recording. Particularly, a calcium indicator dye is selected that can be used to monitor the activity of olfactory receptors expressed on the membrane of the olfactory neurons (e.g., Fura-2 AM).

In a particular embodiment, compounds are screened sequentially and the odorant-dependant changes in calcium dye fluorescence are measured using a fluorescent microscope or fluorescent-activated cell sorter (FACS).

As an example, olfactory neurons are isolated after screening with one or more malodor compounds using either a glass microelectrode attached to a micromanipulator or a FACS machine. More particularly at least 1 neuron is isolated. Mouse olfactory sensory neurons are screened by Ca2+ imaging similar to procedures previously described (Malnic et al., 1999; Areneda et al., 2004). Particularly, a motorized movable microscope stage is used to increase the number of cells that can be screened to at least 1,500 per experiment. Since there are approximately 1,200 different olfactory receptors in the mouse and each olfactory sensory neuron expresses only 1 or 2 of 1,200 olfactory receptor genes, this screening capacity will cover virtually the entire mouse odorant receptor repertoire. In other words, the combination of calcium imaging for high-throughput olfactory sensory neuron screening leads to the identification of nearly all of the odorant receptors that respond to a particular profile of odorants. In a particular aspect, odorants that respond to both indole and skatole, two common latrine malodor compounds can be isolated.

For calcium imaging of olfactory neurons, the main olfactory epithelium may be dissected from a mouse before neuronal dissociation. Dissected olfactory epithelium may then be transferred to a dissociation buffer for mechanical and enzymatic dissociation. Dissociated neurons may then be seeded onto a coverslip allowing the screening of thousands of cells by fluorescence microscopy and the cells may be loaded with a calcium sensitive dye (Fura-2 AM) for example for about 30 minutes at 31° C. and transferred onto the microscope ready for screening. Cells are stimulated by perfusing diluted solutions of odorants (in physiological saline) over the dissociated olfactory neurons. The rare cells that respond to the malodor compound are identified by for example stimulating the receptors with 50 µm of the malodor compounds and then by monitoring the intracellular $Ca^{2+}$ flux indicated by changes in Fura-2 fluorescence. After analysis, responding cells may be retrieved from a glass coverslip with a suction micropipette. Isolated cells are then pooled into one sample for subsequent identification of the odorant receptor genes expressed as mRNA in the responding cells.

In a particular embodiment, the mRNA of olfactory neurons are purified and amplified according to the method generally described in Marko, N. F., et al., (2005) A robust method for the amplification of RNA in the sense orientation. BMC genomics, 6, 27; doi:10.1186/1471-2164-6-27 (Eberwine method). At least a portion of the transcriptome (up to and including the entire transcriptome) is sequenced using Next-Generation Sequencing (NGS) or hybridized to known genes using Microarray technologies. NGS is generally discussed and described in Metzker, M. L. (2010). Sequencing technologies—the next generation. Nature reviews. Genetics, 11(1), 31-46; doi:10.1038/nrg262. In a particular embodiment, a minimum of 5 neurons presenting the same response profile are pooled and the mRNA are amplified by two consecutive rounds of in vitro transcription (IVT). The mRNA is released by cell lysis immediately after picking; no DNAse and no purification steps are carried out. The amplification may be done according to MesageAmpII aRNA kit (Ambion, AMA1751) with the following parameters: two rounds of consecutive 14 hour long IVT.

In a further embodiment, the identity of a group or gene family of malodor olfactory receptors is determined (e.g., up to as many as the number of neurons picked) by comparing the results of the NGS to a reference genome sequence of the same species. Particularly, the putative malodor receptors will be the most highly abundant mRNA in the olfactory neuron-derived NGS sample or present in more than one independent biological replicate. Because of the combinatorial nature of the olfactory code (one compound activates many ORs and one OR can be activated by many compounds), pooling several neurons activated by given compounds allows the retrieval of virtually all of the receptors responsible for the perception of these molecules in a single NGS experiment. Pooling functionally similar neurons thus greatly improves the deorphanization throughput and speed.

Standard bioinformatics tools are then used to identify the most closely related human odorant receptor(s) to other putative mammalian (non-human) malodor receptor(s) under the assumption that homologous receptor sequences retain similar function. One study demonstrated that ~82% of orthologous OR gene pairs responded to a common ligand, suggesting that as many as ~18% of orthologous gene pairs may respond to a different ligand; further, 33% of paralogous OR gene pairs responded to a common ligand, suggesting that at least ~67% of paralogous pairs may respond to a different ligand [Adipietro et al. (2012) Functional Evolution of Mammalian Odorant Receptors. PLoS Genet 8(7): e1002821. doi:10.1371/journal.pgen. 1002821]. Default parameters of BLASTP and/or BLASTN algorithm may be used.

The human or non-human mammalian malodor receptor may be adapted to a functional assay that can be used to identify compounds that mimic, block, modulate, and/or enhance the activity of a malodor compound. In particular the assay may be a cell assay and the method for identifying compounds may be a high-throughput screening assay. More particularly, provided herein are receptor-based assays adaptable for high-throughput screening of receptors with compound libraries for the discovery of modulating compounds (e.g., blocking, enhancing, and masking).

In a particular embodiment, malodor receptor gene sequences are identified from indole and skatole-sensitive cells as follows: Pooled neurons are heated to 75° C. for 10 minutes to break the cell membrane and render their mRNA available for amplification. This amplification step is important when applying NGS technologies with limited amount of starting material, typically between 1 to 15 cells. A linear amplification according to the Eberwine method (IVT) ensures the maintenance of the relative transcription levels of expressed genes. Two consecutive overnight (14 h) rounds of in vitro transcription are used to yield sufficient amounts of cRNA; Amplified cRNA is then used to generate an Illumina HiSeq cDNA library. The resulting short sequences of typically 75-150 base pairs (commonly referred to as "reads") are aligned against the reference genome of the mouse (such as UCSC version mm9 or mm10) in order to build the full transcriptome of these cells. Quantitative analysis of the transcriptome data yields a list of transcribed odorant receptor genes and their respective expression levels. Odorant receptor genes that show the most abundant levels of mRNA (most abundant "reads") or are present in more than one replicate experiment are considered putative indole and skatole receptors.

The predicted mouse OR genes are then used to mine the latest versions of both the mouse and human genome databases in order to identify the most closely related receptors (i.e., highest sequence similarity) in mouse (paralogous genes) and in human (orthologous genes). This process may be performed using the BLAST search algorithm (publically available at the NCBI website), a sequence similarity search tool, where every putative gene sequence previously obtained from the initial transcriptome analysis is used as a query sequence. The newly identified genes identified from this data mining process are also considered as potential malodor receptors under the assumption that paralogous and orthologous genes are highly likely to possess similar activities.

In a particular embodiment, pairwise comparison of sequence homology is carried out to identify closely related receptors in mouse and humans using the following iterative scheme:

| Step | Query sequence | BLASTN/BLASTP Result |
|---|---|---|
| 1. | Mouse candidate 1 → | Mouse paralog 1 and human ortholog 1 |
| 2. | Mouse paralog 1 → | Human ortholog 2 |

| Step | Query sequence | BLASTN/BLASTP Result |
|------|----------------|----------------------|
| 3. | Human ortholog 1 → | Human paralog 1 |
| 4. | Human ortholog 2 → | Human paralog 2 |

Paralog = homolog in same species
Ortholog = homolog in other species

Paralogous genes are then aligned using a multiple alignment tool in order to generate a phylogenetic tree. Functional in vitro data can be interpreted in the light of such a phylogenetic relationship between closely related but distinct receptors. This step is essential in the identification of complete OR gene families that respond, to varying degrees, to the test compounds, for example indole and skatole.

To complete the deorphanization process, the candidate OR genes are further expressed in vitro for confirmation of activity against the compounds used to isolate the olfactory sensory neurons and other structurally-related compounds of interest. In one embodiment, to complete the deorphanization process, the candidate OR genes are further expressed in vitro for confirmation of activity against the compounds initially used to isolate said olfactory sensory neurons. The same candidate OR genes expressed in vitro are further screened with other structurally-related compounds of interest to identify, e.g., activators, inhibitors, or modulators of the receptor.

Using the process and method described herein the following receptors have been identified directly by sequencing (NGS) the transcriptome of olfactory neurons responding to indole and skatole malodors (mouse ORs). Human indole and skatole receptors with the highest degree of amino acid identity to the mouse ORs were subsequently identified by searching available genome databases (Table 1). Mouse receptor Olfr740 and Olfr665 were initially identified through the NGS method described herein after isolating or "picking" responding cells after exposure to both indole and skatole. Corresponding human homologous receptors, OR11G2 and OR52N2 respectively, were further identified by amino acid sequence similarity comparisons. As demonstrated in examples 4 and 5, the candidate mouse receptors Olfr740 and Olfr665 and their human counterparts OR11G2 and OR52N2 were activated in vitro by indole and skatole and are thus described as indole and/or skatole receptors. Similarly, the candidate mouse receptors Olfr 746, Olfr745, Olfr207, Olfr211 and Olfr257 led to identification of the human receptors OR11H4, OR11H6, OR5AC2, OR4C15 and OR8S1, respectively, following the same steps. These human OR genes also responded to both indole and skatole in vitro. Taken together, seven out of seven tested putative human receptors identified by the method described herein were confirmed as indole and skatole receptors further supporting the method for efficient human indole and skatole receptor identification.

This approach to odorant receptor deorphanization has several major advantages over previously established single cell RT-PCR methods. First, by pooling multiple neurons sharing similar binding properties to odors and/or aromas, a unique mRNA sequencing experiment (NGS) identifies virtually all the receptors that are activated by the target malodor compounds.

Therefore the throughput is higher than what was previously achieved. Second, because multiple cells are pooled into one sample, multiple ORs for a particular compound are revealed in a single experiment. In a particular embodiment, the selection of genes through a comprehensive comparison of replicate samples across experiments. Third, NGS does not require the use of PCR primers specific to an OR. NGS also does not require the use of degenerate primers specific to ORs, which are problematic and often lead to false positives due to non-linear or non-specific PCR amplification. In particular, since OR coding sequences lie within a single exon, sample contamination with genomic DNA can easily lead to an aspecific amplification of OR gene sequences. Fourth, RT-PCR analysis is difficult to perform on pooled samples because of the inherent false positive rate. Single cell mRNA hybridization experiments have been performed using of high-density DNA microarray chips. However, this approach is generally less sensitive than NGS and is further restricted to known genes for which corresponding DNA probes need to be synthesized. Hence, the use of NGS is significantly advantageous to rapidly identify OR and ultimately results in a more accurate selection of candidate receptors compared to the standard (e.g., RT-PCR and microarray) approaches.

In a further embodiment, mouse receptors identified from isolated olfactory neurons that respond to both indole and skatole are modified at their N-terminus with a short polypeptide sequence (e.g., bovine rhodopsin receptor—Rho, or Flag), transiently expressed in HEK 293T cells, and stimulated separately with indole and skatole to confirm their identity as bona fide indole/skatole receptors. Co-expression of the human G alpha subunit $G\alpha_{olf}$ (SEQ ID NO: 21) activates the Gs transduction pathway that leads to an internal cAMP increase upon binding to the appropriate ligand. The results confirm the identity of Olfr740 (SEQ ID NO: 1 and SEQ ID NO: 2), Olfr743 (SEQ ID NO: 5 and SEQ ID NO: 6), and Olfr746 (SEQ ID NO: 37 and SEQ ID NO: 38) as indole-skatole receptors.

In another aspect, human receptor OR52N2 (SEQ ID NO: 11 and SEQ ID NO: 12) was identified because of its sequence similarity to mouse Olfr665 (SEQ ID NO: 9 and SEQ ID NO: 10), an indole/skatole receptor isolated from olfactory neurons responding to both indole and skatole (Example 6). Human receptor OR11G2 (SEQ ID NO: 13 and SEQ ID NO: 14) was identified because of its sequence similarity to mouse Olfr740 (SEQ ID NO: 1 and SEQ ID NO: 2), an indole/skatole receptor isolated from olfactory neurons responding to both indole and skatole (Example 6). Human receptor OR5AC2 (SEQ ID NO: 75 and SEQ ID NO: 76) was identified because of its sequence similarity to mouse Olfr207 (SEQ ID NO: 77 and SEQ ID NO: 78), an indole/skatole receptor isolated from olfactory neurons responding to both indole and skatole (Example 6). Human receptor OR4C15 (SEQ ID NO: 79 and SEQ ID NO: 80) was identified because of its sequence similarity to mouse Olfr1211 (SEQ ID NO: 81 and SEQ ID NO: 82), an indole/skatole receptor isolated from olfactory neurons responding to both indole and skatole (Example 6). Human receptor OR8S1 (SEQ ID NO: 83 and SEQ ID NO: 84) was identified because of its sequence similarity to mouse Olfr257 (SEQ ID NO: 85 and SEQ ID NO: 86), an indole/skatole receptor isolated from olfactory neurons responding to both indole and skatole (Example 6). Mouse receptor Olfr665 (SEQ ID NO: 9 and SEQ ID NO: 10) was identified directly from NGS data from isolated olfactory neurons responding to both indole and skatole (Example 6). Mouse receptor Olfr740 (SEQ ID NO: 1 and SEQ ID NO: 2) was identified directly from NGS data from isolated olfactory neurons responding to both indole and skatole (Example 6). Mouse receptor Olfr736 (SEQ ID NO: 27 and SEQ ID NO: 28) was identified because of its sequence similarity to mouse Olfr740 (SEQ ID NO: 1 and SEQ ID NO: 2), an indole/skatole receptor isolated from olfactory neurons and failed to respond to indole or skatole likely because of lack of cell surface expression. Mouse receptor Olfr747 (SEQ ID NO: 39 and SEQ ID NO: 40) and Olfr748 (SEQ ID NO: 41 and SEQ ID NO: 42) were also identified because of their sequence similarity to mouse Olfr740 (SEQ ID NO: 1 and SEQ ID NO: 2) and exceptionally failed to respond to indole or skatole despite proper cell surface expression as evaluated by immunostaining assays. This underlines the diversifying nature of the olfactory receptors where highly similar sequences do not always share the same response profile.

The receptors are modified with the Rho sequence and stably expressed in HEK 293T cells. Co-expression of the human G alpha subunit $G\alpha_{15}$ activates the Gq transduction pathway that leads to an internal $Ca^{2+}$ increase upon binding to the appropriate ligand.

The above process and the results obtained so far serve to validate the process for rapid and reliable identification of mammalian odorant receptors for malodor compounds.

Still yet further provided is a cell that is recombinantly modified to express a polypeptide described above.

Further provided are assays for identifying compounds that bind to indole and/or skatole odorant receptors. In particular, provided herein is a method for identifying a compound that blocks, inhibits, modulates, and/or enhances the activity of an olfactory receptor that is activated by a compound selected from the group consisting of indole and skatole comprising a) contacting the receptor, or a chimera or fragment thereof with a compound;

b) assaying whether the compound has an effect on the activity of the receptor;

wherein the receptor is a polypeptide described above.

In one embodiment the activity of the compound is determined by comparing its binding to that of indole and/or skatole. In another embodiment, the receptor or a chimera or fragment thereof is contacted with a compound in the presence of skatole and/or indole under conditions that allow for the binding of the compound along with skatole and/or indole to the receptor.

In a further embodiment, a compound is contacted to a receptor, or a chimera or fragment thereof that is activated by a compound selected from the group consisting of indole and skatole wherein the receptor, or a chimera or fragment thereof is expressed in a cell that is recombinantly modified to express the polypeptide.

The activity of the compound can be determined using in vivo, ex vivo, in vitro and synthetic screening systems, which typically allow for screening of large libraries of compounds, containing as many as 10,000s of compounds or mixtures of compounds.

In another embodiment, the contacting is performed with liposomes or virus-induced budding membranes containing the polypeptides described herein.

In another embodiment, the methods for identifying compounds that bind to the receptors that bind to skatole and/or indole, may be performed on a membrane fraction from cells expressing the polypeptides described here.

The following examples are illustrative only and are not meant to limit the scope of invention as set forth in the Summary, Description or in the Claims.

EXAMPLES

Example 1

Screening of Mouse Olfactory Sensory Neurons to Identify Receptors that Bind Indole and/or Skatole The olfactory epithelium containing native olfactory neurons from a mouse was isolated and dissociated into single cells and then transferred to a dissociation buffer for a gentle mechanical and enzymatic dissociation. In order to optimize the dissociation protocol, the general procedure for making fresh dissociation buffer was followed as set forth in Araneda et al. (2004), A Pharmacological Profile of the Aldehyde Receptor Repertoire in Rat Olfactory Epithelium. Journal of Physiology: 555:743-756 with the following modifications: DNAse I instead of DNAse II, Ca2+ concentration elevated to 5 mM and pH adjusted at 7.35 at 32°. Dissociated neurons were then seeded on a coverslip allowing the screening of >2,500 cells by fluorescence microscopy. The cells were then loaded with a calcium sensitive dye (Fura-2 AM) for 30 minutes at 31° C. and transferred onto a microscope ready for screening. Dissociated olfactory neurons were screened as previously described (Malnic et al., 1999; Araneda et al., 2004), but with a motorized movable microscope stage to increase the number of cells that can be screened. The cells were then stimulated by perfusing diluted solutions of odorants (in physiological saline) over the dissociated olfactory neurons.

Figure 2:
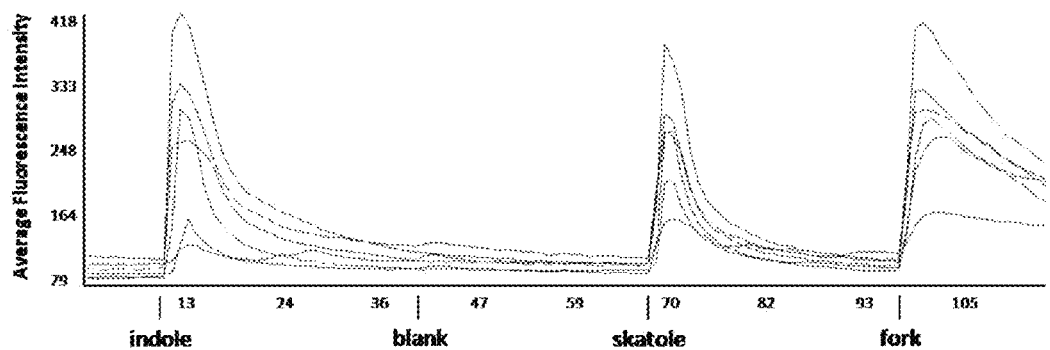

Olfactory neurons that responded to indole and skatole were identified by stimulating receptors with 50 μm indole followed by 50 μm skatole and monitoring the intracellular Ca2+ flux indicated by changes in Fura-2 fluorescence. FIG. 2 displays Ca2+ imaging traces for 6 independent olfactory sensory neurons specifically activated by both indole and skatole (50 μM each). All cells were also stimulated with 20 μM forskolin (fork), a pharmacological activator of the enzyme adenylate cyclase ACIII, to confirm viability and neuronal identity of the cells. Timescale units on the X axis, 6 seconds frame. Average Fluorescence Intensity, relative fluorescent unit as a result of a ratiometric 340/380 nm recordings.

Example 2

Isolation and Amplification of mRNA from Indole and Skatole Sensitive Cells to Generate cDNA Sequences of the "Malodor Receptor" Gene for the Indole and Skatole Sensitive Receptors The activated olfactory sensory neurons of Example 1 were isolated using a glass suction micropipette and then pooled into one sample for subsequent identification of the odorant receptor genes expressed as mRNA in the responding cells. Malodor receptor gene sequences were identified from indole and skatole-sensitive cells as follows: Four sets of more than five (5) olfactory neurons (6, 10, 15, and 15 cells each) activated by one or more malodor compounds were isolated using a glass microelectrode attached to a micromanipulator. Micropipettes were engineered from Borosilicate glass (Item # B150-86-10, Sutter Instruments) and pulled using a microelectrode puller (Model P-1000, Sutter Instruments) under the following conditions: Heat, ramp temp+20° C.; Pull=0; Vel=120; Pressure=500. Pulled pipette tips were broken manually and secured onto a Newport micromanipulator (model MW3R) for isolating olfactory sensory neurons activated by indole and skatole as determined in a calcium imaging assay. Activated OSNs were isolated by gentle suction applied to the back-end of the micropipette.

The mRNA of neurons was purified and amplified according to the Eberwine method (MessageAmp II aRNA kit—Ambion, AM1751). Pooled neurons were heated to 75° C. for 10 minutes in Resuspension Buffer (SuperScript III Cells Direct cDNA system, 46-6321-Invitrogen) to break the cell membrane and to render their mRNA available for amplification. A linear amplification according to the Eberwine method (in vitro transcription) ensures the maintenance of the relative transcription levels of expressed genes. First-strand cDNA was obtained according to the Ambion kit with a incubation for 2 h at 42° C. Second strand cDNA synthesis was performed using the same kit after a second incubation for 2 h at 16° C. Doubled stranded cDNA was used as a template to generate the corresponding cRNA (14 h incubation at 37° C.), which is then purified. These cRNA synthesis steps were repeated for a second IVT. The two consecutive overnight (14 h) rounds of in vitro transcription yielded sufficient amounts of cRNA; Amplified cRNA was then used to generate an Illumina HiSeq cDNA library. The sequence of the entire transcriptome was then obtained by Next-Generation Sequencing (NGS).

Figure 3:
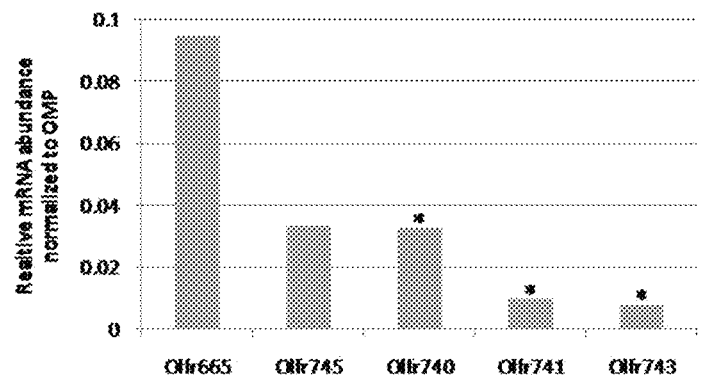

The identity of the mouse malodor, specifically indole and/or skatole, olfactory receptors was determined by comparing the NGS results to a reference genome sequence of the same species. For this, the resulting short sequences of 150 base pairs (commonly referred to as reads) derived from NGS were aligned against the reference genome of the mouse (UCSC version mm9 or mm10) in order to build the full transcriptome of these cells. Quantitative analysis of the transcriptome data yielded a list of transcribed odorant receptor genes and their respective expression levels. Odorant receptor genes that showed abundant levels of mRNA (abundant reads) or were present in more than one replicate experiment were considered candidate indole and skatole receptors and are set forth in FIG. 3, which summarizes representatives NGS results from 4 independent skatole/indole cell picking experiments. The bars represent candidate indole/skatole OR genes with the most abundant mRNAs that were retained after visual inspection. The Y axis represents the mRNA abundance levels normalized to the level of OMP mRNA, accounting for the number of OSNs picked per sample. Star (*), receptors identified in more than one experiment. OMP (Olfactory Marker Protein) is a specific biomarker for mature olfactory neurons. By coupling calcium imaging and NGS as described above the following 5 receptor sequences were identified as putative mouse indole and skatole ORs: Olfr665 (SEQ ID NO: 9 and SEQ ID NO: 10), Olfr740 (SEQ ID NO: 1 and SEQ ID NO: 2), Olfr741 (SEQ ID NO: 3 and SEQ ID NO: 4), Olfr743 (SEQ ID NO: 5 and SEQ ID NO: 6), and Olfr745 (SEQ ID NO: 7 and SEQ ID NO: 8).

Example 3

Identification of the Mouse and Human Malodor Receptors

The identification of a subset of 5 mouse indole and skatole ORs among ~1,200 ORs in the mouse genome by coupling calcium imaging and NGS (Examples 1-2) enabled the rapid identification of additional mouse and new human indole and skatole ORs by in silico methods. Since ORs with similar overall amino acid identity are likely to display similar odorant response profiles [Adipietro et al. (2012)], a list of candidate indole and skatole ORs was expanded by querying public mouse and human genome databases with the mouse OR sequences derived from NGS analysis of indole/skatole sensitive olfactory sensory neurons isolated by calcium imaging. The identity of the mouse malodor olfactory receptors was determined by comparing the results of the NGS to a reference genome sequence of the same species. The putative malodor receptors will be the most highly abundant mRNA in the olfactory neuron-derived NGS sample or present in more than one independent biological replicate, but not in a control sample lacking olfactory neurons that respond to the malodor(s). Standard bioinformatics tools were used to identify the most closely related human odorant receptor(s) to the putative mammalian (non-human) malodor receptor(s) under the assumption that homologous sequence receptors retain similar function (Adipietro et al. (2012)). Default parameters of BLASTP and/or BLASTN algorithm were used. Table 1 lists the identified mouse odorant receptors (OR) and the predicted human orthologs.

TABLE 1

| NGS Identified Mouse ORs | Human Orthologs | Amino Acid Identity |
| --- | --- | --- |
| Olfr665 (SEQ ID NO: 10) | OR52N2 (SEQ ID NO: 12) | 77% |
| Olfr740 (SEQ ID NO: 2) | OR11G2 (SEQ ID NO: 14) | 77% |
| Olfr741 (SEQ ID NO: 4) | OR11G2 (SEQ ID NO: 14) | 73% |
| Olfr743 (SEQ ID NO: 6) | OR11G2 (SEQ ID NO: 14) | 75% |
| Olfr745 (SEQ ID NO: 8) | OR11H6 (SEQ ID NO: 16) | 82% |

Figure 4A:
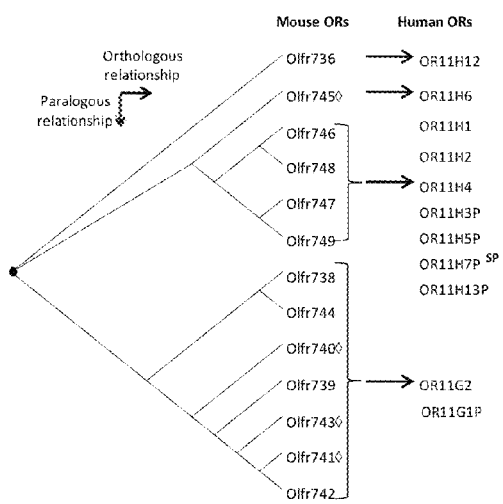
Figure 4B:
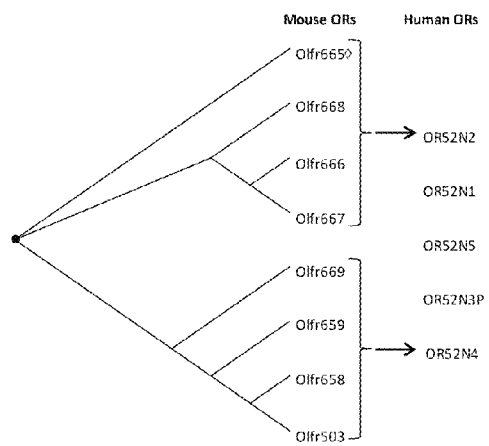

The related human protein sequences are within at least 60% sequence identity to the NGS identified mouse OR sequences listed in Table 1. Identity levels are given relative to the amino acid sequence pairwise comparison after BLASTP algorithm. Twenty six (26) new human and mouse ORs were identified through BLASTP queries of public genome databases (default parameters). Sixteen (16) were closely related to the NGS-derived genes Olfr740 (SEQ ID NO: 1 and SEQ ID NO: 2), 741 (SEQ ID NO: 3 and SEQ ID NO: 4), 743 (SEQ ID NO: 5 and SEQ ID NO: 6), 745 (SEQ ID NO: 7 and SEQ ID NO: 8) and define the 740 family. Ten (10) were closely related to the NGS-derived receptor Olfr665 (SEQ ID NO: 9 and SEQ ID NO: 10) and define the Olfr665 family. FIGS. 4A and 4B depict the phylogenetic relationships of candidate mouse indole and skatole OR genes and their predicted human orthologs belonging to the Olfr740 (FIG. 4A) and Olfr665 (FIG. 4B) receptor families. The relationships were obtained by protein sequence-based Neighbor-Joining phylogenetic tree reconstruction. Corresponding human orthologs are indicated by arrows. Human OR gene names annotated as pseudogenes are marked with a 'P'. Pseudogenes are likely non-functional. OR11H7P is a segregating pseudogene (SP) with known functional alleles. Diamonds (◊) designate receptors initially identified by NGS. To determine the amino acid identities for additional candidate mouse and human indole and skatole ORs, the full length protein sequences were manually aligned based on highly conserved amino acid motifs across the entire OR repertoire (Bioedit sequence alignment tool, version 7.0.5.3). FIG. 8 displays the pairwise amino acid identities for the mouse Olfr740 family and their predicted human orthologs. FIG. 9 displays the pairwise amino acid identities for the mouse Olfr665 family and their predicted human orthologs.

Example 4

Indole and Skatole Activity of Mouse ORs Olfr743, Olfr746, and Olfr740 in HEK293T Cells.

Figures 5A, 5B, 5C, 5D, 5E:
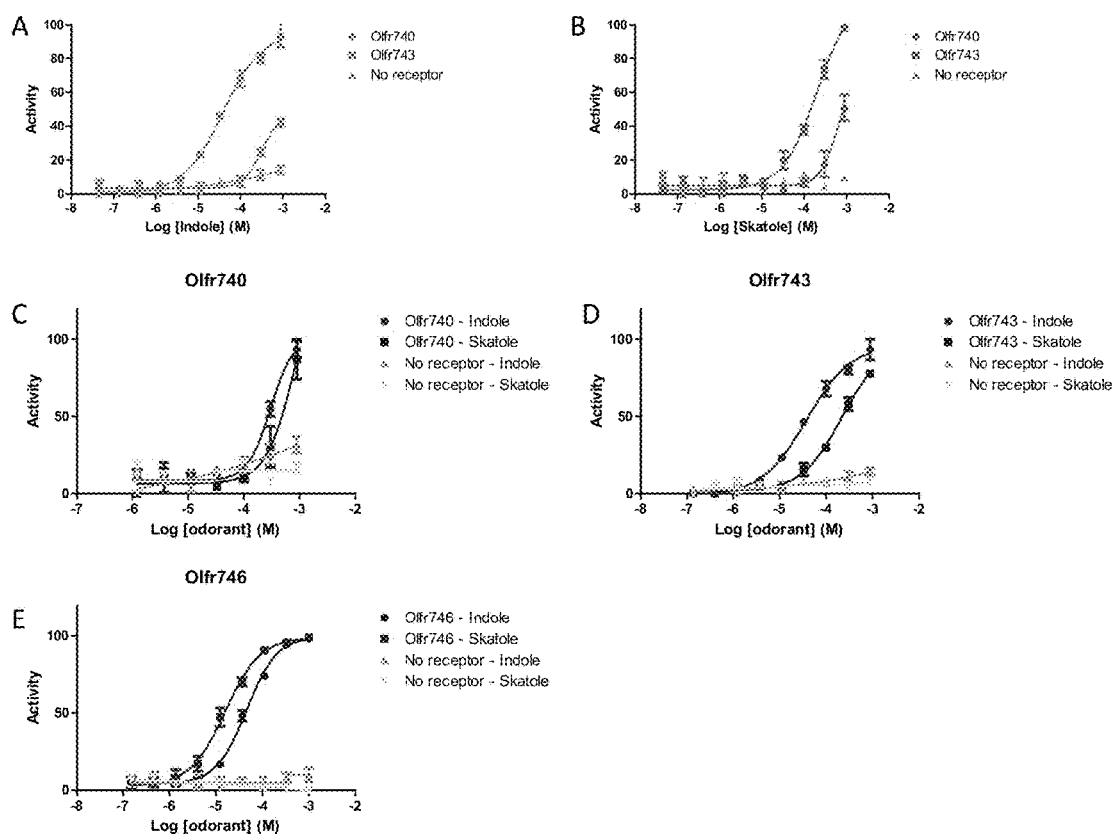

The activity of candidate mouse receptors Olfr740 (SEQ ID NO: 1 and SEQ ID NO: 2), Olfr743 (SEQ ID NO: 5 and SEQ ID NO: 6), and Olfr746 (SEQ ID NO: 37 and SEQ ID NO: 38) to both indole and skatole malodors were confirmed in cell-based cAMP assays. In FIGS. 5A and 5B, FLAG Rho-tagged (SEQ ID 18) Olfr743 (SEQ ID NO: 6) and Olfr740 (SEQ ID NO: 2) cDNA sequences were co-transfected with $G\alpha_{olf}$ (SEQ ID NO: 21) and exposed to increasing concentrations of indole (left) or skatole (right). FIGS. 5C and 5D are repeat experiments showing similar activity of Olfr740 (SEQ ID NO: 2) with Olfr743 (SEQ ID NO: 6) with indole and skatole. In FIG. 5E, the FLAG Rho-tagged (SEQ ID 18) Olfr746 (SEQ ID NO: 38) cDNA sequence was co-transfected with $G\alpha_{olf}$ (SEQ ID NO: 21) and exposed to increasing concentrations of indole or skatole. Odorant-induced activity was detected by measuring cAMP levels in the cytosol using the HTRF approach (CisBio kit). A dose-dependent increase of receptor activity is shown for all three receptors to both molecules. Co-transfection of HEK cells with $G\alpha_{olf}$ (SEQ ID NO: 21) alone (no receptor) were used as controls for non-specific activity (control). Activity is defined as the baseline corrected HTRF ratios normalized to the highest signal in the experiment. The results are displayed in FIGS. 5A to 5E. All three receptors show specific dose dependent activity to the malodor compounds and, as such, validate the process for identifying receptors for these compounds. Mouse receptors Olfr740 (SEQ ID NO: 1 and SEQ ID NO: 2) and Olfr743 (SEQ ID NO: 5 and SEQ ID NO: 6) were identified from isolated olfactory neurons that responded to both indole and skatole. Mouse receptor Olfr746 (SEQ ID NO: 37 and SEQ ID NO: 38) was identified in silico by database mining using Olfr740 (SEQ ID NO: 2) and Olfr743 (SEQ ID NO: 6) as query sequences. The receptors are modified at their N-terminus with the FLAG tag and the first 20 amino acids of the bovine rhodopsin receptor (SEQ ID 18), transiently expressed in HEK 293T cells, and stimulated separately with indole and skatole to confirm their identity as bona fide indole/skatole receptors. Co-expression of the human G alpha subunit $G\alpha_{olf}$ (SEQ ID NO: 21) activates the Gs transduction pathway that leads to an internal cAMP increase upon binding to the appropriate ligand. The results confirm the identity of Olfr740 (SEQ ID NO: 1 and SEQ ID NO: 2), Olfr743 (SEQ ID NO: 5 and SEQ ID NO: 6), and Olfr746 (SEQ ID NO: 37 and SEQ ID NO: 38) as indole-skatole receptors.

Example 5

Indole and Skatole Activity of Human OR52N2, OR11G2, OR5AC2, OR4C15, OR8S1, OR11H6, and OR11H4 and Mouse Olfr665 and Olfr740 in HEK293T Cells.

Figure 6A:
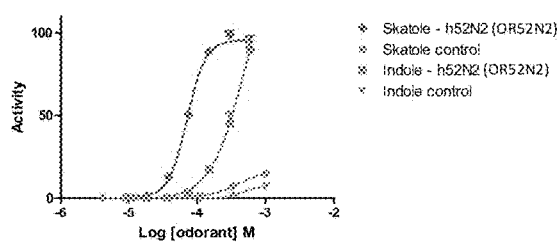
FIGS. 6A to 6J show the indole and skatole activity of human OR52N2, OR11G2, OR5AC2, OR4C15, OR8S1, OR11H6 and OR11H4 and mouse Olfr665 and Olfr740 in HEK293T cells.
Figure 6B:
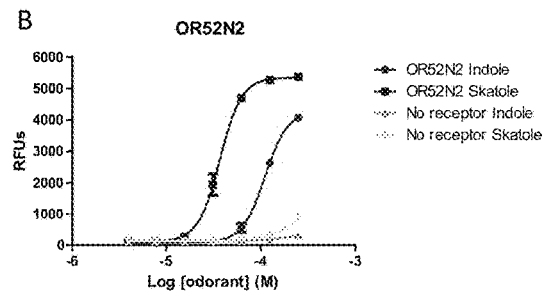
Figure 6C:
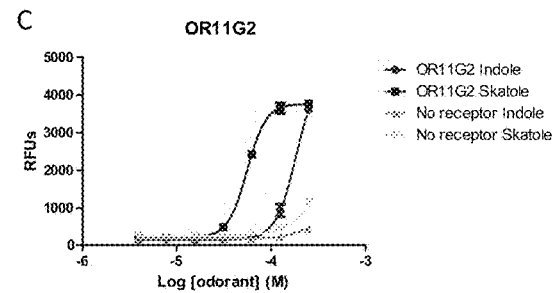
Figures 6D, 6E, 6F, 6G, 6H, 6I, 6J:
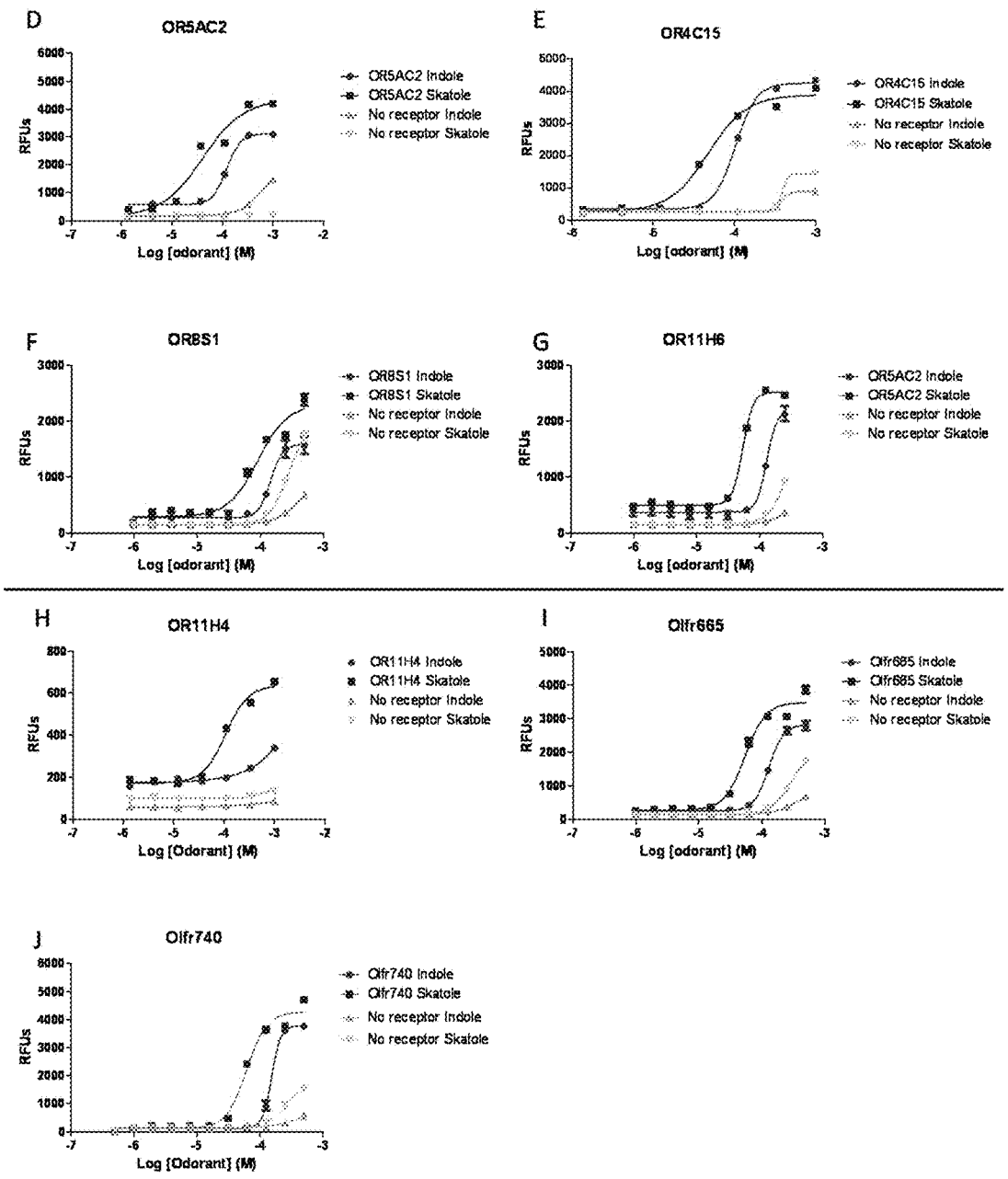

The activity of candidate human indole and skatole malodors receptors OR52N2 (SEQ ID NO: 11 and SEQ ID NO: 12), OR11G2 (SEQ ID NO: 13 and SEQ ID NO: 14), OR5AC2 (SEQ ID NO: 75 and SEQ ID NO: 76), OR4C15 (SEQ ID NO: 79 and SEQ ID NO: 80), OR8S1 (SEQ ID NO: 83 and SEQ ID NO: 84), OR11H6 (SEQ ID NO: 15 and SEQ ID NO: 16) and OR11H4 (SEQ ID NO: 49 and SEQ ID NO: 50) and candidate mouse indole and skatole malodors receptors Olfr665 (SEQ ID NO: 9 and SEQ ID NO 10) and Olfr740 (SEQ ID NO: 1 and SEQ ID NO 2) were confirmed in cell-based calcium-flux assays (FIGS. 6A to 6J). Cells stably co-expressing Rho-tagged human OR52N2 (FIG. 6A, B) or OR11G2 (FIG. 6C) and $G\alpha15$ (SEQ ID NO: 25) were exposed to increasing concentrations of skatole or indole. FIG. 6B is a repeat experiment showing similar activity of OR52N2 with indole and skatole. Odorant-induced OR52N2 or OR11G2 activity was detected by measuring the maximum Calcium 5 dye (Molecular Devices) fluorescence change following odorant exposure. Activity is defined as the baseline corrected Relative Fluorescent Units (RFU) ratios normalized to the highest RFU in the experiment in FIG. 6A. Relative Fluorescent Units is used to measure the receptor activity in FIGS. 6B-J. A dose-dependent increase of receptor activity was recorded and a corresponding dose-response curve is shown for both compounds. A cell line lacking a receptor, for example hOR52N2, was used as a control for non-specific activity at high concentrations ('Indole control' and 'Skatole control'). The human receptor OR52N2 (SEQ ID NO: 11 and SEQ ID NO: 12) was identified because of its sequence similarity to mouse Olfr665 (SEQ ID NO: 10), an indole/skatole receptor isolated from olfactory neurons responding to both indole and skatole. The human receptor OR11G2 (SEQ ID NO: 13 and SEQ ID NO: 14) was identified because of its sequence similarity to mouse Olfr740 (SEQ ID NO: 2), an indole/skatole receptor isolated from olfactory neurons responding to both indole and skatole. The receptors were modified with the Rho sequence and stably expressed in HEK 293T cells. Further examples show indole and skatole dose-response curves for human receptors OR5AC2, OR4C15, OR8S1, OR11H6, OR11H4 and mouse receptors Olfr665 and Olfr740 (FIG. 6D-J). The human receptor OR5AC2 (SEQ ID NO: 75 and SEQ ID NO: 76) was identified because of its sequence similarity to mouse Olfr207 (SEQ ID NO: 78), a receptor isolated from olfactory neurons responding to both indole and skatole. The human receptor OR4C15 (SEQ ID NO: 79 and SEQ ID NO: 80) was identified because of its sequence similarity to mouse Olfr211 (SEQ ID NO: 82), a receptor isolated from olfactory neurons responding to both indole and skatole. The human receptor OR8S1 (SEQ ID NO: 83 and SEQ ID NO: 84) was identified because of its sequence similarity to mouse Olfr257 (SEQ ID NO: 86), a receptor isolated from olfactory neurons responding to both indole and skatole. The human receptor OR11H6 (SEQ ID NO: 15 and SEQ ID NO: 16) was identified because of its sequence similarity to mouse Olfr745 (SEQ ID NO: 8), a receptor isolated from olfactory neurons responding to both indole and skatole. The human receptor OR11H4 (SEQ ID NO: 49 and SEQ ID NO: 50) was identified because of its sequence similarity to mouse Olfr746 (SEQ ID NO: 38), a receptor isolated from olfactory neurons responding to both indole and skatole. The mouse receptor Olfr665 (SEQ ID NO: 9 and SEQ ID NO: 10) was identified directly from NGS data from isolated olfactory neurons responding to both indole and skatole. The mouse receptor Olfr740 (SEQ ID NO: 1 and SEQ ID NO: 2) was identified directly from NGS data from isolated olfactory neurons responding to both indole and skatole. Co-expression of the human G alpha subunit $G\alpha15$ activates the Gq transduction pathway that leads to an internal Ca2+ increase upon binding to the appropriate ligand. These results serve to validate the process disclosed here is useful for the rapid and reliable identification of mammalian odorant receptors for malodor compounds.

Example 6

Inhibition of Indole Receptor Olfr743 Activity in HEK293T Cells.

Figure 7:
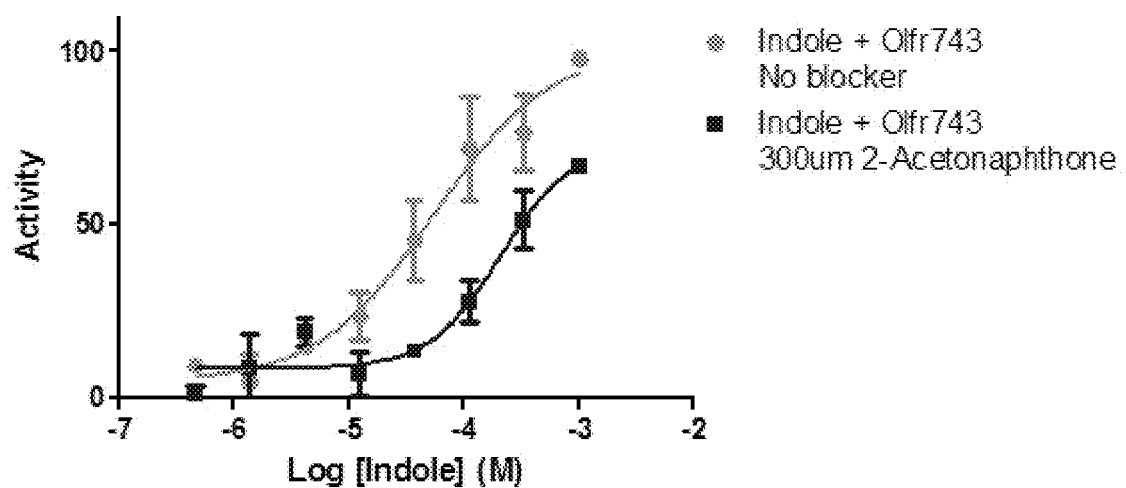
FIG. 7 shows the inhibition of indole receptor Olfr743 activity in HEK293T cells by a test compound.

Once identified using the procedure outlined herein, the resulting malodor receptor cell lines can be used to screen chemical libraries for compounds that modulate their activity and possibly human perception. This experiment was performed under the same conditions as in Example 4. Cells transfected with Rho-tagged (SEQ ID NO: 18) Olfr743 (SEQ ID NO: 6) were exposed to increasing concentrations of indole in the presence or absence of 300 μM 2-actetonaphthone. 2-acetonaphthone inhibits the activity of Olfr743 (SEQ ID NO: 6) to indole. The results are presented in Table 2 and FIG. 7. In the presence of the antagonist compound, a rightward shift of the dose-response curve is observed resulting in a 4 fold increase in the EC50 to indole. Activity is defined as the baseline corrected HTRF ratios normalized to the highest signal in the experiment. These results show that 2-acetonaphthone binds and inhibits the activity of the indole receptor.

TABLE 2

|  | Indole | Indole + 2-acetonaphthone 300 μM |
|---|---|---|
| EC50 | 54 μM | 206 μM |

What is claimed is:

1. A method for identifying a compound that blocks, inhibits, modulates, and/or enhances the activity of an olfactory receptor that is activated by indole and/or skatole comprising
   a) contacting a compound to at least one receptor, wherein the receptor is a polypeptide comprising an amino acid sequence having at least 90% sequence identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86;
   b) measuring the extent to which the compound blocks, inhibits, modulates, or enhances the activity of the receptor by measuring the response of the olfactory receptor in the presence and absence of the compound;
   c) identifying a compound that blocks, inhibits, modulates, or enhances the response of the olfactory receptor on the basis of the response that was measured in the presence and absence of the compound; and
   d) selecting the identified compound as a compound that blocks, inhibits, modulates, or enhances the response of the olfactory receptor.

2. The method of claim 1, wherein the polypeptide comprises an amino acid sequence having at least 95% sequence identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

3. The method of claim 1, wherein the polypeptide comprises an amino acid sequence having at least 98% sequence identity with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

4. The method of claim 1 wherein the polypeptide has the amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 28, SEQ ID NO: 30, SEQ ID NO: 32, SEQ ID NO: 34, SEQ ID NO: 36, SEQ ID NO: 38, SEQ ID NO: 40, SEQ Id NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO:

60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84 and SEQ ID NO: 86.

* * * * *

SEQUENCE LISTING

```
<160> NUMBER OF SEQ ID NOS: 86

<210> SEQ ID NO 1
<211> LENGTH: 936
<212> TYPE: DNA
<213> ORGANISM: Mus musculus

<400> SEQUENCE: 1
atgaaaacct tcagcagccc catcaactcc agcaccacca ctggcttcat tctcttgggc      60
ttcccctgcc ccagggaggg gcaaatcctc ctctttgtgc tcttctccat tgtctacctg     120
cttaccctca tgggcaacac ttgcatcatc tttgcagtat gctgggatca gagactccac     180
acacccatgt acctactgct ggccaacttc tccttcctgg agatctggta tgttacctcc     240
acagtcccca acatgttggc caatttcctc tctgacacca aggtcatctc tttctctgga     300
tgcttcctgc agttctattt cttcttctcc ttgggttcta cagaatgcct tttcctggca     360
gtcatggcat ttgatcgata ccttgccatc tgtaggccac tacattatcc tgctctcatg     420
actgggagcc tctgcaacat ccttgtgatc agttgctggg tgcttggttt cctctggttc     480
cctgttccca tcatcatcat ctcccagatg tccttctgtg ggtccagaat tatagaccac     540
ttcctgtgtg acccaggccc tctattggcc ctcacctgtt ccagagcccc attaatggag     600
gttttctgga caattataac atctcttatc ctgttcgttc ctttcctctt catcatggga     660
tcttatacat tggtcctgag agctgtgttc agagttcctt caagagatgg acaaaaaaag     720
gctttctcca cttgcggatc tcatctcaca gtagttttac tcttttatgg ctcagtgatg     780
ataatgtatc taagcccgac ctctgagcat gaagctggaa tgcagaagct tgtgactcta     840
ttttattctg tggttactcc actcattaat cctgtgatat acagtctgag gaacaaggat     900
atgaaacatg ccctgcagaa gatttaaga acataa                                936

<210> SEQ ID NO 2
<211> LENGTH: 311
<212> TYPE: PRT
<213> ORGANISM: Mus musculus

<400> SEQUENCE: 2

Met Lys Thr Phe Ser Ser Pro Ile Asn Ser Ser Thr Thr Thr Gly Phe
 1               5                  10                  15

Ile Leu Leu Gly Phe Pro Cys Pro Arg Glu Gly Gln Ile Leu Leu Phe
             20                  25                  30

Val Leu Phe Ser Ile Val Tyr Leu Leu Thr Leu Met Gly Asn Thr Cys
         35                  40                  45

Ile Ile Phe Ala Val Cys Trp Asp Gln Arg Leu His Thr Pro Met Tyr
```

```
                    50                  55                  60
Leu Leu Leu Ala Asn Phe Ser Phe Leu Glu Ile Trp Tyr Val Thr Ser
 65                  70                  75                  80

Thr Val Pro Asn Met Leu Ala Asn Phe Leu Ser Asp Thr Lys Val Ile
                 85                  90                  95

Ser Phe Ser Gly Cys Phe Leu Gln Phe Tyr Phe Phe Ser Leu Gly
            100                 105                 110

Ser Thr Glu Cys Leu Phe Leu Ala Val Met Ala Phe Asp Arg Tyr Leu
            115                 120                 125

Ala Ile Cys Arg Pro Leu His Tyr Pro Ala Leu Met Thr Gly Ser Leu
130                 135                 140

Cys Asn Ile Leu Val Ile Ser Cys Trp Val Leu Gly Phe Leu Trp Phe
145                 150                 155                 160

Pro Val Pro Ile Ile Ile Ser Gln Met Ser Phe Cys Gly Ser Arg
                165                 170                 175

Ile Ile Asp His Phe Leu Cys Asp Pro Gly Pro Leu Leu Ala Leu Thr
            180                 185                 190

Cys Ser Arg Ala Pro Leu Met Glu Val Phe Trp Thr Ile Ile Thr Ser
        195                 200                 205

Leu Ile Leu Phe Val Pro Phe Leu Phe Ile Met Gly Ser Tyr Thr Leu
210                 215                 220

Val Leu Arg Ala Val Phe Arg Val Pro Ser Arg Asp Gly Gln Lys Lys
225                 230                 235                 240

Ala Phe Ser Thr Cys Gly Ser His Leu Thr Val Val Leu Leu Phe Tyr
                245                 250                 255

Gly Ser Val Met Ile Met Tyr Leu Ser Pro Thr Ser Glu His Glu Ala
            260                 265                 270

Gly Met Gln Lys Leu Val Thr Leu Phe Tyr Ser Val Val Thr Pro Leu
        275                 280                 285

Ile Asn Pro Val Ile Tyr Ser Leu Arg Asn Lys Asp Met Lys His Ala
    290                 295                 300

Leu Gln Lys Ile Leu Arg Thr
305                 310

<210> SEQ ID NO 3
<211> LENGTH: 936
<212> TYPE: DNA
<213> ORGANISM: Mus musculus

<400> SEQUENCE: 3
atgaaaaccc tcagcagccc cagcaactcc agcaccatca ctggcttcat cctcttgggc      60
ttcgcctacc caggggaggg gcaaattctc ctctttgtga tcttcttcat tgtttacata     120
ctcattctta tgggcaacgc ttccatcatc tgtgctgtgt actgtgatca gagactccac     180 accccccatgt accttctgct ggccaacttc tccttcatgg agattggata tgtcacctcc     240
acagtcccca acatgttggc caacttcctt tcagacacca aggtcatctc tttctctgga     300
tgcttcctgc agttctattt cttcttctcc tttggttcta cagaatgctt tttcctggca     360
gtcatggcat tgatcgata ccttgccatc tgtaggccac tacattatcc ttctctcatg     420
actgggcgcc tccgaaacac ccttgtgacc agttgctggg tgcttggttt cctctggttc     480
cctgtaccca tcatcatcat ctcccagatg tccttctgtg ggtccagaat tatagaccac     540
ttcctgtgtg acccaggccc tcttttggcc cttgcctgtt ccagagtccc attgatagag     600
gttttctggt ccattataat gtctatgctc ctggttattc ctttcctctt catcatggga     660
```

```
acttacatat tggtcctaag agctgtgttt agacttcctt caagagaagg acaaaaaaag    720
gctttctcca cttgcgggtc tcatctcaca gtagtttcac tctttttattg ctcagtgatg    780 ataatgtatc tgagcccaac atctgagcat gaggccggaa tgcagaagct tgtaactcta    840 tttattctg tgggtacacc actgcttaat cctatgatat acagtctgag gaacaaagat    900
atgaaaaatg ccctacagaa gattttgaga acataa                              936
```

<210> SEQ ID NO 4
<211> LENGTH: 311
<212> TYPE: PRT
<213> ORGANISM: Mus musculus

<400> SEQUENCE: 4

```
Met Lys Thr Leu Ser Ser Pro Ser Asn Ser Thr Ile Thr Gly Phe
1               5                   10                  15

Ile Leu Leu Gly Phe Ala Tyr Pro Arg Glu Gly Gln Ile Leu Leu Phe
                20                  25                  30

Val Ile Phe Phe Ile Val Tyr Ile Leu Ile Leu Met Gly Asn Ala Ser
                35                  40                  45

Ile Ile Cys Ala Val Tyr Cys Asp Gln Arg Leu His Thr Pro Met Tyr
50                  55                  60

Leu Leu Leu Ala Asn Phe Ser Phe Met Glu Ile Gly Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Phe Gly
                100                 105                 110

Ser Thr Glu Cys Phe Phe Leu Ala Val Met Ala Phe Asp Arg Tyr Leu
                115                 120                 125

Ala Ile Cys Arg Pro Leu His Tyr Pro Ser Leu Met Thr Gly Arg Leu
130                 135                 140

Arg Asn Thr Leu Val Thr Ser Cys Trp Val Leu Gly Phe Leu Trp Phe
145                 150                 155                 160

Pro Val Pro Ile Ile Ile Ser Gln Met Ser Phe Cys Gly Ser Arg
                165                 170                 175

Ile Ile Asp His Phe Leu Cys Asp Pro Gly Pro Leu Leu Ala Leu Ala
                180                 185                 190

Cys Ser Arg Val Pro Leu Ile Glu Val Phe Trp Ser Ile Ile Met Ser
                195                 200                 205

Met Leu Leu Val Ile Pro Phe Leu Phe Ile Met Gly Thr Tyr Ile Leu
                210                 215                 220

Val Leu Arg Ala Val Phe Arg Leu Pro Ser Arg Glu Gly Gln Lys Lys
225                 230                 235                 240

Ala Phe Ser Thr Cys Gly Ser His Leu Thr Val Val Ser Leu Phe Tyr
                245                 250                 255

Cys Ser Val Met Ile Met Tyr Leu Ser Pro Thr Ser Glu His Glu Ala
                260                 265                 270

Gly Met Gln Lys Leu Val Thr Leu Phe Tyr Ser Val Gly Thr Pro Leu
                275                 280                 285

Leu Asn Pro Met Ile Tyr Ser Leu Arg Asn Lys Asp Met Lys Asn Ala
                290                 295                 300

Leu Gln Lys Ile Leu Arg Thr
305                 310
```

<210> SEQ ID NO 5
<211> LENGTH: 936
<212> TYPE: DNA
<213> ORGANISM: Mus musculus

<400> SEQUENCE: 5

| | | |
|---|---|---|
| atgaaaaccc tcagcagccc cagcaattcc agcaccatca caggcttcat ccttttgggc | 60 |
| ttccccctgcc ccagggaggg gcaaatcctt ctctttgtga tcttcttcgt tgtctaccta | 120 |
| ctcatcctca tgggcaacgc ttccatcatc tgtgctgtgt actgtgatca gagactccac | 180 |
| accccccatgt acctcctgct ggccaacttc tccttcctgg aaatctggta tgtcacttcc | 240 |
| acagtcccca acatgttggc caacttcctc tctgacaaca agatcatttc cttcgctgga | 300 |
| tgcttcctgc agttctattt cttcttctcc tttggttcta cagaatgctt tttcctggca | 360 |
| gtcatggcat ttgatcgata ccttgccatc tgtaggccac tacattatcc ttctctcatg | 420 |
| actaggcgcc tctgcaacat ccttgtgatc agttgctggg tgcttggttt cctctggttc | 480 |
| cctgtaccca tcatcatcat ctcccagatg tccttctgtg ggtccagaat tatagaccac | 540 |
| ttcctgtgtg acccaggtcc tcttttggcc cttgcctgtt ccagagcccc attgatggag | 600 |
| gttttctgga caattataat gtctattctc ctggttattc ctttcctctt catcatggga | 660 |
| tcttacatat tggtcctaag aactgtgttc agacttcctt caagagatgg acaaaaaaag | 720 |
| gccttctcca cctgtgggtc acatgtgact gtggtttctc ttttctatgg ctcagtgatg | 780 |
| ataatgtata tgagcccatc atctggacac gaagctggaa tgcagaagat tgtgactctg | 840 |
| ttttattctg tgggtactcc attacttaat cctgtgatat acagtctgag gaacaaagat | 900 |
| atgaaaaatg ccctgcaaaa gattttaaga acataa | 936 |

<210> SEQ ID NO 6
<211> LENGTH: 311
<212> TYPE: PRT
<213> ORGANISM: Mus musculus

<400> SEQUENCE: 6

Met Lys Thr Leu Ser Ser Pro Ser Asn Ser Thr Ile Thr Gly Phe
1               5                   10                  15

Ile Leu Leu Gly Phe Pro Cys Pro Arg Glu Gly Gln Ile Leu Leu Phe
            20                  25                  30

Val Ile Phe Phe Val Val Tyr Leu Leu Ile Leu Met Gly Asn Ala Ser
        35                  40                  45

Ile Ile Cys Ala Val Tyr Cys Asp Gln Arg Leu His Thr Pro Met Tyr
    50                  55                  60

Leu Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Asn Lys Ile Ile
                85                  90                  95

Ser Phe Ala Gly Cys Phe Leu Gln Phe Tyr Phe Phe Phe Ser Phe Gly
            100                 105                 110

Ser Thr Glu Cys Phe Phe Leu Ala Val Met Ala Phe Asp Arg Tyr Leu
        115                 120                 125

Ala Ile Cys Arg Pro Leu His Tyr Pro Ser Leu Met Thr Arg Arg Leu
    130                 135                 140

Cys Asn Ile Leu Val Ile Ser Cys Trp Val Leu Gly Phe Leu Trp Phe
145                 150                 155                 160

Pro Val Pro Ile Ile Ile Ile Ser Gln Met Ser Phe Cys Gly Ser Arg

```
                    165                 170                 175
Ile Ile Asp His Phe Leu Cys Asp Pro Gly Pro Leu Leu Ala Leu Ala
            180                 185                 190

Cys Ser Arg Ala Pro Leu Met Glu Val Phe Trp Thr Ile Ile Met Ser
            195                 200                 205

Ile Leu Leu Val Ile Pro Phe Leu Phe Ile Met Gly Ser Tyr Ile Leu
            210                 215                 220

Val Leu Arg Thr Val Phe Arg Leu Pro Ser Arg Asp Gly Gln Lys Lys
225                 230                 235                 240

Ala Phe Ser Thr Cys Gly Ser His Val Thr Val Val Ser Leu Phe Tyr
            245                 250                 255

Gly Ser Val Met Ile Met Tyr Met Ser Pro Ser Ser Gly His Glu Ala
            260                 265                 270

Gly Met Gln Lys Ile Val Thr Leu Phe Tyr Ser Val Gly Thr Pro Leu
            275                 280                 285

Leu Asn Pro Val Ile Tyr Ser Leu Arg Asn Lys Asp Met Lys Asn Ala
            290                 295                 300

Leu Gln Lys Ile Leu Arg Thr
305                 310

<210> SEQ ID NO 7
<211> LENGTH: 987
<212> TYPE: DNA
<213> ORGANISM: Mus musculus

<400> SEQUENCE: 7
atgatcactc atttctcagt tgtttctgtt tttctaacag ctttcggatc caagaacagc        60
tccatacatt ttgtgactga gtttatcctc ctgggtttca gtaaccaggg ggagatgcaa       120
agtttcttct tctgttcaat tctgattctt tacctcctga ccttgctggg gaatggaact       180
attgtttgtg ctgtgagatg ggatcagagg ctccacacac ccatgtacat cttcctggga       240
aactttgcct ttttagagat atggtatgtc tcttccacca tcccaaacat gttggtcaat       300
attctctctg agaataagac catctccttc tctgcctgct ccttcaatt ctatttcttt        360 ttttcacttg gtacaacaga gtgtttcttc ttgtcagcta tggcttatga tcgatacctg       420
gctatctgtc gaccattaca ctaccectct atcatgacta ggaagttctg tgtcatcctg       480
atttgtatct gctgggtgag tggattcctc tgctatccag tcccaattgt cctcatctcc       540
caacttcctt tctgtggtcc taacatcatt gaccactttg tgtgtgaccc aggaccattg       600
tttgcactat cctgtgtgcc tgctccttcc actgaacttc tctgttatac cttcaactca       660
atgattatct tgggcccctt cttctgcatc ctgggatcct atactctagt actcagagct       720
gtgtttcgag ttccttctgg tgctggtcga actaaagctt tctctacatg tggatctcat       780
ttagtggttg tgtctctgtt ctatggaact cttatggtga tgtatgtgag cccaacatca       840
gggaatcctg caggaatgca gaagattgtt actctgattt actcagcctt gacccccctc       900
ttaaatcctc tcatctatac tctccgaaac aaagaaatga aaaatgcctt aagagaaactg       960 ctaaaactaa caactatcca aaactga                                           987

<210> SEQ ID NO 8
<211> LENGTH: 328
<212> TYPE: PRT
<213> ORGANISM: Mus musculus

<400> SEQUENCE: 8
```

Met Ile Thr His Phe Ser Val Val Ser Val Phe Leu Thr Ala Phe Gly
1               5                   10                  15

Ser Lys Asn Ser Ser Ile His Phe Val Thr Glu Phe Ile Leu Leu Gly
            20                  25                  30

Phe Ser Asn Gln Gly Glu Met Gln Ser Phe Phe Cys Ser Ile Leu
        35                  40                  45

Ile Leu Tyr Leu Leu Thr Leu Leu Gly Asn Gly Thr Ile Val Cys Ala
50                  55                  60

Val Arg Trp Asp Gln Arg Leu His Thr Pro Met Tyr Ile Phe Leu Gly
65                  70                  75                  80

Asn Phe Ala Phe Leu Glu Ile Trp Tyr Val Ser Ser Thr Ile Pro Asn
                85                  90                  95

Met Leu Val Asn Ile Leu Ser Glu Asn Lys Thr Ile Ser Phe Ser Ala
            100                 105                 110

Cys Phe Leu Gln Phe Tyr Phe Phe Ser Leu Gly Thr Thr Glu Cys
        115                 120                 125

Phe Phe Leu Ser Ala Met Ala Tyr Asp Arg Tyr Leu Ala Ile Cys Arg
        130                 135                 140

Pro Leu His Tyr Pro Ser Ile Met Thr Arg Lys Phe Cys Val Ile Leu
145                 150                 155                 160

Ile Cys Ile Cys Trp Val Ser Gly Phe Leu Cys Tyr Pro Val Pro Ile
                165                 170                 175

Val Leu Ile Ser Gln Leu Pro Phe Cys Gly Pro Asn Ile Ile Asp His
            180                 185                 190

Phe Val Cys Asp Pro Gly Pro Leu Phe Ala Leu Ser Cys Val Pro Ala
        195                 200                 205

Pro Ser Thr Glu Leu Leu Cys Tyr Thr Phe Asn Ser Met Ile Ile Phe
210                 215                 220

Gly Pro Phe Phe Cys Ile Leu Gly Ser Tyr Thr Leu Val Leu Arg Ala
225                 230                 235                 240

Val Phe Arg Val Pro Ser Gly Ala Gly Arg Thr Lys Ala Phe Ser Thr
                245                 250                 255

Cys Gly Ser His Leu Val Val Val Ser Leu Phe Tyr Gly Thr Leu Met
            260                 265                 270

Val Met Tyr Val Ser Pro Thr Ser Gly Asn Pro Ala Gly Met Gln Lys
        275                 280                 285

Ile Val Thr Leu Ile Tyr Ser Ala Leu Thr Pro Leu Leu Asn Pro Leu
        290                 295                 300

Ile Tyr Thr Leu Arg Asn Lys Glu Met Lys Asn Ala Leu Lys Lys Leu
305                 310                 315                 320

Leu Lys Leu Thr Thr Ile Gln Asn
                325

<210> SEQ ID NO 9
<211> LENGTH: 951
<212> TYPE: DNA
<213> ORGANISM: Mus musculus

<400> SEQUENCE: 9
atgcctgggg tcaataccte cagcctgaca ccaagatact ttattctcaa tgggattcct    60
gggttggaag ctgcacacat ctggatctct ctgccattct tcattatgta cctcattgct   120
gtcacaggta actgtggact tatctacctc atcagtcatg aggaggctct gcaccggccc   180
atgtactact ttctagccat gttgtctgct acagatattt ctgggtgtaa tacaattgtc   240

```
cccagtatgt tatgcatctt ttggttcagt gtcaaggaga ttgatttcaa tgcctgcctt    300
gtacagatgt ttttcatcca catgttaaca ggcatggagt ctggtgtgct catgcttatg    360
gctctcgacc gctatgtggc tatatgctat ccattacgct atactaccat actcaccaac    420
actatgatta ccaagattgg attggcagca cttgttagaa gtgtgttact catggtccct    480
tttgctttcc tgatcaagcg tcttccatac tgtagaggaa acctcatcca acatacctat    540
tgtgatcaca tggctgtggc taaactatcc tgtggcaata ttaagattaa tgctatctat    600
ggtcttataa ttgctatatt tattgggggt tttgatatat tctgtatctc catgtcttat    660
gccatgatta tccatgctgt ggtgaagcta tcttcggcag atgctcgcca taaagccttc    720
agtacctgta catcacacat atgtgctatt gttattacct atgtcccagc attcttcaac    780
ttctttactc atcgctttgg gagaaccact atacccatc atatccacat tattatagcc    840
aacctgtatc tattgctacc tcccaccttg aatccaattg tatatggagt aaagaccaag    900
cagattcgtg aaggtgtgat caaactgttt gctagacaaa aagttgtttg a             951
```

```
<210> SEQ ID NO 10
<211> LENGTH: 316
<212> TYPE: PRT
<213> ORGANISM: Mus musculus

<400> SEQUENCE: 10

Met Pro Gly Val Asn Thr Ser Ser Leu Thr Pro Arg Tyr Phe Ile Leu
1               5                   10                  15

Asn Gly Ile Pro Gly Leu Glu Ala Ala His Ile Trp Ile Ser Leu Pro
            20                  25                  30

Phe Phe Ile Met Tyr Leu Ile Ala Val Thr Gly Asn Cys Gly Leu Ile
        35                  40                  45

Tyr Leu Ile Ser His Glu Glu Ala Leu His Arg Pro Met Tyr Tyr Phe
    50                  55                  60

Leu Ala Met Leu Ser Ala Thr Asp Ile Ser Gly Cys Asn Thr Ile Val
65                  70                  75                  80

Pro Ser Met Leu Cys Ile Phe Trp Phe Ser Val Lys Glu Ile Asp Phe
                85                  90                  95

Asn Ala Cys Leu Val Gln Met Phe Phe Ile His Met Leu Thr Gly Met
            100                 105                 110

Glu Ser Gly Val Leu Met Leu Met Ala Leu Asp Arg Tyr Val Ala Ile
        115                 120                 125

Cys Tyr Pro Leu Arg Tyr Thr Thr Ile Leu Thr Asn Thr Met Ile Thr
    130                 135                 140

Lys Ile Gly Leu Ala Ala Leu Val Arg Ser Val Leu Leu Met Val Pro
145                 150                 155                 160

Phe Ala Phe Leu Ile Lys Arg Leu Pro Tyr Cys Arg Gly Asn Leu Ile
                165                 170                 175

Gln His Thr Tyr Cys Asp His Met Ala Val Ala Lys Leu Ser Cys Gly
            180                 185                 190

Asn Ile Lys Ile Asn Ala Ile Tyr Gly Leu Ile Ile Ala Ile Phe Ile
        195                 200                 205

Gly Gly Phe Asp Ile Phe Cys Ile Ser Met Ser Tyr Ala Met Ile Ile
    210                 215                 220

His Ala Val Val Lys Leu Ser Ser Ala Asp Ala Arg His Lys Ala Phe
225                 230                 235                 240

Ser Thr Cys Thr Ser His Ile Cys Ala Ile Val Ile Thr Tyr Val Pro
                245                 250                 255
```

Ala Phe Phe Asn Phe Phe Thr His Arg Phe Gly Arg Thr Thr Ile Pro
                260                 265                 270

His His Ile His Ile Ile Ile Ala Asn Leu Tyr Leu Leu Pro Pro
            275                 280                 285

Thr Leu Asn Pro Ile Val Tyr Gly Val Lys Thr Lys Gln Ile Arg Glu
        290                 295                 300

Gly Val Ile Lys Leu Phe Ala Arg Gln Lys Val Val
305                 310                 315

<210> SEQ ID NO 11
<211> LENGTH: 966
<212> TYPE: DNA
<213> ORGANISM: Homo Sapiens

<400> SEQUENCE: 11

```
atgtctgggg acaacagctc cagcctgacc ccaggattct ttatcttgaa tggcgttcct      60
gggctggaag ccacacacat ctggatctcc ctgccattct gctttatgta catcattgct    120
gtcgtgggga actgtgggct catctgcctc atcagccatg aggaggccct gcaccggccc    180
atgtactact tcctggccct gctctccttc actgatgtca ccttgtgcac caccatggta    240
cctaatatgc tgtgcatatt ctggttcaac ctcaaggaga ttgactttaa cgcctgcctg    300
gcccagatgt tttttgtcca tatgctgaca gggatggagt ctggggtgct catgctcatg    360
gccctggacc gctatgtggc catctgctac cccttacgct atgccaccat ccttaccaac    420
cctgtcatcg ccaaggctgg tcttgccacc ttcttgagga atgtgatgct catcatccca    480
ttcactctcc tcaccaagcg cctgccctat tgccggggga acttcatccc ccacacctac    540
tgtgaccata tgtctgtggc caaggtatcc tgtggcaatt tcaaggtcaa tgctatttat    600
ggtctgatgg ttgctctcct gattggtgtg tttgatatct gctgtatctc tgtatcttac    660
actatgattt tgcaggctgt tatgagcctg tcatcagcag atgctcgtca caaagccttc    720
agcacctgca catctcacat gtgttccatt gtgatcacct atgttgctgc tttttttcact    780
tttttcactc atcgtttgt aggacacaat atcccaaacc acatacacat catcgtggcc    840
aacctttatc tgctactgcc tcctaccatg aacccaattg tttatggagt caagaccaag    900
cagattcagg aaggtgtaat taaatttta cttggagaca aggttagttt tacctatgac    960
aaatga                                                              966
```

<210> SEQ ID NO 12
<211> LENGTH: 321
<212> TYPE: PRT
<213> ORGANISM: Homo Sapiens

<400> SEQUENCE: 12

Met Ser Gly Asp Asn Ser Ser Ser Leu Thr Pro Gly Phe Phe Ile Leu
1               5                   10                  15

Asn Gly Val Pro Gly Leu Glu Ala Thr His Ile Trp Ile Ser Leu Pro
            20                  25                  30

Phe Cys Phe Met Tyr Ile Ile Ala Val Val Gly Asn Cys Gly Leu Ile
        35                  40                  45

Cys Leu Ile Ser His Glu Glu Ala Leu His Arg Pro Met Tyr Tyr Phe
    50                  55                  60

Leu Ala Leu Leu Ser Phe Thr Asp Val Thr Leu Cys Thr Thr Met Val
65                  70                  75                  80

Pro Asn Met Leu Cys Ile Phe Trp Phe Asn Leu Lys Glu Ile Asp Phe

```
                    85                  90                  95
Asn Ala Cys Leu Ala Gln Met Phe Phe Val His Met Leu Thr Gly Met
                100                 105                 110
Glu Ser Gly Val Leu Met Leu Met Ala Leu Asp Arg Tyr Val Ala Ile
                115                 120                 125
Cys Tyr Pro Leu Arg Tyr Ala Thr Ile Leu Thr Asn Pro Val Ile Ala
            130                 135                 140
Lys Ala Gly Leu Ala Thr Phe Leu Arg Asn Val Met Leu Ile Ile Pro
145                 150                 155                 160
Phe Thr Leu Leu Thr Lys Arg Leu Pro Tyr Cys Arg Gly Asn Phe Ile
                165                 170                 175
Pro His Thr Tyr Cys Asp His Met Ser Val Ala Lys Val Ser Cys Gly
            180                 185                 190
Asn Phe Lys Val Asn Ala Ile Tyr Gly Leu Met Val Ala Leu Leu Ile
            195                 200                 205
Gly Val Phe Asp Ile Cys Cys Ile Ser Val Ser Tyr Thr Met Ile Leu
            210                 215                 220
Gln Ala Val Met Ser Leu Ser Ser Ala Asp Ala Arg His Lys Ala Phe
225                 230                 235                 240
Ser Thr Cys Thr Ser His Met Cys Ser Ile Val Ile Thr Tyr Val Ala
                245                 250                 255
Ala Phe Pro Thr Phe Pro Thr His Arg Phe Val Gly His Asn Ile Pro
                260                 265                 270
Asn His Ile His Ile Val Ala Asn Leu Tyr Leu Leu Pro Pro
            275                 280                 285
Thr Met Asn Pro Ile Val Tyr Gly Val Lys Thr Lys Gln Ile Gln Glu
            290                 295                 300
Gly Val Ile Lys Phe Leu Leu Gly Asp Lys Val Ser Phe Thr Tyr Asp
305                 310                 315                 320
Lys

<210> SEQ ID NO 13
<211> LENGTH: 936
<212> TYPE: DNA
<213> ORGANISM: Homo Sapiens

<400> SEQUENCE: 13
atgaaaatct tcaacagccc cagcaactcc agcaccttca ctggcttcat cctcctgggc     60
ttcccttgcc ccagggaggg gcagatcctc ctctttgtgc tcttcactgt tgtttacctc    120
ctgaccctca tgggcaatgg ttccatcatc tgtgctgtgc actgggatca gagactccac    180
gcccccatgt acatcctgct cgccaacttc tccttcttgg agatatgtta tgtcacctcc    240
acagtcccca gcatgctggc caacttcctc tctgacacca gatcatctc gttctctggc    300
tgcttcctcc agttctactt tttcttctcc ttgggctcta cagaatgctt tttcctggca    360
gttatggcat tgatcgata ccttgccatc tgtcggcctc tacgctatcc aaccattatg    420
accagacgtc tctgtaccaa tcttgtggtc aattgctggg tacttggttt catctggttc    480
ttgattccta tcgtcaacat ctcccaaatg tccttctgtg gatctaggat tattgaccac    540
ttcctatgtg acccagctcc tcttctaact ctcacttgca aaaaggccc  tgtgatagag    600
cttgtctttt ctgtcttaag tcctctgcct gtctttatgc tctttctctt cattgtgggg    660
tcctatgctc tggtcgtgag agctgtgttg agggtcccctt cagcagctgg gagaagaaag    720
gctttctcca cctgtgggtc tcacctggct gtggtttcac tgttctacgg ctcagtactg    780
```
gtcatgtatg ggagcccacc atctaagaat gaagctggaa agcagaagac tgtgactctg    840 tttattctg ttgttacccc actgcttaac cctgtgatat atagtcttag gaacaaagat    900
atgagaaaag ctctgaagaa attttgggga acataa                              936

```
<210> SEQ ID NO 14
<211> LENGTH: 311
<212> TYPE: PRT
<213> ORGANISM: Homo Sapiens

<400> SEQUENCE: 14
```

Met Lys Ile Phe Asn Ser Pro Ser Asn Ser Thr Phe Thr Gly Phe
1               5                   10                  15

Ile Leu Leu Gly Phe Pro Cys Pro Arg Glu Gly Gln Ile Leu Leu Phe
            20                  25                  30

Val Leu Phe Thr Val Val Tyr Leu Thr Leu Met Gly Asn Gly Ser
        35                  40                  45

Ile Ile Cys Ala Val His Trp Asp Gln Arg Leu His Ala Pro Met Tyr
        50                  55                  60

Ile Leu Leu Ala Asn Phe Ser Phe Leu Glu Ile Cys Tyr Val Thr Ser
65                  70                  75                  80

Thr Val Pro Ser Met Leu Ala Asn Phe Leu Ser Asp Thr Lys Ile Ile
                85                  90                  95

Ser Phe Ser Gly Cys Phe Leu Gln Phe Tyr Phe Phe Ser Leu Gly
            100                 105                 110

Ser Thr Glu Cys Phe Phe Leu Ala Val Met Ala Phe Asp Arg Tyr Leu
            115                 120                 125

Ala Ile Cys Arg Pro Leu Arg Tyr Pro Thr Ile Met Thr Arg Arg Leu
        130                 135                 140

Cys Thr Asn Leu Val Val Asn Cys Trp Val Leu Gly Phe Ile Trp Phe
145                 150                 155                 160

Leu Ile Pro Ile Val Asn Ile Ser Gln Met Ser Phe Cys Gly Ser Arg
                165                 170                 175

Ile Ile Asp His Phe Leu Cys Asp Pro Ala Pro Leu Leu Thr Leu Thr
            180                 185                 190

Cys Lys Lys Gly Pro Val Ile Glu Leu Val Phe Ser Val Leu Ser Pro
        195                 200                 205

Leu Pro Val Phe Met Leu Phe Leu Phe Ile Val Gly Ser Tyr Ala Leu
        210                 215                 220

Val Val Arg Ala Val Leu Arg Val Pro Ser Ala Ala Gly Arg Arg Lys
225                 230                 235                 240

Ala Phe Ser Thr Cys Gly Ser His Leu Ala Val Val Ser Leu Phe Tyr
                245                 250                 255

Gly Ser Val Leu Val Met Tyr Gly Ser Pro Pro Ser Lys Asn Glu Ala
            260                 265                 270

Gly Lys Gln Lys Thr Val Thr Leu Phe Tyr Ser Val Val Thr Pro Leu
        275                 280                 285

Leu Asn Pro Val Ile Tyr Ser Leu Arg Asn Lys Asp Met Arg Lys Ala
        290                 295                 300

Leu Lys Lys Phe Trp Gly Thr
305                 310

```
<210> SEQ ID NO 15
<211> LENGTH: 993
<212> TYPE: DNA
```

<213> ORGANISM: Homo Sapiens

<400> SEQUENCE: 15

```
atgttcttta ttattcattc tttggttact tctgttttc taacagcttt gggaccccag      60
aacagaacaa tgcattttgt gactgagttt gtcctcctgg gtttccatgg tcaaagggag    120
atgcagagct gcttcttctc attcatcctg gttctctatc tcctgacact gctagggaat    180
ggagctattg tctgtgcagt gaaattggac aggcggctcc acacacccat gtacatcctt    240
ctgggaaact ttgcctttct agagatctgg tacatttcct ccactgtccc aaacatgcta    300
gtcaatatcc tctctgagat aaaaccatc tccttctctg ttgcttcct gcaattctat      360
ttcttttttt cactgggtac aacagagtgt ttcttttat cagttatggc ttatgatcgg     420
tacctggcca tctgtcgtcc attacactac ccctccatca tgactgggaa gttctgtata    480
attctggtct gtgtatgctg ggtaggcgga tttctctgct atccagtccc tattgttctt    540
atctcccaac ttcccttctg tgggcccaac atcattgacc acttggtgtg tgacccaggc    600
ccattgtttg cactggcctg catctctgct ccttccactg agcttatctg ttacaccttc    660
aactcgatga ttatctttgg gcccttcctc tccatcttgg gatcttacac tctggtcatc    720
agagctgtgc tttgtattcc ctctggtgct ggtcgaacta aagctttctc cacatgtggg    780
tcccacctaa tggtggtgtc tctattctat ggaacccta tggtgatgta tgtgagccca    840
acatcaggga acccagcagg aatgcagaag atcatcactc tggtatacac agcaatgact    900
ccattcttaa atccccttat ctatagtctt cgaaacaaag acatgaaaga tgctctaaag    960
agagtcctgg ggttaacagt tagccaaaac tga                                 993
```

<210> SEQ ID NO 16  
<211> LENGTH: 330  
<212> TYPE: PRT  
<213> ORGANISM: Homo Sapiens

<400> SEQUENCE: 16

```
Met Phe Phe Ile Ile His Ser Leu Val Thr Ser Val Phe Leu Thr Ala
1               5                   10                  15

Leu Gly Pro Gln Asn Arg Thr Met His Phe Val Thr Glu Phe Val Leu
            20                  25                  30

Leu Gly Phe His Gly Gln Arg Glu Met Gln Ser Cys Phe Phe Ser Phe
        35                  40                  45

Ile Leu Val Leu Tyr Leu Leu Thr Leu Leu Gly Asn Gly Ala Ile Val
    50                  55                  60

Cys Ala Val Lys Leu Asp Arg Arg Leu His Thr Pro Met Tyr Ile Leu
65                  70                  75                  80

Leu Gly Asn Phe Ala Phe Leu Glu Ile Trp Tyr Ile Ser Ser Thr Val
                85                  90                  95

Pro Asn Met Leu Val Asn Ile Leu Ser Glu Ile Lys Thr Ile Ser Phe
            100                 105                 110

Ser Gly Cys Phe Leu Gln Phe Tyr Phe Phe Ser Leu Gly Thr Thr
        115                 120                 125

Glu Cys Phe Phe Leu Ser Val Met Ala Tyr Asp Arg Tyr Leu Ala Ile
    130                 135                 140

Cys Arg Pro Leu His Tyr Pro Ser Ile Met Thr Gly Lys Phe Cys Ile
145                 150                 155                 160

Ile Leu Val Cys Val Cys Trp Val Gly Gly Phe Leu Cys Tyr Pro Val
                165                 170                 175
```

```
Pro Ile Val Leu Ile Ser Gln Leu Pro Phe Cys Gly Pro Asn Ile Ile
                180                 185                 190
Asp His Leu Val Cys Asp Pro Gly Pro Leu Phe Ala Leu Ala Cys Ile
            195                 200                 205
Ser Ala Pro Ser Thr Glu Leu Ile Cys Tyr Thr Phe Asn Ser Met Ile
        210                 215                 220
Ile Phe Gly Pro Phe Leu Ser Ile Leu Gly Ser Tyr Thr Leu Val Ile
225                 230                 235                 240
Arg Ala Val Leu Cys Ile Pro Ser Gly Ala Gly Arg Thr Lys Ala Phe
                245                 250                 255
Ser Thr Cys Gly Ser His Leu Met Val Val Ser Leu Phe Tyr Gly Thr
            260                 265                 270
Leu Met Val Met Tyr Val Ser Pro Thr Ser Gly Asn Pro Ala Gly Met
        275                 280                 285
Gln Lys Ile Ile Thr Leu Val Tyr Thr Ala Met Thr Pro Phe Leu Asn
        290                 295                 300
Pro Leu Ile Tyr Ser Leu Arg Asn Lys Asp Met Lys Asp Ala Leu Lys
305                 310                 315                 320
Arg Val Leu Gly Leu Thr Val Ser Gln Asn
                325                 330

<210> SEQ ID NO 17
<211> LENGTH: 96
<212> TYPE: DNA
<213> ORGANISM: Artificial Sequence
<220> FEATURE:
<223> OTHER INFORMATION: Synthetic Sequence

<400> SEQUENCE: 17
atggattaca aggacgacga cgataagatc gaattgatga acgggaccga gggcccaaac      60
ttctacgtgc ctttctccaa caagacgggc gtggtg                               96

<210> SEQ ID NO 18
<211> LENGTH: 32
<212> TYPE: PRT
<213> ORGANISM: Articifical Sequence
<220> FEATURE:
<223> OTHER INFORMATION: Synthetic Peptide

<400> SEQUENCE: 18

Met Asp Tyr Lys Asp Asp Asp Lys Ile Glu Leu Met Asn Gly Thr
1               5                   10                  15
Glu Gly Pro Asn Phe Tyr Val Pro Phe Ser Asn Lys Thr Gly Val Val
                20                  25                  30

<210> SEQ ID NO 19
<211> LENGTH: 1146
<212> TYPE: DNA
<213> ORGANISM: Mus musculus

<400> SEQUENCE: 19 atgggggtgtt tgggcaacag cagcaagacc gcggaagatc agggcgtaga tgaaaaagaa      60
cgccgcgagg ccaacaaaaa gatcgagaag cagttgcaga agagcgcct ggcttacaaa      120 gcaactcacc gcctgctgct tctgggggct ggtgagtccg ggaaaagcac tatcgtcaaa      180
cagatgagga tcctgcacgt caatggcttc aaccccgagg aaaagaagca gaaaattctg      240
gacatcagga aaaatgtcaa agatgcgatc gtgacaatcg tttcagcaat gagtactatc      300
atacctccag ttccactggc caaccctgag aaccagttcc ggtcagatta tatcaagagc      360
```

```
atagcccta tcactgactt tgaatattcc caggagttct ttgaccatgt gaagaagctg    420
tgggacgatg aaggagtgaa ggcctgcttt gagagatcca acgagtacca gctgatcgac    480
tgtgcacaat acttcctgga aaggattgac agtgtcagtc tggttgacta cacacccaca    540
gaccaggacc tgctcagatg cagagtgctg acatcaggaa tctttgagac acgattccaa    600
gtggacaaag tgaactttca catgtttgat gttggaggcc agagagatga gagaagaaaa    660
tggatccagt gttttaatga tgtcactgcg atcatttacg tggcggcctg tagtagctac    720
aacatggtga tccgggaaga taacaatacc aacagacttc gggaatcact ggacctgttt    780
gaaagcatct ggaataacag gtggttgcga accatttcta tcatcctatt cttgaacaaa    840
caagacatgc tggcagaaaa agtcttggca gggaagtcaa aaatcgaaga ctatttcccg    900
gagtatgcca attatactgt ccctgaagat gcaacaccag atgcgggaga agatcccaaa    960
gttacaagag caaagttctt tatccgggat ctgttcttga ggatcagcac agccacgggt   1020
gatggcaaac attactgcta ccctcacttc acctgcgccg tggacacaga aacatccgc   1080
agagtgttca acgattgccg tgacatcatc cagagaatgc atctcaagca gtacgaactc   1140
ttgtga                                                             1146

<210> SEQ ID NO 20
<211> LENGTH: 381
<212> TYPE: PRT
<213> ORGANISM: Mus musculus

<400> SEQUENCE: 20

Met Gly Cys Leu Gly Asn Ser Ser Lys Thr Ala Glu Asp Gln Gly Val
  1               5                  10                  15

Asp Glu Lys Glu Arg Arg Glu Ala Asn Lys Lys Ile Glu Lys Gln Leu
                 20                  25                  30

Gln Lys Glu Arg Leu Ala Tyr Lys Ala Thr His Arg Leu Leu Leu Leu
             35                  40                  45

Gly Ala Gly Glu Ser Gly Lys Ser Thr Ile Val Lys Gln Met Arg Ile
         50                  55                  60

Leu His Val Asn Gly Phe Asn Pro Glu Glu Lys Lys Gln Lys Ile Leu
 65                  70                  75                  80

Asp Ile Arg Lys Asn Val Lys Asp Ala Ile Val Thr Ile Val Ser Ala
                 85                  90                  95

Met Ser Thr Ile Ile Pro Pro Val Pro Leu Ala Asn Pro Glu Asn Gln
                100                 105                 110

Phe Arg Ser Asp Tyr Ile Lys Ser Ile Ala Pro Ile Thr Asp Phe Glu
            115                 120                 125

Tyr Ser Gln Glu Phe Phe Asp His Val Lys Lys Leu Trp Asp Asp Glu
        130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220
```

Phe Asn Asp Val Thr Ala Ile Ile Tyr Val Ala Ala Cys Ser Ser Tyr
225                 230                 235                 240

Asn Met Val Ile Arg Glu Asp Asn Asn Thr Asn Arg Leu Arg Glu Ser
            245                 250                 255

Leu Asp Leu Phe Glu Ser Ile Trp Asn Asn Arg Trp Leu Arg Thr Ile
        260                 265                 270

Ser Ile Ile Leu Phe Leu Asn Lys Gln Asp Met Leu Ala Glu Lys Val
    275                 280                 285

Leu Ala Gly Lys Ser Lys Ile Glu Asp Tyr Phe Pro Glu Tyr Ala Asn
290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
                325                 330                 335

Thr Ala Thr Gly Asp Gly Lys His Tyr Cys Tyr Pro His Phe Thr Cys
            340                 345                 350

Ala Val Asp Thr Glu Asn Ile Arg Arg Val Phe Asn Asp Cys Arg Asp
        355                 360                 365

Ile Ile Gln Arg Met His Leu Lys Gln Tyr Glu Leu Leu
    370                 375                 380

<210> SEQ ID NO 21
<211> LENGTH: 1377
<212> TYPE: DNA
<213> ORGANISM: Homo Sapiens

<400> SEQUENCE: 21
atgggtctgt gctacagtct gcggccgctg cttttcgggg gcccagggga cgacccctgc      60
gcggcctcgg agccgccggt ggaggacgcg cagcccgccc ggccccggc cctggcccca     120 gtccgggcgg ccgcaaggga cacggcccgg accctgctcc ctcggggcgg cgaagggagc     180
ccggcatgcg ctcggcccaa agcagacaag ccgaaggaga gcggcagcg caccgagcag     240 cttagtgccg aggagcgcga ggcggccaag gagcgcgagg cggtcaagga ggcgaggaaa     300
gtgagccggg gcatcgaccg catgctgcgc gaccagaagc gcgacctgca gcagacgcac     360
cggctcctgc tgctcggggc tggtgagtct gggaaaagca ctatcgtcaa acagatgagg     420
atcctgcacg tcaatgggtt taatcccgag gaaaagaaac agaaaattct ggacatccgg     480
aaaaatgtta aagatgctat cgtgacaatt gtttcagcaa tgagtactat aatacctcca     540
gttccgctgg ccaaccctga aaccaatttt cgatcagact acatcaagag catagccct     600 atcactgact ttgaatattc ccaggaattc tttgaccatg tgaaaaaact ttgggacgat     660
gaaggcgtga aggcatgctt tgagagatcc aacgaatacc agctgattga ctgtgcacaa     720
tacttcctgg aaagaatcga cagcgtcagc ttggttgact acacaccac agaccaggac     780 ctcctcagat gcagagttct gacatctggg attttgaga cacgattcca agtggacaaa     840
gtaaacttcc acatgtttga tgttggtggc cagagggatg agaggagaaa atggatccag     900
tgctttaacg atgtcacagc tatcatttac gtcgcagcct gcagtagcta caacatggtg     960
attcgagaag ataacaacac caacaggctg agagagtccc tggatctttt tgaaagcatc    1020
tggaacaaca ggtggttacg gaccatttct atcatcttgt tcttgaacaa acaagatatg    1080
ctggcagaaa aagtcttggc agggaaatca aaaattgaag actatttccc agaatatgca    1140
aattatactg ttcctgaaga cgcaacacca gatgcaggag aagatcccaa agttacaaga    1200
gccaagttct ttatccggga cctgtttttg aggatcagca cggccaccgg tgacggcaaa    1260

```
cattactgct accogcactt cacctgcgcc gtggacacag agaacatccg cagggtgttc    1320
aacgactgcc gcgacatcat ccagcggatg cacctcaagc agtatgagct cttgtga      1377
```

<210> SEQ ID NO 22
<211> LENGTH: 458
<212> TYPE: PRT
<213> ORGANISM: Homo Sapiens

<400> SEQUENCE: 22

```
Met Gly Leu Cys Tyr Ser Leu Arg Pro Leu Phe Gly Gly Pro Gly
1               5                   10                  15

Asp Asp Pro Cys Ala Ala Ser Glu Pro Val Glu Asp Ala Gln Pro
            20                  25                  30

Ala Pro Ala Pro Ala Leu Ala Pro Val Arg Ala Ala Arg Asp Thr
        35                  40                  45

Ala Arg Thr Leu Leu Pro Arg Gly Gly Glu Gly Ser Pro Ala Cys Ala
    50                  55                  60

Arg Pro Lys Ala Asp Lys Pro Lys Glu Lys Arg Gln Arg Thr Glu Gln
65                  70                  75                  80

Leu Ser Ala Glu Glu Arg Glu Ala Ala Lys Glu Arg Glu Ala Val Lys
                85                  90                  95

Glu Ala Arg Lys Val Ser Arg Gly Ile Asp Arg Met Leu Arg Asp Gln
            100                 105                 110

Lys Arg Asp Leu Gln Gln Thr His Arg Leu Leu Leu Gly Ala Gly
        115                 120                 125

Glu Ser Gly Lys Ser Thr Ile Val Lys Gln Met Arg Ile Leu His Val
130                 135                 140

Asn Gly Phe Asn Pro Glu Glu Lys Lys Gln Lys Ile Leu Asp Ile Arg
145                 150                 155                 160

Lys Asn Val Lys Asp Ala Ile Val Thr Ile Val Ser Ala Met Ser Thr
                165                 170                 175

Ile Ile Pro Pro Val Pro Leu Ala Asn Pro Glu Asn Gln Phe Arg Ser
            180                 185                 190

Asp Tyr Ile Lys Ser Ile Ala Pro Ile Thr Asp Phe Glu Tyr Ser Gln
        195                 200                 205

Glu Phe Phe Asp His Val Lys Lys Leu Trp Asp Asp Glu Gly Val Lys
    210                 215                 220

Ala Cys Phe Glu Arg Ser Asn Glu Tyr Gln Leu Ile Asp Cys Ala Gln
225                 230                 235                 240

Tyr Phe Leu Glu Arg Ile Asp Ser Val Ser Leu Val Asp Tyr Thr Pro
                245                 250                 255

Thr Asp Gln Asp Leu Leu Arg Cys Arg Val Leu Thr Ser Gly Ile Phe
            260                 265                 270

Glu Thr Arg Phe Gln Val Asp Lys Val Asn Phe His Met Phe Asp Val
        275                 280                 285

Gly Gly Gln Arg Asp Glu Arg Arg Lys Trp Ile Gln Cys Phe Asn Asp
    290                 295                 300

Val Thr Ala Ile Ile Tyr Val Ala Ala Cys Ser Ser Tyr Asn Met Val
305                 310                 315                 320

Ile Arg Glu Asp Asn Asn Thr Asn Arg Leu Arg Glu Ser Leu Asp Leu
                325                 330                 335

Phe Glu Ser Ile Trp Asn Asn Arg Trp Leu Arg Thr Ile Ser Ile Ile
            340                 345                 350
```

Leu Phe Leu Asn Lys Gln Asp Met Leu Ala Glu Lys Val Leu Ala Gly
355                 360                 365

Lys Ser Lys Ile Glu Asp Tyr Phe Pro Glu Tyr Ala Asn Tyr Thr Val
    370                 375                 380

Pro Glu Asp Ala Thr Pro Asp Ala Gly Glu Asp Pro Lys Val Thr Arg
385                 390                 395                 400

Ala Lys Phe Phe Ile Arg Asp Leu Phe Leu Arg Ile Ser Thr Ala Thr
                405                 410                 415

Gly Asp Gly Lys His Tyr Cys Tyr Pro His Phe Thr Cys Ala Val Asp
            420                 425                 430

Thr Glu Asn Ile Arg Arg Val Phe Asn Asp Cys Arg Asp Ile Ile Gln
        435                 440                 445

Arg Met His Leu Lys Gln Tyr Glu Leu Leu
    450                 455

<210> SEQ ID NO 23
<211> LENGTH: 1125
<212> TYPE: DNA
<213> ORGANISM: Mus musculus

<400> SEQUENCE: 23
atggcccggt ccctgacttg gggctgctgt ccctggtgcc tgacagagga ggagaagact     60
gccgccagaa tcgaccagga gatcaacagg attttgttgg aacagaaaaa acaagagcgc    120
gaggaattga aactcctgct gttggggcct ggtgagagcg ggaagagtac gttcatcaag    180
cagatgcgca tcattcacgg tgtgggctac tcggaggagg accgcagagc cttccggctg    240
ctcatctacc agaacatctt cgtctccatg caggccatga tagatgcgat ggaccggctg    300
cagatcccct tcagcaggcc tgacagcaag cagcacgcca gcctagtgat gacccaggac    360
ccctataaag tgagcacatt cgagaagcca tatgcagtgg ccatgcagta cctgtggcgg    420
gacgcgggca tccgtgcatg ctacgagcga aggcgtgaat tccacttcct ggactccgcg    480
gtgtattacc tgtcacacct ggagcgcata tcagaggaca gctacatccc cactgcgcaa    540
gacgtgctgc gcagtcgcat gcccaccaca ggcatcaatg agtactgctt ctccgtgaag    600
aaaaccaaac tgcgcatcgt ggatgttggt ggccagaggt cagagcgtag gaaatggatt    660 cactgttttcg agaacgtgat tgccctcatc tacctggcct ccctgagcga gtatgaccag    720
tgcctagagg agaacgatca ggagaaccgc atggaggaga gtctcgctct gttcagcacg    780
atcctagagc tgccctggtt caagagcacc tcggtcatcc tcttcctcaa caagacggac    840
atcctggaag ataagattca cacctcccac ctggccacat acttccccag cttcagggga    900
ccccggcgag acgcagaggc cgccaagagc ttcatcttgg acatgtatgc gcgcgtgtac    960
gcgagctgcg cagagccca ggacggtggc aggaaaggct cccgcgcgcg ccgcttcttc   1020
gcacacttca cctgtgccac ggacacgcaa agcgtccgca gcgtgttcaa ggacgtgcgg   1080
gactcggtgc tggcccggta cctggacgag atcaacctgc tgtga                  1125

<210> SEQ ID NO 24
<211> LENGTH: 374
<212> TYPE: PRT
<213> ORGANISM: Mus musculus

<400> SEQUENCE: 24

Met Ala Arg Ser Leu Thr Trp Gly Cys Cys Pro Trp Cys Leu Thr Glu
1               5                   10                  15

Glu Glu Lys Thr Ala Ala Arg Ile Asp Gln Glu Ile Asn Arg Ile Leu

```
            20                  25                  30
Leu Glu Gln Lys Lys Gln Glu Arg Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Val Gly Tyr Ser Glu Glu Asp Arg Ala Phe Arg Leu
65                  70                  75                  80

Leu Ile Tyr Gln Asn Ile Phe Val Ser Met Gln Ala Met Ile Asp Ala
                85                  90                  95

Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Thr Phe Glu
        115                 120                 125

Lys Pro Tyr Ala Val Ala Met Gln Tyr Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Ser Glu Asp Ser Tyr Ile
                165                 170                 175

Pro Thr Ala Gln Asp Val Leu Arg Ser Arg Met Pro Thr Thr Gly Ile
            180                 185                 190

Asn Glu Tyr Cys Phe Ser Val Lys Lys Thr Lys Leu Arg Ile Val Asp
        195                 200                 205

Val Gly Gly Gln Arg Ser Glu Arg Arg Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asp Gln Glu Asn Arg Met Glu Glu Ser Leu Ala
                245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
        275                 280                 285

Ser His Leu Ala Thr Tyr Phe Pro Ser Phe Gln Gly Pro Arg Arg Asp
    290                 295                 300

Ala Glu Ala Ala Lys Ser Phe Ile Leu Asp Met Tyr Ala Arg Val Tyr
305                 310                 315                 320

Ala Ser Cys Ala Glu Pro Gln Asp Gly Gly Arg Lys Gly Ser Arg Ala
                325                 330                 335

Arg Arg Phe Phe Ala His Phe Thr Cys Ala Thr Asp Thr Gln Ser Val
            340                 345                 350

Arg Ser Val Phe Lys Asp Val Arg Asp Ser Val Leu Ala Arg Tyr Leu
        355                 360                 365

Asp Glu Ile Asn Leu Leu
    370

<210> SEQ ID NO 25
<211> LENGTH: 1125
<212> TYPE: DNA
<213> ORGANISM: Homo Sapiens

<400> SEQUENCE: 25
atggcccggt cgctgacctg gcgctgctgc ccctggtgcc tgacggagga tgagaaggcc    60
gccgcccggg tggaccagga gatcaacagg atcctcttgg agcagaagaa gcaggaccgc   120
```

```
ggggagctga agctgctgct tttgggccca ggcgagagcg ggaagagcac cttcatcaag      180
cagatgcgga tcatccacgg cgccggctac tcggaggagg agcgcaaggg cttccggccc      240
ctggtctacc agaacatctt cgtgtccatg cgggccatga tcgaggccat ggagcggctg      300
cagattccat tcagcaggcc cgagagcaag caccacgcca gcctggtcat gagccaggac      360
ccctataaag tgaccacgtt tgagaagcgc tacgctgcgg ccatgcagtg gctgtggagg      420
gatgccggca tccgggcctg ctatgagcgt cggcgggaat tccacctgct cgattcagcc      480
gtgtactacc tgtcccacct ggagcgcatc accgaggagg gctacgtccc cacagctcag      540
gacgtgctcc gcagccgcat gcccaccact ggcatcaacg agtactgctt ctccgtgcag      600
aaaaccaacc tgcggatcgt ggacgtcggg gccagaagt cagagcgtaa gaaatggatc       660
cattgtttcg agaacgtgat cgccctcatc tacctggcct cactgagtga atacgaccag      720
tgcctggagg agaacaacca ggagaaccgc atgaaggaga gcctcgcatt gtttgggact      780
atcctggaac taccctggtt caaaagcaca tccgtcatcc tctttctcaa caaaaccgac      840
atcctggagg agaaaatccc cacctcccac ctggctacct atttccccag tttccagggc      900
cctaagcagg atgctgaggc agccaagagg ttcatcctgg acatgtacac gaggatgtac      960
accgggtgcg tggacggccc cgagggcagc aagaagggcg cacgatcccg acgcctcttc     1020
agccactaca catgtgccac agacacacag aacatccgca aggtcttcaa ggacgtgcgg     1080
gactcggtgc tcgcccgcta cctggacgag atcaacctgc tgtga                    1125
```

<210> SEQ ID NO 26
<211> LENGTH: 374
<212> TYPE: PRT
<213> ORGANISM: Homo Sapiens

<400> SEQUENCE: 26

```
Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
                20                  25                  30

Leu Glu Gln Lys Lys Gln Asp Arg Gly Glu Leu Lys Leu Leu Leu
            35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190
```

| | | | | | | | | | | | | |
|---|---|---|---|---|---|---|---|---|---|---|---|---|
| Asn | Glu | Tyr | Cys | Phe | Ser | Val | Gln | Lys | Thr | Asn | Leu | Arg | Ile | Val | Asp |
| | | 195 | | | | 200 | | | | | 205 | | | | |
| Val | Gly | Gly | Gln | Lys | Ser | Glu | Arg | Lys | Lys | Trp | Ile | His | Cys | Phe | Glu |
| 210 | | | | | 215 | | | | | 220 | | | | | |
| Asn | Val | Ile | Ala | Leu | Ile | Tyr | Leu | Ala | Ser | Leu | Ser | Glu | Tyr | Asp | Gln |
| 225 | | | | | 230 | | | | | 235 | | | | | 240 |
| Cys | Leu | Glu | Glu | Asn | Asn | Gln | Glu | Asn | Arg | Met | Lys | Glu | Ser | Leu | Ala |
| | | | | 245 | | | | | 250 | | | | | 255 | |
| Leu | Phe | Gly | Thr | Ile | Leu | Glu | Leu | Pro | Trp | Phe | Lys | Ser | Thr | Ser | Val |
| | | | 260 | | | | | 265 | | | | | 270 | | |
| Ile | Leu | Phe | Leu | Asn | Lys | Thr | Asp | Ile | Leu | Glu | Glu | Lys | Ile | Pro | Thr |
| | 275 | | | | | 280 | | | | | 285 | | | | |
| Ser | His | Leu | Ala | Thr | Tyr | Phe | Pro | Ser | Phe | Gln | Gly | Pro | Lys | Gln | Asp |
| 290 | | | | | 295 | | | | | 300 | | | | | |
| Ala | Glu | Ala | Ala | Lys | Arg | Phe | Ile | Leu | Asp | Met | Tyr | Thr | Arg | Met | Tyr |
| 305 | | | | | 310 | | | | | 315 | | | | | 320 |
| Thr | Gly | Cys | Val | Asp | Gly | Pro | Glu | Gly | Ser | Lys | Lys | Gly | Ala | Arg | Ser |
| | | | | 325 | | | | | 330 | | | | | 335 | |
| Arg | Arg | Leu | Phe | Ser | His | Tyr | Thr | Cys | Ala | Thr | Asp | Thr | Gln | Asn | Ile |
| | | | 340 | | | | | 345 | | | | | 350 | | |
| Arg | Lys | Val | Phe | Lys | Asp | Val | Arg | Asp | Ser | Val | Leu | Ala | Arg | Tyr | Leu |
| | 355 | | | | | 360 | | | | | 365 | | | | |
| Asp | Glu | Ile | Asn | Leu | Leu |
| | 370 | | | | |

<210> SEQ ID NO 27
<211> LENGTH: 939
<212> TYPE: DNA
<213> ORGANISM: Mus Musculus

<400> SEQUENCE: 27

```
atgacctcag ccagaaatgc ttcccatact gtgagtcact tcatcctctt aggcttccct      60
tgccgcagag aaatacagat cttccttttc tccatattct ttatgattta catttttgact   120
ttgcttggaa atatggcaat tgtgtatgca gtgtactggg atcatcggct tcatacaccc   180
atgtacattc tgctggccaa cttctccttc ctagagatat gctatgtcaa ctctgatgtg   240
ccaaacatgc tggtcaactt cctctccacg accaaaaacca tctccttcac tcgatgccta   300
ctccagttgt acttcttctt ctccctgggc acaactgaat gtctatttct ctccatcatg   360
gcctatgaca ggtccctggc aatctgccgc ccactgcact accccactgt catgaccact   420
atgttctgtg caaccttgt catatttgc tgggtctatg ggttcctctg gttctcttatc   480
ccagtgatac tcattactca gctgccattt tgtgggccaa atgtgataga tgactttctt   540
tgtgaccttg gtcccttgct ggccctagct tcagtctgtg tcccaatccc aggcactgtt   600
ctcatctgtg cactatgag ttccctcctc atctttggca cattttttta tattattggt   660
tcatatacct tagtgctgag ggctgtgatc cggatgccct cttctgctgg ttcaaagaag   720
gcattctcca cctgttcatc acacctggct gttgtatttc tattttatgg ttcagtcatg   780
ataacatatg taagcccagg atcaggacaa gcaaagggca tgcagaagtt cacaacttta   840
ttctattcag ttatgactcc tttcttcaac cccatgatct atagcctccg aaataaagaa   900
atgaaagatg ccttgaaaaa ggttgtagga ggttcttag                            939
```

<210> SEQ ID NO 28
<211> LENGTH: 312

<212> TYPE: PRT
<213> ORGANISM: Mus Musculus

<400> SEQUENCE: 28

```
Met Thr Ser Ala Arg Asn Ala Ser His Thr Val Ser His Phe Ile Leu
1               5                   10                  15
Leu Gly Phe Pro Cys Arg Arg Glu Ile Gln Ile Phe Leu Phe Ser Ile
            20                  25                  30
Phe Phe Met Ile Tyr Ile Leu Thr Leu Leu Gly Asn Met Ala Ile Val
        35                  40                  45
Tyr Ala Val Tyr Trp Asp His Arg Leu His Thr Pro Met Tyr Ile Leu
    50                  55                  60
Leu Ala Asn Phe Ser Phe Leu Glu Ile Cys Tyr Val Asn Ser Asp Val
65                  70                  75                  80
Pro Asn Met Leu Val Asn Phe Leu Ser Thr Thr Lys Thr Ile Ser Phe
                85                  90                  95
Thr Arg Cys Leu Leu Gln Leu Tyr Phe Phe Ser Leu Gly Thr Thr
            100                 105                 110
Glu Cys Leu Phe Leu Ser Ile Met Ala Tyr Asp Arg Phe Leu Ala Ile
        115                 120                 125
Cys Arg Pro Leu His Tyr Pro Thr Val Met Thr Thr Met Phe Cys Gly
    130                 135                 140
Asn Leu Val Ile Phe Cys Trp Val Tyr Gly Phe Leu Trp Phe Leu Ile
145                 150                 155                 160
Pro Val Ile Leu Ile Thr Gln Leu Pro Phe Cys Gly Pro Asn Val Ile
                165                 170                 175
Asp Asp Phe Leu Cys Asp Leu Gly Pro Leu Leu Ala Leu Ala Ser Val
            180                 185                 190
Cys Val Pro Ile Pro Gly Thr Val Leu Ile Cys Gly Thr Met Ser Ser
        195                 200                 205
Leu Leu Ile Phe Gly Thr Phe Phe Tyr Ile Ile Gly Ser Tyr Thr Leu
    210                 215                 220
Val Leu Arg Ala Val Ile Arg Met Pro Ser Ser Ala Gly Ser Lys Lys
225                 230                 235                 240
Ala Phe Ser Thr Cys Ser Ser His Leu Ala Val Val Phe Leu Phe Tyr
                245                 250                 255
Gly Ser Val Met Ile Thr Tyr Val Ser Pro Gly Ser Gly Gln Ala Lys
            260                 265                 270
Gly Met Gln Lys Phe Thr Thr Leu Phe Tyr Ser Val Met Thr Pro Phe
        275                 280                 285
Phe Asn Pro Met Ile Tyr Ser Leu Arg Asn Lys Glu Met Lys Asp Ala
    290                 295                 300
Leu Lys Lys Val Val Gly Gly Ser
305                 310
```

<210> SEQ ID NO 29
<211> LENGTH: 936
<212> TYPE: DNA
<213> ORGANISM: Mus musculus

<400> SEQUENCE: 29

```
atgaaagcct ttagcagccc cagcaactcc agcatcatca ctggcttcat cctcctgggc     60
ttcccctgcc ccaaggaggg gcaaatcctc ctctttgtgc tcttcttcat tatctacatc    120
cttaccctca tgggcaatgc ttccatcata tgtgctgtgt gctatgataa gaaacttcac    180
```

```
agccccatgt acctcctgct ggccaacttc tccttcctag aaatctggta tgtcacctcc    240
acagtcccca acatgttggc caacttcctc tctgacacga aggtcatctc tttctctgga    300
tgcttcctgc agttctattt cttcttctcc ttgggttcta cagaatgctt tttcctggca    360
gtcatggcat ttgatcgata ccttgccatc tgcagacctc tacattatcc ttctctcatg    420
actgggcgcc tctgcaacat ccttgtgatc agttgctggg tgcttggttt cctctggttc    480
cctgttccca tcatcatcat ctcccaaatg tccttctgtg gatccagaat tatagaccac    540
ttcctgtgtg acccaggccc tctgttggcc ctcacctgtg tgagaaattc tttaattgag    600
atgactagct ctactttaag ttccctgctt ttatttgttc cattttttt tatcatgggg    660 tcttatgctc tagtaatgag ggctgtgctc agggtcccctt cagcagctgg acgaagaaag    720
gccttctcca cctgtgggtc acacttgact gtggtttctc ttttctatgg ctcagtgatg    780
gtcatgtatg tgagcccaac atctgaacat gcagctggag tgcaaaaact tgtgactctg    840
ttttattctg tggttactcc cctccttaat cctgtgatat acagtctgag gaacagagat    900
atgaaacatg caatgaaaaa gttactgaaa atgtaa    936
```

<210> SEQ ID NO 30
<211> LENGTH: 311
<212> TYPE: PRT
<213> ORGANISM: Mus musculus

<400> SEQUENCE: 30

```
Met Lys Ala Phe Ser Ser Pro Ser Asn Ser Ile Ile Thr Gly Phe
 1               5                   10                  15

Ile Leu Leu Gly Phe Pro Cys Pro Lys Glu Gly Gln Ile Leu Leu Phe
                20                  25                  30

Val Leu Phe Phe Ile Ile Tyr Ile Leu Thr Leu Met Gly Asn Ala Ser
                35                  40                  45

Ile Ile Cys Ala Val Cys Tyr Asp Lys Lys Leu His Ser Pro Met Tyr
            50                  55                  60

Leu Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Leu Gly
                100                 105                 110

Ser Thr Glu Cys Phe Phe Leu Ala Val Met Ala Phe Asp Arg Tyr Leu
            115                 120                 125

Ala Ile Cys Arg Pro Leu His Tyr Pro Ser Leu Met Thr Gly Arg Leu
        130                 135                 140

Cys Asn Ile Leu Val Ile Ser Cys Trp Val Leu Gly Phe Leu Trp Phe
145                 150                 155                 160

Pro Val Pro Ile Ile Ile Ile Ser Gln Met Ser Phe Cys Gly Ser Arg
                165                 170                 175

Ile Ile Asp His Phe Leu Cys Asp Pro Gly Pro Leu Leu Ala Leu Thr
            180                 185                 190

Cys Val Arg Asn Ser Leu Ile Glu Met Thr Ser Ser Thr Leu Ser Ser
        195                 200                 205

Leu Leu Leu Phe Val Pro Phe Phe Ile Met Gly Ser Tyr Ala Leu
        210                 215                 220

Val Met Arg Ala Val Leu Arg Val Pro Ser Ala Ala Gly Arg Arg Lys
225                 230                 235                 240
```

```
Ala Phe Ser Thr Cys Gly Ser His Leu Thr Val Ser Leu Phe Tyr
                245                 250                 255

Gly Ser Val Met Val Met Tyr Val Ser Pro Thr Ser Glu His Ala Ala
            260                 265                 270

Gly Val Gln Lys Leu Val Thr Leu Phe Tyr Ser Val Val Thr Pro Leu
        275                 280                 285

Leu Asn Pro Val Ile Tyr Ser Leu Arg Asn Arg Asp Met Lys His Ala
        290                 295                 300

Met Lys Lys Leu Leu Lys Met
305                 310

<210> SEQ ID NO 31
<211> LENGTH: 930
<212> TYPE: DNA
<213> ORGANISM: Mus musculus

<400> SEQUENCE: 31
atgaaaaccc tcagcagctc caacaacacc atcactggct tcatcctctt gggcttcccc       60
tgccccaggg aggggcaaat cctcctcttt gtgctcttct tcattgtcta cctccttacc      120
ctcatgggca atgcttccat catatgtgct gtgtgctgtg atcagaaact tcacaccccc      180
atgtacctcc tgctggccaa cttctccttc ctggaaatct gttatgtcac ctccacagtc      240
cccaacatgt tggccaactt cctctctgaa aacaaggtca tttccttcgc tggatgcttc      300
ctgcagttct atttcttctt ctccttgggt tctacagaat gcttttttcct ggcagtcatg      360
gcatttgatc gataccttgc catctgtagg ccactacatt atcctgctct catgactggg      420
cacctctgca acatccttgt gatcagttgc tgggtgcttg gtttcctctg gttccctgtt      480
cccatcatca tcatctccca gatgtccttc tgtggatcca gaattataga ccacttcctg      540
tgtgacccag gccctctgtt ggccctcacc tgttccagag ccccattgat ggaggttttc      600
tgggcaattt taggttctat gctcctgttt attccttttt tctgcatcat gggatcttat      660
atattggtcc taagagctgt gttcagagtt ccttcaagag atggacaaaa aaaggctttc      720
tccacttgcg gatctcatct cacagtagtt tcactatttt atggctcagt gatgataatg      780
tatctgagcc aacatctga gcatgaagct ggaatgcaga agcttgtaac tctattttat      840
tctgtggtta ctccactcat taatcctgtg atatacagtc tgaggaacaa agatatgaaa      900
aatgccctgc agaagatttt aaaaacataa                                       930

<210> SEQ ID NO 32
<211> LENGTH: 309
<212> TYPE: PRT
<213> ORGANISM: Mus musculus

<400> SEQUENCE: 32

Met Lys Thr Leu Ser Ser Ser Asn Asn Thr Ile Thr Gly Phe Ile Leu
1               5                  10                  15

Leu Gly Phe Pro Cys Pro Arg Glu Gly Gln Ile Leu Leu Phe Val Leu
            20                  25                  30

Phe Phe Ile Val Tyr Leu Leu Thr Leu Met Gly Asn Ala Ser Ile Ile
        35                  40                  45

Cys Ala Val Cys Cys Asp Gln Lys Leu His Thr Pro Met Tyr Leu Leu
    50                  55                  60

Leu Ala Asn Phe Ser Phe Leu Glu Ile Cys Tyr Val Thr Ser Thr Val
65                  70                  75                  80

Pro Asn Met Leu Ala Asn Phe Leu Ser Glu Asn Lys Val Ile Ser Phe
```

```
                85                  90                  95
Ala Gly Cys Phe Leu Gln Phe Tyr Phe Phe Ser Leu Gly Ser Thr
                    100                 105                 110

Glu Cys Phe Phe Leu Ala Val Met Ala Phe Asp Arg Tyr Leu Ala Ile
                115                 120                 125

Cys Arg Pro Leu His Tyr Pro Ala Leu Met Thr Gly His Leu Cys Asn
            130                 135                 140

Ile Leu Val Ile Ser Cys Trp Val Leu Gly Phe Leu Trp Phe Pro Val
145                 150                 155                 160

Pro Ile Ile Ile Ile Ser Gln Met Ser Phe Cys Gly Ser Arg Ile Ile
                165                 170                 175

Asp His Phe Leu Cys Asp Pro Gly Pro Leu Leu Ala Leu Thr Cys Ser
            180                 185                 190

Arg Ala Pro Leu Met Glu Val Phe Trp Ala Ile Leu Gly Ser Met Leu
        195                 200                 205

Leu Phe Ile Pro Phe Phe Cys Ile Met Gly Ser Tyr Ile Leu Val Leu
        210                 215                 220

Arg Ala Val Phe Arg Val Pro Ser Arg Asp Gly Gln Lys Lys Ala Phe
225                 230                 235                 240

Ser Thr Cys Gly Ser His Leu Thr Val Val Ser Leu Phe Tyr Gly Ser
                    245                 250                 255

Val Met Ile Met Tyr Leu Ser Pro Thr Ser Glu His Glu Ala Gly Met
                260                 265                 270

Gln Lys Leu Val Thr Leu Phe Tyr Ser Val Val Thr Pro Leu Ile Asn
            275                 280                 285

Pro Val Ile Tyr Ser Leu Arg Asn Lys Asp Met Lys Asn Ala Leu Gln
        290                 295                 300

Lys Ile Leu Lys Thr
305

<210> SEQ ID NO 33
<211> LENGTH: 936
<212> TYPE: DNA
<213> ORGANISM: Mus musculus

<400> SEQUENCE: 33
atgaaaaccc tcagcagccc cagcaactcc agcaccatca ctggcttcat cctcttgggc      60
ttcccctgcc ccagggaggg gcaaatcctc ctctttgtga ccttcttcat tgtttacata     120
ctcattctta tgggcaatgc ttccatcatc tgtgctgtgt actgtgatca gagcctccac     180 accccccatgt acttcctgct ggccaacttc tccttcctgg agatctggta tgtcacctcc     240
acagtcccca catgttggcc aacttccttt cagacaccaa ggtcatctct ttctctggga     300
tgcttcctgc agttctattt cttcttctcc tttggttcta cagaatgctt tttcctggca     360
gtcatggcat tgatcgata ccttgccatc tgtaggccac tacattatcc ttctctcatg     420
actgggcacc tctgcaacat ccttgtgatc agttgctggg tcttggtttt cctctggttc     480
cctgtaccca tcatcatcat ctcccagatg tccttctgtg ggtccagaat tatagaccac     540
ttcctgtgtg acccaggccc tcttttggcc cttgcctgtt ccagagcccc attgatggag     600
gttttctgga caattataat gtctatgctc ctggttattc ctttcctctt catcatggga     660
acttacatat tggtcctaag agctgtgttt agacttcctt caagagatgg acaaaaaaag     720
gccttctcca cttgcgggtc tcatctcaca gtagtttcac tcttttattg ctcagtgatg     780
aaaatgtatt tgagcccaac atctgagcat gaagctggaa tgcagaagct tgtaactcta     840
```

```
ttttattctg tgggtactcc actacttaat cctgtgatat acagtctgag gaacaaagat    900
atgaaaaatg ccctgcagaa gatttttaaga acataa                             936
```

<210> SEQ ID NO 34
<211> LENGTH: 311
<212> TYPE: PRT
<213> ORGANISM: Mus musculus

<400> SEQUENCE: 34

```
Met Lys Thr Leu Ser Ser Pro Ser Asn Ser Ser Thr Ile Thr Gly Phe
1               5                   10                  15

Ile Leu Leu Gly Phe Pro Cys Pro Arg Glu Gly Gln Ile Leu Leu Phe
            20                  25                  30

Val Thr Phe Phe Ile Val Tyr Ile Leu Ile Leu Met Gly Asn Ala Ser
        35                  40                  45

Ile Ile Cys Ala Val Tyr Cys Asp Gln Ser Leu His Thr Pro Met Tyr
    50                  55                  60

Phe Leu Leu Ala Asn Phe Ser Phe Leu Glu Ile Trp Tyr Val Thr Ser
65                  70                  75                  80

Thr Val Pro Asn Met Leu Ala Asn Phe Leu Ser Asp Thr Lys Val Ile
                85                  90                  95

Ser Phe Ser Gly Cys Phe Leu Gln Phe Tyr Phe Phe Ser Phe Gly
            100                 105                 110

Ser Thr Glu Cys Phe Phe Leu Ala Val Met Ala Phe Asp Arg Tyr Leu
        115                 120                 125

Ala Ile Cys Arg Pro Leu His Tyr Pro Ser Leu Met Thr Gly His Leu
    130                 135                 140

Cys Asn Ile Leu Val Ile Ser Cys Trp Val Leu Gly Phe Leu Trp Phe
145                 150                 155                 160

Pro Val Pro Ile Ile Ile Ile Ser Gln Met Ser Phe Cys Gly Ser Arg
                165                 170                 175

Ile Ile Asp His Phe Leu Cys Asp Pro Gly Pro Leu Leu Ala Leu Ala
            180                 185                 190

Cys Ser Arg Ala Pro Leu Met Glu Val Phe Trp Thr Ile Ile Met Ser
        195                 200                 205

Met Leu Leu Val Ile Pro Phe Leu Phe Ile Met Gly Thr Tyr Ile Leu
    210                 215                 220

Val Leu Arg Ala Val Phe Arg Leu Pro Ser Arg Asp Gly Gln Lys Lys
225                 230                 235                 240

Ala Phe Ser Thr Cys Gly Ser His Leu Thr Val Val Ser Leu Phe Tyr
                245                 250                 255

Cys Ser Val Met Lys Met Tyr Leu Ser Pro Thr Ser Glu His Glu Ala
            260                 265                 270

Gly Met Gln Lys Leu Val Thr Leu Phe Tyr Ser Val Gly Thr Pro Leu
        275                 280                 285

Leu Asn Pro Val Ile Tyr Ser Leu Arg Asn Lys Asp Met Lys Asn Ala
    290                 295                 300

Leu Gln Lys Ile Leu Arg Thr
305                 310
```

<210> SEQ ID NO 35
<211> LENGTH: 972
<212> TYPE: DNA
<213> ORGANISM: Mus musculus

<400> SEQUENCE: 35

```
atgaaaatct tcagcagccc agcaactcc agcaccatca ctgggttcat cctcttgggc    60
ttccctgcc ccagggaggg gcaaatcctc ctctttgtgc tcttctccat tgtctacctc   120
cttaccctca tgggcaatgc ttccatcatc tgcgctgtgt actgtgatca gaaacttcac   180
atccccatgt acctcctgct ggccaacttt tctttcctgg agatctggta tgtcacctcc   240
acagtcccca catgttggc caacttcctc tctgacacca aggtcatctc tttctctgga   300
tgcttcctgc agttctattt cttcttctcc ttgggttcta cagaatgctt tttcctggca   360
gtcatggcat ttgatcgata ccttgctatc tgcaggcctc tacattaccc tgctctcatg   420
actgggcgcc tctgcaacat ccttgtgatc agttgctgga tacttggttt cctctggttc   480
cctgttccca tcatcatcat ctcccaggtg tcgttctgtg ggtctagaat tatagaccac   540
ttcctgtgtg acccaggtcc tctgctagca ctcacttgca aaaaatctcc cctaattgag   600
ctggtcttct ctatcttaag tcctctgcct ctcattattc cttttgtctt catcatggga   660
tcttatactc tggtcctagc agctgtattg aaggtcccctt cagcctctgg aaaaagaaag   720
gctttctcaa cctgtgggtc tcatctggca gtggttgcat tattttatgg ctcagtactg   780
gtcatgtatg ggagtccaac atctgagcat gaagctggga tgcagaaaat tgtgactctg   840
tttactctg tcttgacccc actcctcaat cctgtgatat atagtcttag gaacaaacat   900
atgaagatag ccctgaagga aattctgagg aagattaaaa attggtcaac aaaaaaggcc   960
ttgggcaatt aa                                                        972
```

<210> SEQ ID NO 36
<211> LENGTH: 323
<212> TYPE: PRT
<213> ORGANISM: Mus musculus

<400> SEQUENCE: 36

```
Met Lys Ile Phe Ser Ser Pro Ser Asn Ser Ser Thr Ile Thr Gly Phe
1               5                   10                  15
Ile Leu Gly Phe Pro Cys Pro Arg Glu Gly Gln Ile Leu Leu Phe
            20                  25                  30
Val Leu Phe Ser Ile Val Tyr Leu Leu Thr Leu Met Gly Asn Ala Ser
        35                  40                  45
Ile Ile Cys Ala Val Tyr Cys Asp Gln Lys Leu His Ile Pro Met Tyr
    50                  55                  60
Leu Leu Leu Ala Asn Phe Ser Phe Leu Glu Ile Trp Tyr Val Thr Ser
65                  70                  75                  80
Thr Val Pro Asn Met Leu Ala Asn Phe Leu Ser Asp Thr Lys Val Ile
                85                  90                  95
Ser Phe Ser Gly Cys Phe Leu Gln Phe Tyr Phe Phe Ser Leu Gly
            100                 105                 110
Ser Thr Glu Cys Phe Phe Leu Ala Val Met Ala Phe Asp Arg Tyr Leu
        115                 120                 125
Ala Ile Cys Arg Pro Leu His Tyr Pro Ala Leu Met Thr Gly Arg Leu
    130                 135                 140
Cys Asn Ile Leu Val Ile Ser Cys Trp Ile Leu Gly Phe Leu Trp Phe
145                 150                 155                 160
Pro Val Pro Ile Ile Ile Ser Gln Val Ser Phe Cys Gly Ser Arg
                165                 170                 175
Ile Ile Asp His Phe Leu Cys Asp Pro Gly Pro Leu Leu Ala Leu Thr
            180                 185                 190
```

```
Cys Lys Lys Ser Pro Leu Ile Glu Leu Val Phe Ser Ile Leu Ser Pro
            195                 200                 205
Leu Pro Leu Ile Ile Pro Phe Val Phe Ile Met Gly Ser Tyr Thr Leu
    210                 215                 220
Val Leu Ala Ala Val Leu Lys Val Pro Ser Ala Ser Gly Lys Arg Lys
225                 230                 235                 240
Ala Phe Ser Thr Cys Gly Ser His Leu Ala Val Val Ala Leu Phe Tyr
                245                 250                 255
Gly Ser Val Leu Val Met Tyr Gly Ser Pro Thr Ser Glu His Glu Ala
            260                 265                 270
Gly Met Gln Lys Ile Val Thr Leu Phe Tyr Ser Val Leu Thr Pro Leu
        275                 280                 285
Leu Asn Pro Val Ile Tyr Ser Leu Arg Asn Lys His Met Lys Ile Ala
    290                 295                 300
Leu Lys Glu Ile Leu Arg Lys Ile Lys Asn Trp Ser Thr Lys Lys Ala
305                 310                 315                 320
Leu Gly Asn

<210> SEQ ID NO 37
<211> LENGTH: 945
<212> TYPE: DNA
<213> ORGANISM: Mus musculus

<400> SEQUENCE: 37
atgaacgtgt cagagggatc cacggtgaca tattttgtct tattgggatt ccctggtccc        60
tggaagattc aaatcacact tttctcactg attctgctgc tctacatgat aactttgact       120
gggaatatgg ccatcatttg tgcagtgaga tggaaccaac aactccacac ccctatgtat       180
atgttcctgg ccaacttctc cttcctagaa atctggtacg tgacctgcac agttcccaac       240
atgctgatca actctctttc caaaactaag actatatctt cactggatg ctttactcag       300
ttctacttct tcttctccct gggcacaact gaatgcttct tcctctgtgc catggcttat       360
gatcggtacc tagccatctg ctacccactg cactatcctt ccatcatgac taggcaattc       420
tgcagtattc tgatgtccct ctgttggatc attggtttct ctgcacattt gattcccatt       480
ttccttattt ctcaattgtc tttctgtggc cccaatatca ttgatcactt tctctgtgat       540
gtggacccac taatagcact gtcctgtacc cctacacaca tcataagtca tgtattctat       600
tctataagta ctcttatcat tattctcact ggtttgtaca tccttggatc ttatgccttg       660
gtgctcagag ctgttcttca ggttccttct tcagatggac gtcaaaaggc cttctcaacc       720
tgtggatccc acctgctggt agtgtctctg ttctatggaa ccataatggt gatgtatgtc       780
agccccacat ctggcaactc agttgacatg aataaaatta tcacactgat atattctgtg       840
gtgacaccag ctttaaatcc tttcatctat agtctgcgta caaggatat gaaatatgct       900
ctccatcatg tcttctttgg gaatagcatt atgcaaaact tataa                      945

<210> SEQ ID NO 38
<211> LENGTH: 314
<212> TYPE: PRT
<213> ORGANISM: Mus musculus

<400> SEQUENCE: 38

Met Asn Val Ser Glu Gly Ser Thr Val Thr Tyr Phe Val Leu Leu Gly
1               5                   10                  15
Phe Pro Gly Pro Trp Lys Ile Gln Ile Thr Leu Phe Ser Leu Ile Leu
```

20                  25                  30
Leu Leu Tyr Met Ile Thr Leu Thr Gly Asn Met Ala Ile Ile Cys Ala
             35                  40                  45

Val Arg Trp Asn Gln Gln Leu His Thr Pro Met Tyr Met Phe Leu Ala
 50                  55                  60

Asn Phe Ser Phe Leu Glu Ile Trp Tyr Val Thr Cys Thr Val Pro Asn
 65                  70                  75                  80

Met Leu Ile Asn Ser Leu Ser Lys Thr Lys Thr Ile Ser Phe Thr Gly
                 85                  90                  95

Cys Phe Thr Gln Phe Tyr Phe Phe Ser Leu Gly Thr Thr Glu Cys
                100                 105                 110

Phe Phe Leu Cys Ala Met Ala Tyr Asp Arg Tyr Leu Ala Ile Cys Tyr
             115                 120                 125

Pro Leu His Tyr Pro Ser Ile Met Thr Arg Gln Phe Cys Ser Ile Leu
             130                 135                 140

Met Ser Leu Cys Trp Ile Ile Gly Phe Ser Ala His Leu Ile Pro Ile
145                 150                 155                 160

Phe Leu Ile Ser Gln Leu Ser Phe Cys Gly Pro Asn Ile Ile Asp His
                165                 170                 175

Phe Leu Cys Asp Val Asp Pro Leu Ile Ala Leu Ser Cys Thr Pro Thr
             180                 185                 190

His Ile Ile Ser His Val Phe Tyr Ser Ile Ser Thr Leu Ile Ile Ile
             195                 200                 205

Leu Thr Gly Leu Tyr Ile Leu Gly Ser Tyr Ala Leu Val Leu Arg Ala
             210                 215                 220

Val Leu Gln Val Pro Ser Ser Asp Gly Arg Gln Lys Ala Phe Ser Thr
225                 230                 235                 240

Cys Gly Ser His Leu Leu Val Val Ser Leu Phe Tyr Gly Thr Ile Met
                245                 250                 255

Val Met Tyr Val Ser Pro Thr Ser Gly Asn Ser Val Asp Met Asn Lys
             260                 265                 270

Ile Ile Thr Leu Ile Tyr Ser Val Val Thr Pro Ala Leu Asn Pro Phe
             275                 280                 285

Ile Tyr Ser Leu Arg Asn Lys Asp Met Lys Tyr Ala Leu His His Val
             290                 295                 300

Phe Phe Gly Asn Ser Ile Met Gln Asn Leu
305                 310

<210> SEQ ID NO 39
<211> LENGTH: 942
<212> TYPE: DNA
<213> ORGANISM: Mus Musculus

<400> SEQUENCE: 39
atgaacagat cagtagcaca tgtaactgaa tttgttctct tgggatttcc tggttcctgg      60
aagatacaga ttttcctctt cgtgttgttt ttggtgtttt atgtcttgac attgttggga    120
aatggagcca tcatctgtgc agtaagatgt gactcacgtc tacataccccc catgtacttc    180 ctcctgggaa attttgcctt ccttgaaatc tggtatgttt cctccactat tcctaacata    240
ctagccaaca ttctgtctaa gaccaaggcc atctcatttt cagggtgctt cctgcagttc    300
tatttcttct tttcactggg tacaactgaa tgtctcttcc tggcagtaat ggcttatgat    360
aggtacctgg ccatttgccg cccattacat taccctacta tcatgactag gaggctgtgt    420
tgcattctgg tatcctcatg ctggctcatt ggatttcttg ggtacccaat ccctatcttc    480

```
tccatttccc agcttccctt ctgtggttct aatatcattg atcacttcct ctgtgacatg    540
gacccattga tggctttgtc ctgtgcccca gctcctatta ctgaatttat tttttatgcc    600
caaagttcct ttgtcctctt tttcactatt gcatacattc ttcggtccta tattttgttg    660
ctcaaggcta ttttcaggt tccttctgca gctggccgac gaaaggcctt ctctacctgt     720
ggttcccatt tagttgtggt gtcactcttc tatgggacag taatgataat gtacatgagt    780
cctacatatg gcatttcaac tttgatgcag aagatcctta cacttgtata ctctgtaatg    840
actcctctct ttaatcctct gatttatagc cttcgtaaca aggacatgaa acttgctctg    900
aggaaagttc tgttaggaat gagaattgtc aaaatatat ga                         942
```

<210> SEQ ID NO 40
<211> LENGTH: 313
<212> TYPE: PRT
<213> ORGANISM: Mus musculus

<400> SEQUENCE: 40

```
Met Asn Arg Ser Val Ala His Val Thr Glu Phe Val Leu Leu Gly Phe
1               5                   10                  15

Pro Gly Ser Trp Lys Ile Gln Ile Phe Leu Phe Val Leu Phe Leu Val
            20                  25                  30

Phe Tyr Val Leu Thr Leu Leu Gly Asn Gly Ala Ile Ile Cys Ala Val
        35                  40                  45

Arg Cys Asp Ser Arg Leu His Thr Pro Met Tyr Phe Leu Leu Gly Asn
    50                  55                  60

Phe Ala Phe Leu Glu Ile Trp Tyr Val Ser Ser Thr Ile Pro Asn Ile
65                  70                  75                  80

Leu Ala Asn Ile Leu Ser Lys Thr Lys Ala Ile Ser Phe Ser Gly Cys
                85                  90                  95

Phe Leu Gln Phe Tyr Phe Phe Phe Ser Leu Gly Thr Thr Glu Cys Leu
            100                 105                 110

Phe Leu Ala Val Met Ala Tyr Asp Arg Tyr Leu Ala Ile Cys Arg Pro
        115                 120                 125

Leu His Tyr Pro Thr Ile Met Thr Arg Arg Leu Cys Cys Ile Leu Val
    130                 135                 140

Ser Ser Cys Trp Leu Ile Gly Phe Leu Gly Tyr Pro Ile Pro Ile Phe
145                 150                 155                 160

Ser Ile Ser Gln Leu Pro Phe Cys Gly Ser Asn Ile Ile Asp His Phe
                165                 170                 175

Leu Cys Asp Met Asp Pro Leu Met Ala Leu Ser Cys Ala Pro Ala Pro
            180                 185                 190

Ile Thr Glu Phe Ile Phe Tyr Ala Gln Ser Ser Phe Val Leu Phe Phe
        195                 200                 205

Thr Ile Ala Tyr Ile Leu Arg Ser Tyr Ile Leu Leu Lys Ala Ile
    210                 215                 220

Phe Gln Val Pro Ser Ala Ala Gly Arg Arg Lys Ala Phe Ser Thr Cys
225                 230                 235                 240

Gly Ser His Leu Val Val Val Ser Leu Phe Tyr Gly Thr Val Met Ile
                245                 250                 255

Met Tyr Met Ser Pro Thr Tyr Gly Ile Ser Thr Leu Met Gln Lys Ile
            260                 265                 270

Leu Thr Leu Val Tyr Ser Val Met Thr Pro Leu Phe Asn Pro Leu Ile
        275                 280                 285
```

```
Tyr Ser Leu Arg Asn Lys Asp Met Lys Leu Ala Leu Arg Lys Val Leu
    290                 295                 300

Leu Gly Met Arg Ile Val Lys Asn Ile
305                 310

<210> SEQ ID NO 41
<211> LENGTH: 924
<212> TYPE: DNA
<213> ORGANISM: Mus musculus

<400> SEQUENCE: 41
atgaacgtgt cagagggatc cacggtgaca tattttgtct tattgggatt ccctggtccc     60
tggaagattc aaatcacact tttctcactg attctgctgc tctacatgat aactttgact    120
gggaatatgg ccatcatttg tgcagtgagg tggaaccaac aactccacac ccctatgtat    180
atgttcctgg ccaacttctc cttcctagaa atctggtacg tgacctgcac agttcccaac    240
atgctggtca actctctttc caaaactaag actatatcct cactggatg ctttactcag     300 ttctacttct tcttctccct gggcacaact gaatgcttct cctctgtgc catggcttat     360 gatcggtacc tagccatctg ctacccactg cactatcctt ccatcatgac taggcaattc    420
tgcagtattc tgatgtccct ctgttggatc attggtttct ctgcacattt gattcccatt    480
ttctttattt ctcaattgtc tttctgtggt cccaatatca ttgatcattt tctctgtgat    540
gtggacccac taatggtcct gtcctgtacc cctacaccca tcataaggca tgtattctat    600
tctataagta ctatattcat tgtcctcacc tgtttgtaca tccttggatc ctataccta     660 gtgctcagag ctgttcttca ggtttcttct tcagatggac gacaaaaggc cttctcaacc    720
tgtggatccc acctgctggg agtgtctctg ttttatggaa ccataatggt gatgtatgtg    780
actcccaagt ctagcaactc tgttgctatg cataaaatta tcacactgat atactctgtg    840
gtgacaccag ctttaaatcc tttcatctat agtctgcgta caaggatat gaaatatgcc     900 ctccataatg ttttctttgg ttag                                           924

<210> SEQ ID NO 42
<211> LENGTH: 307
<212> TYPE: PRT
<213> ORGANISM: Mus musculus

<400> SEQUENCE: 42

Met Asn Val Ser Glu Gly Ser Thr Val Thr Tyr Phe Val Leu Leu Gly
1               5                   10                  15

Phe Pro Gly Pro Trp Lys Ile Gln Ile Thr Leu Phe Ser Leu Ile Leu
            20                  25                  30

Leu Leu Tyr Met Ile Thr Leu Thr Gly Asn Met Ala Ile Ile Cys Ala
        35                  40                  45

Val Arg Trp Asn Gln Gln Leu His Thr Pro Met Tyr Met Phe Leu Ala
    50                  55                  60

Asn Phe Ser Phe Leu Glu Ile Trp Tyr Val Thr Cys Thr Val Pro Asn
65                  70                  75                  80

Met Leu Val Asn Ser Leu Ser Lys Thr Lys Thr Ile Ser Phe Thr Gly
                85                  90                  95

Cys Phe Thr Gln Phe Tyr Phe Phe Ser Leu Gly Thr Thr Glu Cys
                100                 105                 110

Phe Phe Leu Cys Ala Met Ala Tyr Asp Arg Tyr Leu Ala Ile Cys Tyr
            115                 120                 125

Pro Leu His Tyr Pro Ser Ile Met Thr Arg Gln Phe Cys Ser Ile Leu
```

Met Ser Leu Cys Trp Ile Ile Gly Phe Ser Ala His Leu Ile Pro Ile
145                 150                 155                 160

Phe Phe Ile Ser Gln Leu Ser Phe Cys Gly Pro Asn Ile Ile Asp His
            165                 170                 175

Phe Leu Cys Asp Val Asp Pro Leu Met Val Leu Ser Cys Thr Pro Thr
        180                 185                 190

Pro Ile Ile Arg His Val Phe Tyr Ser Ile Ser Thr Ile Phe Ile Val
    195                 200                 205

Leu Thr Cys Leu Tyr Ile Leu Gly Ser Tyr Thr Leu Val Leu Arg Ala
210                 215                 220

Val Leu Gln Val Ser Ser Asp Gly Arg Gln Lys Ala Phe Ser Thr
225                 230                 235                 240

Cys Gly Ser His Leu Leu Val Val Ser Leu Phe Tyr Gly Thr Ile Met
                245                 250                 255

Val Met Tyr Val Thr Pro Lys Ser Ser Asn Ser Val Ala Met His Lys
            260                 265                 270

Ile Ile Thr Leu Ile Tyr Ser Val Val Thr Pro Ala Leu Asn Pro Phe
        275                 280                 285

Ile Tyr Ser Leu Arg Asn Lys Asp Met Lys Tyr Ala Leu His Asn Val
    290                 295                 300

Phe Phe Gly
305

<210> SEQ ID NO 43
<211> LENGTH: 942
<212> TYPE: DNA
<213> ORGANISM: Mus musculus

<400> SEQUENCE: 43
atgaacagat cagcagcaca tgtaactgaa tttgttctct tgggatttcc tggttcctgg      60
aagatacaga ttttcctctt cgtgttgttt ttggtgtttt atgtcttgac attgttggga     120
aatggagcca tcatctgtgc agtaagatgt gactcacgtc tacataccc catgtacttc     180
ctcctgggaa attttgcctt ccttgaaatc tggtatgttt cctccactat tcctaacata     240
ctagccaaca ttctgtctaa gaccaaggcc atctcatttt cagggtgctt cctgcagttc     300
tatttcttct tttcactagg tacaactgaa tgtctcttcc tggcagtaat ggcttatgat     360
aggtacctgg ccatttgccg cccattacat taccctacca tcatgactag gaggctgtgt     420
tgcattctgg tatcctcatg ctggctcatt ggatttcttg gtacccaat ccctatcttc     480
tccatttccc agcttccctt ctgtggttct aatatcattg atcacttcct ctgtgacatg     540
gacccattga tggctttgtc ctgtgcccca gctcctatta ctgaatttat ttttatgcc      600
caaagttcct tgtcctctct tttcactatt gcatacattc ttcggtccta tattttgttg     660
ctcagggctg tttttcaggt tccttctgca gctggccgac gaaaggcctt ctctacctgt     720
ggttcccatt tagttgtggt atcactcttc tatggtacag taatggtaat gtatgtgagt     780
cctacatatg gcattccaat tttgatgcag aagatcctta cacttgtata ctctgtaatg     840
actcctctct ttaatcctct gatttatagc cttcgtaaca aggacatgaa acttgctctg     900
agaaatgttc tgttaggaat gagaattgtc aaaaatatgt aa                        942

<210> SEQ ID NO 44
<211> LENGTH: 313
<212> TYPE: PRT

-continued

<213> ORGANISM: Mus musculus

<400> SEQUENCE: 44

Met Asn Arg Ser Ala Ala His Val Thr Glu Phe Val Leu Leu Gly Phe
1               5                   10                  15

Pro Gly Ser Trp Lys Ile Gln Ile Phe Leu Phe Val Leu Phe Leu Val
            20                  25                  30

Phe Tyr Val Leu Thr Leu Leu Gly Asn Gly Ala Ile Ile Cys Ala Val
        35                  40                  45

Arg Cys Asp Ser Arg Leu His Thr Pro Met Tyr Phe Leu Leu Gly Asn
    50                  55                  60

Phe Ala Phe Leu Glu Ile Trp Tyr Val Ser Ser Thr Ile Pro Asn Ile
65                  70                  75                  80

Leu Ala Asn Ile Leu Ser Lys Thr Lys Ala Ile Ser Phe Ser Gly Cys
                85                  90                  95

Phe Leu Gln Phe Tyr Phe Phe Phe Ser Leu Gly Thr Thr Glu Cys Leu
            100                 105                 110

Phe Leu Ala Val Met Ala Tyr Asp Arg Tyr Leu Ala Ile Cys Arg Pro
        115                 120                 125

Leu His Tyr Pro Thr Ile Met Thr Arg Arg Leu Cys Cys Ile Leu Val
    130                 135                 140

Ser Ser Cys Trp Leu Ile Gly Phe Leu Gly Tyr Pro Ile Pro Ile Phe
145                 150                 155                 160

Ser Ile Ser Gln Leu Pro Phe Cys Gly Ser Asn Ile Ile Asp His Phe
                165                 170                 175

Leu Cys Asp Met Asp Pro Leu Met Ala Leu Ser Cys Ala Pro Ala Pro
            180                 185                 190

Ile Thr Glu Phe Ile Phe Tyr Ala Gln Ser Ser Phe Val Leu Phe Phe
        195                 200                 205

Thr Ile Ala Tyr Ile Leu Arg Ser Tyr Ile Leu Leu Arg Ala Val
    210                 215                 220

Phe Gln Val Pro Ser Ala Ala Gly Arg Arg Lys Ala Phe Ser Thr Cys
225                 230                 235                 240

Gly Ser His Leu Val Val Ser Leu Phe Tyr Gly Thr Val Met Val
                245                 250                 255

Met Tyr Val Ser Pro Thr Tyr Gly Ile Pro Ile Leu Met Gln Lys Ile
            260                 265                 270

Leu Thr Leu Val Tyr Ser Val Met Thr Pro Leu Phe Asn Pro Leu Ile
        275                 280                 285

Tyr Ser Leu Arg Asn Lys Asp Met Lys Leu Ala Leu Arg Asn Val Leu
    290                 295                 300

Leu Gly Met Arg Ile Val Lys Asn Met
305                 310

<210> SEQ ID NO 45
<211> LENGTH: 981
<212> TYPE: DNA
<213> ORGANISM: Homo sapiens

<400> SEQUENCE: 45
atgtgtccct tgaccttgca ggtcactggc ctaatgaatg tctctgagcc aaattccagc      60
tttgcttttg taaatgaatt tatactccaa ggtttctctt gtgagtggac aattcagatc     120
ttcctcttct cactctttac tacaacatat gcactgacta taacagggaa tggagccatt     180
gcttttgtcc tgtggtgtga ccggcgactt cacactccca tgtacatgtt cctgggaaat     240

```
ttctcctttt tagagatatg gtatgtctct tctacagttc ccaagatgtt ggtcaacttc    300
ctttcagaga aaaaaaacat ctcctttgct ggatgttttc tccagtttta tttcttcttc    360
tctttgggta catcagaatg cttgcttttg actgtgatgg cctttgatca gtaccttgct    420
atctgccgtc ccttgctcta tcctaatatc atgactgggc atctctatgc caaactggtc    480
atactgtgct gggtttgtgg atttctgtgg ttcctgatcc ccattgttct catctctcag    540
atgcccttct gtggcccaaa cattattgac catgttgtgt gtgacccagg gccacgattt    600
gcattggatt gtgtttctgc cccaagaatc caactgtttt gctacactct aagctcatta    660 gttattttg gtaacttcct ctttattatt ggatcctata tcttgtcct gaaagctatg      720 ttgggtatgc cttcaagcac tgggagacat aaggccttct ctacctgtgg gtctcatttg    780
gctgtggtat cactgtgcta tagctctctt atggtcatgt atgtgagccc aggactcgga    840
cattctacag ggatgcagaa aattgaaact ttgttctatg ctatggtgac cccactcttc    900 aatccccta tctatagcct ccagaataag gagataaagg cagccctgag gaaagttctg      960
gggagttcca acataatcta a                                               981

<210> SEQ ID NO 46
<211> LENGTH: 326
<212> TYPE: PRT
<213> ORGANISM: Homo sapiens

<400> SEQUENCE: 46
```

Met Cys Pro Leu Thr Leu Gln Val Thr Gly Leu Met Asn Val Ser Glu
1               5                   10                  15

Pro Asn Ser Ser Phe Ala Phe Val Asn Glu Phe Ile Leu Gln Gly Phe
            20                  25                  30

Ser Cys Glu Trp Thr Ile Gln Ile Phe Leu Phe Ser Leu Phe Thr Thr
        35                  40                  45

Thr Tyr Ala Leu Thr Ile Thr Gly Asn Gly Ala Ile Ala Phe Val Leu
    50                  55                  60

Trp Cys Asp Arg Arg Leu His Thr Pro Met Tyr Met Phe Leu Gly Asn
65                  70                  75                  80

Phe Ser Phe Leu Glu Ile Trp Tyr Val Ser Thr Val Pro Lys Met
                85                  90                  95

Leu Val Asn Phe Leu Ser Glu Lys Lys Asn Ile Ser Phe Ala Gly Cys
            100                 105                 110

Phe Leu Gln Phe Tyr Phe Phe Ser Leu Gly Thr Ser Glu Cys Leu
        115                 120                 125

Leu Leu Thr Val Met Ala Phe Asp Gln Tyr Leu Ala Ile Cys Arg Pro
130                 135                 140

Leu Leu Tyr Pro Asn Ile Met Thr Gly His Leu Tyr Ala Lys Leu Val
145                 150                 155                 160

Ile Leu Cys Trp Val Cys Gly Phe Leu Trp Phe Leu Ile Pro Ile Val
                165                 170                 175

Leu Ile Ser Gln Met Pro Phe Cys Gly Pro Asn Ile Ile Asp His Val
            180                 185                 190

Val Cys Asp Pro Gly Pro Arg Phe Ala Leu Asp Cys Val Ser Ala Pro
        195                 200                 205

Arg Ile Gln Leu Phe Cys Tyr Thr Leu Ser Ser Leu Val Ile Phe Gly
    210                 215                 220

Asn Phe Leu Phe Ile Ile Gly Ser Tyr Thr Leu Val Leu Lys Ala Met
225                 230                 235                 240

Leu Gly Met Pro Ser Ser Thr Gly Arg His Lys Ala Phe Ser Thr Cys
            245                 250                 255

Gly Ser His Leu Ala Val Val Ser Leu Cys Tyr Ser Ser Leu Met Val
        260                 265                 270

Met Tyr Val Ser Pro Gly Leu Gly His Ser Thr Gly Met Gln Lys Ile
    275                 280                 285

Glu Thr Leu Phe Tyr Ala Met Val Thr Pro Leu Phe Asn Pro Leu Ile
290                 295                 300

Tyr Ser Leu Gln Asn Lys Glu Ile Lys Ala Ala Leu Arg Lys Val Leu
305                 310                 315                 320

Gly Ser Ser Asn Ile Ile
            325

<210> SEQ ID NO 47
<211> LENGTH: 948
<212> TYPE: DNA
<213> ORGANISM: Homo sapiens

<400> SEQUENCE: 47

```
atgaatgtct ctgagccaaa ttccagcttt gcttttgtaa atgaatttat actccaaggt      60
ttctcttgtg agtggacaat tcagatcttc ctcttctcac tctttactac aatatatgca     120
ctgactataa cagggaatgg agccattgct tttgtcctgt ggtgtgaccg gcgacttcac     180
actcccatgt acatgttcct gggaaatttc tcctttttag agatatggta tgtctcttct     240
acagttccca agatgttggt caacttcctt tcagagaaaa aaaacatctc ctttgctgga     300
tgttttctcc agttttattt cttcttctct tgggtacat cagaatgctt gcttttgact     360
gtgatggcct tgatcagta ccttgctatc tgccgtccct tgctctatcc taatatcatg     420
actgggcatc tctatgccaa actggtcata ctgtgctggg tttgtggatt tctgtggttc     480
ctgatcccca ttgttctcat ctctcagaag cccttctgtg cccaaacat tattgaccat     540
gttgtgtgtg acccagggcc actatttgca ttggattgtg tttctgcccc aagaatccaa     600
ctgttttgct acactctaag ctcattagtt attttttggta acttcctctt tattattgga     660
tcctatactc ttgtcctgaa agctgtgttg ggtatgcctt caagcactgg gagacataag     720
gccttctcta cctgtgggtc tcatttggct gtggtatcac tgtgctatag ccctcttatg     780
gtcatgtatg tgagcccagg actcggacat tctacaggga tgcagaaaat tgaaactttg     840
ttctatgcta tggtgacccc actcttcaat ccccttatct atagcctcca gaataaggag     900
ataaaggcag ccctgaggaa agttctgggg agttccaaca taatctaa                948
```

<210> SEQ ID NO 48
<211> LENGTH: 315
<212> TYPE: PRT
<213> ORGANISM: Homo sapiens

<400> SEQUENCE: 48

Met Asn Val Ser Glu Pro Asn Ser Ser Phe Ala Phe Val Asn Glu Phe
1               5                   10                  15

Ile Leu Gln Gly Phe Ser Cys Glu Trp Thr Ile Gln Ile Phe Leu Phe
            20                  25                  30

Ser Leu Phe Thr Thr Ile Tyr Ala Leu Thr Ile Thr Gly Asn Gly Ala
        35                  40                  45

Ile Ala Phe Val Leu Trp Cys Asp Arg Arg Leu His Thr Pro Met Tyr
    50                  55                  60

```
Met Phe Leu Gly Asn Phe Ser Phe Leu Glu Ile Trp Tyr Val Ser Ser
 65                  70                  75                  80

Thr Val Pro Lys Met Leu Val Asn Phe Leu Ser Glu Lys Lys Asn Ile
                 85                  90                  95

Ser Phe Ala Gly Cys Phe Leu Gln Phe Tyr Phe Phe Ser Leu Gly
            100                 105                 110

Thr Ser Glu Cys Leu Leu Leu Thr Val Met Ala Phe Asp Gln Tyr Leu
            115                 120                 125

Ala Ile Cys Arg Pro Leu Leu Tyr Pro Asn Ile Met Thr Gly His Leu
130                 135                 140

Tyr Ala Lys Leu Val Ile Leu Cys Trp Val Cys Gly Phe Leu Trp Phe
145                 150                 155                 160

Leu Ile Pro Ile Val Leu Ile Ser Gln Lys Pro Phe Cys Gly Pro Asn
                165                 170                 175

Ile Ile Asp His Val Cys Asp Pro Gly Pro Leu Phe Ala Leu Asp
            180                 185                 190

Cys Val Ser Ala Pro Arg Ile Gln Leu Phe Cys Tyr Thr Leu Ser Ser
            195                 200                 205

Leu Val Ile Phe Gly Asn Phe Leu Phe Ile Ile Gly Ser Tyr Thr Leu
210                 215                 220

Val Leu Lys Ala Val Leu Gly Met Pro Ser Ser Thr Gly Arg His Lys
225                 230                 235                 240

Ala Phe Ser Thr Cys Gly Ser His Leu Ala Val Val Ser Leu Cys Tyr
                245                 250                 255

Ser Pro Leu Met Val Met Tyr Val Ser Pro Gly Leu Gly His Ser Thr
            260                 265                 270

Gly Met Gln Lys Ile Glu Thr Leu Phe Tyr Ala Met Val Thr Pro Leu
            275                 280                 285

Phe Asn Pro Leu Ile Tyr Ser Leu Gln Asn Lys Glu Ile Lys Ala Ala
            290                 295                 300

Leu Arg Lys Val Leu Gly Ser Ser Asn Ile Ile
305                 310                 315

<210> SEQ ID NO 49
<211> LENGTH: 975
<212> TYPE: DNA
<213> ORGANISM: Homo sapiens

<400> SEQUENCE: 49
atgtctttct ctttgtaga cttaagaccc atgaacaggt cagcaacaca catcgtgaca      60
gagtttattc tcctgggatt ccctggttgc tggaagattc agattttcct cttctcattg    120
tttttggtga tttatgtctt gaccttgctg ggaaatggag ccatcatcta tgcagtgaga    180
tgcaacccac tactacacac ccccatgtac tttctgctgg gaaattttgc cttccttgag    240
atctggtatg tgtcctccac tattcctaac atgctagtca acattctctc caagaccaag    300
gccatctcat tttctgggtg cttcctccag ttctatttct cttttcact gggaacaact     360 gaatgtctct ttctggcagt aatggcttat gatcgatacc tggccatctg ccacccactg    420
cagtaccctg ccatcatgac tgtaaggttc tgtggtaagc tggtgtcttt ctgttggctt    480
attggattcc ttggataccc aattcccatt tctacatct cccaactccc cttctgtggt     540
cctaatatca ttgatcactt cctgtgtgac atggacccat tgatggctct atcctgtgcc    600
ccagctccca taactgaatg tattttctat actcagagct cccttgtcct cttttttcact   660 agtatgtaca ttcttcgatc ctatatcctg ttactaacag ctgttttca ggtcccttct     720
```

```
gcagctggtc ggagaaaagc cttctctacc tgtggttctc atttggttgt ggtatctctt    780
ttctatggga cagtcatggt aatgtatgta agtcctacat atgggatccc aactttattg    840
cagaagatcc tcacactggt atattcagta acgactcctc tttttaatcc tctgatctat    900
actcttcgta ataaggacat gaaactcgct ctgagaaatg tcctgtttgg aatgagaatt    960
cgtcaaaatt cgtga                                                    975
```

<210> SEQ ID NO 50
<211> LENGTH: 324
<212> TYPE: PRT
<213> ORGANISM: Homo sapiens

<400> SEQUENCE: 50

```
Met Ser Phe Phe Phe Val Asp Leu Arg Pro Met Asn Arg Ser Ala Thr
1               5                   10                  15

His Ile Val Thr Glu Phe Ile Leu Leu Gly Phe Pro Gly Cys Trp Lys
            20                  25                  30

Ile Gln Ile Phe Leu Phe Ser Leu Phe Leu Val Ile Tyr Val Leu Thr
        35                  40                  45

Leu Leu Gly Asn Gly Ala Ile Ile Tyr Ala Val Arg Cys Asn Pro Leu
    50                  55                  60

Leu His Thr Pro Met Tyr Phe Leu Leu Gly Asn Phe Ala Phe Leu Glu
65                  70                  75                  80

Ile Trp Tyr Val Ser Ser Thr Ile Pro Asn Met Leu Val Asn Ile Leu
                85                  90                  95

Ser Lys Thr Lys Ala Ile Ser Phe Ser Gly Cys Phe Leu Gln Phe Tyr
            100                 105                 110

Phe Phe Phe Ser Leu Gly Thr Thr Glu Cys Leu Phe Leu Ala Val Met
        115                 120                 125

Ala Tyr Asp Arg Tyr Leu Ala Ile Cys His Pro Leu Gln Tyr Pro Ala
    130                 135                 140

Ile Met Thr Val Arg Phe Cys Gly Lys Leu Val Ser Phe Cys Trp Leu
145                 150                 155                 160

Ile Gly Phe Leu Gly Tyr Pro Ile Pro Ile Phe Tyr Ile Ser Gln Leu
                165                 170                 175

Pro Phe Cys Gly Pro Asn Ile Ile Asp His Phe Leu Cys Asp Met Asp
            180                 185                 190

Pro Leu Met Ala Leu Ser Cys Ala Pro Ala Pro Ile Thr Glu Cys Ile
        195                 200                 205

Phe Tyr Thr Gln Ser Ser Leu Val Leu Phe Phe Thr Ser Met Tyr Ile
    210                 215                 220

Leu Arg Ser Tyr Ile Leu Leu Thr Ala Val Phe Gln Val Pro Ser
225                 230                 235                 240

Ala Ala Gly Arg Arg Lys Ala Phe Ser Thr Cys Gly Ser His Leu Val
                245                 250                 255

Val Val Ser Leu Phe Tyr Gly Thr Val Met Val Met Tyr Val Ser Pro
            260                 265                 270

Thr Tyr Gly Ile Pro Thr Leu Leu Gln Lys Ile Leu Thr Leu Val Tyr
        275                 280                 285

Ser Val Thr Thr Pro Leu Phe Asn Pro Leu Ile Tyr Thr Leu Arg Asn
    290                 295                 300

Lys Asp Met Lys Leu Ala Leu Arg Asn Val Leu Phe Gly Met Arg Ile
305                 310                 315                 320
```

-continued

Arg Gln Asn Ser

<210> SEQ ID NO 51
<211> LENGTH: 942
<212> TYPE: DNA
<213> ORGANISM: Homo sapiens

<400> SEQUENCE: 51

| | | | | | |
|---|---|---|---|---|---|
| atgaataact | cacagatatc | tactgtgacg | cagtttgtgt | tgttggggtt | tcctggtccc | 60 |
| tggaaaattc | agatcatctt | tttctcaatg | attttgttgg | tctacatctt | cactctgact | 120 |
| gggaatatgg | ccatcatctg | tgcagtgagg | tgggaccatc | gactccatac | ccctatgtac | 180 |
| gtgctcctag | ccaacttctc | cttcctagag | atctggtatg | tgacctgcac | agtccccaac | 240 |
| atgctggtaa | attttttctc | caaaactaag | accatatcat | tctctggatg | tttcactcag | 300 |
| ttccacttct | tcttttccct | gggcacaact | gaatgcttct | tcctctgtgt | catggcttat | 360 |
| gatcggtacc | tggccatctg | ccacccactg | cactatccct | ccattatgac | tggccagctc | 420 |
| tgtggcatct | tggtgtctct | tgttggctc | attggtttcc | ttggacattc | aatttccatt | 480 |
| ttcttcattt | ttcaactacc | tttctgtggt | cccaacatca | ttgatcattt | tctgtgtgat | 540 |
| gtagacccac | tgatggcatt | gtcctctgcc | cctactcaca | tcatagggca | tgtgttccat | 600 |
| tctgtgagct | ctcttttcat | caacctcacc | atggtgtaca | tccttgggtc | ctataccttg | 660 |
| gtgctcagaa | ctgtgcttca | ggttccttct | tcagctggat | ggcaaaaggc | catctctacc | 720 |
| tgtgggtcac | acttggttgt | tgtgtctctg | ttctatggag | ccataatgct | gatgtatgtg | 780 |
| agtcccacac | ctggcaactc | agttgctatg | cataagctca | tcacactgat | atattctgtg | 840 |
| gtaacacctg | tcttaaaccc | cctcatctac | agcctacgca | acaaggacat | gaaatatgcc | 900 |
| ctccatcatg | tcttctgtgg | aatgagaatt | atccagagat | ca | | 942 |

<210> SEQ ID NO 52
<211> LENGTH: 314
<212> TYPE: PRT
<213> ORGANISM: Homo sapiens

<400> SEQUENCE: 52

Met Asn Asn Ser Gln Ile Ser Thr Val Thr Gln Phe Val Leu Leu Gly
1               5                   10                  15

Phe Pro Gly Pro Trp Lys Ile Gln Ile Ile Phe Phe Ser Met Ile Leu
            20                  25                  30

Leu Val Tyr Ile Phe Thr Leu Thr Gly Asn Met Ala Ile Ile Cys Ala
        35                  40                  45

Val Arg Trp Asp His Arg Leu His Thr Pro Met Tyr Val Leu Leu Ala
    50                  55                  60

Asn Phe Ser Phe Leu Glu Ile Trp Tyr Val Thr Cys Thr Val Pro Asn
65                  70                  75                  80

Met Leu Val Asn Phe Ser Lys Thr Lys Thr Ile Ser Phe Ser Gly
                85                  90                  95

Cys Phe Thr Gln Phe His Phe Phe Ser Leu Gly Thr Thr Glu Cys
            100                 105                 110

Phe Phe Leu Cys Val Met Ala Tyr Asp Arg Tyr Leu Ala Ile Cys His
        115                 120                 125

Pro Leu His Tyr Pro Ser Ile Met Thr Gly Gln Leu Cys Gly Ile Leu
    130                 135                 140

Val Ser Leu Cys Trp Leu Ile Gly Phe Leu Gly His Ser Ile Ser Ile
145                 150                 155                 160

```
Phe Phe Ile Phe Gln Leu Pro Phe Cys Gly Pro Asn Ile Ile Asp His
                165                 170                 175
Phe Leu Cys Asp Val Asp Pro Leu Met Ala Leu Ser Ser Ala Pro Thr
            180                 185                 190
His Ile Ile Gly His Val Phe His Ser Val Ser Leu Phe Ile Asn
        195                 200                 205
Leu Thr Met Val Tyr Ile Leu Gly Ser Tyr Thr Leu Val Leu Arg Thr
    210                 215                 220
Val Leu Gln Val Pro Ser Ser Ala Gly Trp Gln Lys Ala Ile Ser Thr
225                 230                 235                 240
Cys Gly Ser His Leu Val Val Val Ser Leu Phe Tyr Gly Ala Ile Met
                245                 250                 255
Leu Met Tyr Val Ser Pro Thr Pro Gly Asn Ser Val Ala Met His Lys
            260                 265                 270
Leu Ile Thr Leu Ile Tyr Ser Val Val Thr Pro Val Leu Asn Pro Leu
        275                 280                 285
Ile Tyr Ser Leu Arg Asn Lys Asp Met Lys Tyr Ala Leu His His Val
    290                 295                 300
Phe Cys Gly Met Arg Ile Ile Gln Arg Ser
305                 310
```

<210> SEQ ID NO 53
<211> LENGTH: 981
<212> TYPE: DNA
<213> ORGANISM: Homo sapiens

<400> SEQUENCE: 53

```
atgtgtccct tgaccttgca ggtcactggc ctaatgaatg tctctgagcc aaattccagc    60
tttgcttttg taaatgaatt tatactccaa ggtttcactt gtgagtggac aattcagatc   120
ttcctcttct cactctttac tacaacatat gcactgacta aacagggaa tggagccatt    180
gcttttgtcc tgtggtgtga ctggcgactt cacactccca tgtacatgtt cctgggaaat   240
ttctcctttt tagagatatg gtatgtctct tctacagttc ccaagatgtt ggtcaacttc   300
ctttcagaga aaaaaaacat ctcctttgct ggatgttttc tccagtttta tttcttcttc   360
tctttgggta catcagaatg cttgcttttg actgtgatgg cctttgatca gtaccttgct   420
atctgccgtc ccttgctcta tcctaatatc atgactgggc atctctgtgc aaactggtc   480
atactgtgct gggtttgtgg atttctgtgg ttcctgatcc ccattgttct catctctcag   540
atgcccttct gtggcccaaa cattattgac catgttgtgt gtgacccagg ccacgattt   600
gcattggatt gtgtttctgc cccaagaatc caactgtttt gctacactct aagctcatta   660
gttattttg gtaacttcct ctttattatt ggatcctata ctcttgtcct gaaagctgtg   720
ttgggtatgc cttcaagcac tgggagacat aaggccttct ctacctgtgg gtctcatttg   780
gctgtggtat cactgtgcta tagctctctt atggtcatgt atgtgagccc aggactcgga   840
cattctacag ggatgcagaa aattgaaact tgttctatg ctatggtgac cccactcttc   900
aatcccctta tctatagcct ccagaataag gagataaagg cagccctgag gaaagttctg   960
ggaagttcca acataatcta a                                              981
```

<210> SEQ ID NO 54
<211> LENGTH: 326
<212> TYPE: PRT
<213> ORGANISM: Homo sapiens

<400> SEQUENCE: 54

```
Met Cys Pro Leu Thr Leu Gln Val Thr Gly Leu Met Asn Val Ser Glu
 1               5                  10                  15
Pro Asn Ser Ser Phe Ala Phe Val Asn Glu Phe Ile Leu Gln Gly Phe
             20                  25                  30
Thr Cys Glu Trp Thr Ile Gln Ile Phe Leu Phe Ser Leu Phe Thr Thr
         35                  40                  45
Thr Tyr Ala Leu Thr Ile Thr Gly Asn Gly Ala Ile Ala Phe Val Leu
     50                  55                  60
Trp Cys Asp Trp Arg Leu His Thr Pro Met Tyr Met Phe Leu Gly Asn
 65                  70                  75                  80
Phe Ser Phe Leu Glu Ile Trp Tyr Val Ser Ser Thr Val Pro Lys Met
                 85                  90                  95
Leu Val Asn Phe Leu Ser Glu Lys Lys Asn Ile Ser Phe Ala Gly Cys
            100                 105                 110
Phe Leu Gln Phe Tyr Phe Phe Phe Ser Leu Gly Thr Ser Glu Cys Leu
        115                 120                 125
Leu Leu Thr Val Met Ala Phe Asp Gln Tyr Leu Ala Ile Cys Arg Pro
    130                 135                 140
Leu Leu Tyr Pro Asn Ile Met Thr Gly His Leu Cys Ala Lys Leu Val
145                 150                 155                 160
Ile Leu Cys Trp Val Cys Gly Phe Leu Trp Phe Leu Ile Pro Ile Val
                165                 170                 175
Leu Ile Ser Gln Met Pro Phe Cys Gly Pro Asn Ile Ile Asp His Val
            180                 185                 190
Val Cys Asp Pro Gly Pro Arg Phe Ala Leu Asp Cys Val Ser Ala Pro
        195                 200                 205
Arg Ile Gln Leu Phe Cys Tyr Thr Leu Ser Ser Leu Val Ile Phe Gly
    210                 215                 220
Asn Phe Leu Phe Ile Ile Gly Ser Tyr Thr Leu Val Leu Lys Ala Val
225                 230                 235                 240
Leu Gly Met Pro Ser Ser Thr Gly Arg His Lys Ala Phe Ser Thr Cys
                245                 250                 255
Gly Ser His Leu Ala Val Val Ser Leu Cys Tyr Ser Ser Leu Met Val
            260                 265                 270
Met Tyr Val Ser Pro Gly Leu Gly His Ser Thr Gly Met Gln Lys Ile
        275                 280                 285
Glu Thr Leu Phe Tyr Ala Met Val Thr Pro Leu Phe Asn Pro Leu Ile
    290                 295                 300
Tyr Ser Leu Gln Asn Lys Glu Ile Lys Ala Ala Leu Arg Lys Val Leu
305                 310                 315                 320
Gly Ser Ser Asn Ile Ile
                325
```

<210> SEQ ID NO 55
<211> LENGTH: 957
<212> TYPE: DNA
<213> ORGANISM: Mus musculus

<400> SEQUENCE: 55

```
atgtctggag ccaacagctc cagcctgact ccagaattct ttatcctgaa tggtgttcct      60
gggctggaag atgcacatgt ctggatctct ctgccattct gcttcatgta catgattgct     120
gtagtgggga actgtgggct tatctacctc attggccatg aggaggctct gcaccggccc     180
```

```
atgtactact tcctggcttt actttccttc actgatgtca ccttgtgtac aaccacagtg    240
cccaatatgc tgtgtatatt ctggttcaat ttcaagaaga ttggatttaa ttcctgcctt    300
gtccagatgt tctttgtcca catgttgact ggaatggagt ctggtgtgct catgctcatg    360
gccctggacc gctatgtagc catctgctat cctctacgat atactaccat cctcacaaac    420
cctgtgattg ccaaggctgg tcttgcaaca ttcttaagga gtgtaatgct catctttcca    480
ttcactctcc tcaccaagcg cttgccctat gcagaggca gtcttatccc ccacacttac    540
tgtgaccaca tgtctgtggc caaggtatcc tgtggcaatg ccaaggtcaa tgcaatctat    600
ggcctcatgg ttgctctatt gattggtgtg tttgacattt gttgtatctc tgtgtcttac    660
actatgatat tgagggcagt ggtgagcctg tcctctgctg atgctcgtca caaggccttc    720
agcacctgta catctcacat ctgtgctatt gtgatcactt atgtgcctgc ctttttact    780 tttttcactc atcgttttgg aggacacact attccccacc atgtccacat catagtggct    840
aacctctacc tgctactgcc ccctaccatg aacccaattg tttatggagt caagaccaag    900
cagattcggg aaagtgtaat caagttttta cttggagata aatgggcat tacctag      957

<210> SEQ ID NO 56
<211> LENGTH: 318
<212> TYPE: PRT
<213> ORGANISM: Mus musculus

<400> SEQUENCE: 56

Met Ser Gly Ala Asn Ser Ser Leu Thr Pro Glu Phe Phe Ile Leu
1               5                   10                  15

Asn Gly Val Pro Gly Leu Glu Asp Ala His Val Trp Ile Ser Leu Pro
                20                  25                  30

Phe Cys Phe Met Tyr Met Ile Ala Val Val Gly Asn Cys Gly Leu Ile
            35                  40                  45

Tyr Leu Ile Gly His Glu Glu Ala Leu His Arg Pro Met Tyr Tyr Phe
    50                  55                  60

Leu Ala Leu Leu Ser Phe Thr Asp Val Thr Leu Cys Thr Thr Thr Val
65                  70                  75                  80

Pro Asn Met Leu Cys Ile Phe Trp Phe Asn Phe Lys Lys Ile Gly Phe
                85                  90                  95

Asn Ser Cys Leu Val Gln Met Phe Phe Val His Met Leu Thr Gly Met
            100                 105                 110

Glu Ser Gly Val Leu Met Leu Met Ala Leu Asp Arg Tyr Val Ala Ile
        115                 120                 125

Cys Tyr Pro Leu Arg Tyr Thr Thr Ile Leu Thr Asn Pro Val Ile Ala
    130                 135                 140

Lys Ala Gly Leu Ala Thr Phe Leu Arg Ser Val Met Leu Ile Phe Pro
145                 150                 155                 160

Phe Thr Leu Leu Thr Lys Arg Leu Pro Tyr Cys Arg Gly Ser Leu Ile
                165                 170                 175

Pro His Thr Tyr Cys Asp His Met Ser Val Ala Lys Val Ser Cys Gly
            180                 185                 190

Asn Ala Lys Val Asn Ala Ile Tyr Gly Leu Met Val Ala Leu Leu Ile
        195                 200                 205

Gly Val Phe Asp Ile Cys Cys Ile Ser Val Ser Tyr Thr Met Ile Leu
    210                 215                 220

Arg Ala Val Val Ser Leu Ser Ser Ala Asp Ala Arg His Lys Ala Phe
225                 230                 235                 240
```

```
Ser Thr Cys Thr Ser His Ile Cys Ala Ile Val Ile Thr Tyr Val Pro
                245                 250                 255

Ala Phe Phe Thr Phe Phe Thr His Arg Phe Gly Gly His Thr Ile Pro
            260                 265                 270

His His Val His Ile Ile Val Ala Asn Leu Tyr Leu Leu Pro Pro
        275                 280                 285

Thr Met Asn Pro Ile Val Tyr Gly Val Lys Thr Lys Gln Ile Arg Glu
    290                 295                 300

Ser Val Ile Lys Phe Leu Leu Gly Asp Lys Met Gly Ile Thr
305                 310                 315

<210> SEQ ID NO 57
<211> LENGTH: 981
<212> TYPE: DNA
<213> ORGANISM: Mus musculus

<400> SEQUENCE: 57
atgtctgaag ccaacagctc cagcctgacc ccagaattct ttatactgaa tggtatccgt      60
gggctggaag atgcacatgt ctggatctct ctgccattct gtttcatgta catgattgct     120
gtggtgggga actgtgggct tatctacctc attggccatg aggaggctct gcaccggccc     180
atgtactact ttctaaccct gctctccttc actgatataa ccttatgtac cactactgta     240
cccaatatgc tgtgtatatt ctggttcaac ctcaagaaga ttggatttaa agcctgcctg     300
gcccagatgt tctttgtgca taccttcaca gcaacagagt ctggcatgct aatgctcatg     360
gccctggatc gctatgtggc catctgctat cctttgcgct acgggaccat cctgaccaac     420
cctgtgattg ccaaagctag tcttgctact ttcttgagga gtgtggcatt catccttcct     480
ttcactttcc tcactaagcg cctgcccat tgccgaggaa acctcatccc ccatgcctac     540
tgtgaccaca tgtctgtggc caagatatcc tgtggcaatg tgaaaatcaa tgcagtctat     600
ggtctgctgg ttgctcttgt ggtttgtgca tttgacatat tctgtatcac tgtgtcatac     660
acaatgatat tgagagcagt gatgaacctg tcttctgctg atgctcgtca caaggccttc     720
agcacctgca catctcacat ctgtgctatt gtgatcactt atgtgcctgc ttttttaat     780 ttcttcactc atcgttttgg agcacatact attccccacc acatccacat catagtggca     840
aacctctatc tgttattgcc tgctaccatg aacccaattg tttatggagt caagaccaag     900
cagattcggg agagtgtaat caaatttttt agtggagaca gagtgacat tgttgatata      960 aaaggattaa aaacaagtg a                                                981

<210> SEQ ID NO 58
<211> LENGTH: 326
<212> TYPE: PRT
<213> ORGANISM: Mus musculus

<400> SEQUENCE: 58

Met Ser Glu Ala Asn Ser Ser Ser Leu Thr Pro Glu Phe Phe Ile Leu
1               5                   10                  15

Asn Gly Ile Arg Gly Leu Glu Asp Ala His Val Trp Ile Ser Leu Pro
            20                  25                  30

Phe Cys Phe Met Tyr Met Ile Ala Val Val Gly Asn Cys Gly Leu Ile
        35                  40                  45

Tyr Leu Ile Gly His Glu Glu Ala Leu His Arg Pro Met Tyr Tyr Phe
    50                  55                  60

Leu Thr Leu Leu Ser Phe Thr Asp Ile Thr Leu Cys Thr Thr Thr Val
65                  70                  75                  80
```

Pro Asn Met Leu Cys Ile Phe Trp Phe Asn Leu Lys Lys Ile Gly Phe
            85                  90                  95
Lys Ala Cys Leu Ala Gln Met Phe Phe Val His Thr Phe Thr Ala Thr
            100                 105                 110
Glu Ser Gly Met Leu Met Leu Met Ala Leu Asp Arg Tyr Val Ala Ile
            115                 120                 125
Cys Tyr Pro Leu Arg Tyr Gly Thr Ile Leu Thr Asn Pro Val Ile Ala
130                 135                 140
Lys Ala Ser Leu Ala Thr Phe Leu Arg Ser Val Ala Phe Ile Leu Pro
145                 150                 155                 160
Phe Thr Phe Leu Thr Lys Arg Leu Pro Tyr Cys Arg Gly Asn Leu Ile
            165                 170                 175
Pro His Ala Tyr Cys Asp His Met Ser Val Ala Lys Ile Ser Cys Gly
            180                 185                 190
Asn Val Lys Ile Asn Ala Val Tyr Gly Leu Leu Val Ala Leu Val Val
            195                 200                 205
Cys Ala Phe Asp Ile Phe Cys Ile Thr Val Ser Tyr Thr Met Ile Leu
210                 215                 220
Arg Ala Val Met Asn Leu Ser Ser Ala Asp Ala Arg His Lys Ala Phe
225                 230                 235                 240
Ser Thr Cys Thr Ser His Ile Cys Ala Ile Val Ile Thr Tyr Val Pro
            245                 250                 255
Ala Phe Phe Asn Phe Phe Thr His Arg Phe Gly Ala His Thr Ile Pro
            260                 265                 270
His His Ile His Ile Ile Val Ala Asn Leu Tyr Leu Leu Leu Pro Ala
            275                 280                 285
Thr Met Asn Pro Ile Val Tyr Gly Val Lys Thr Lys Gln Ile Arg Glu
            290                 295                 300
Ser Val Ile Lys Phe Phe Ser Gly Asp Lys Ser Asp Ile Val Asp Ile
305                 310                 315                 320
Lys Gly Leu Lys Asn Lys
            325

<210> SEQ ID NO 59
<211> LENGTH: 957
<212> TYPE: DNA
<213> ORGANISM: Mus musculus

<400> SEQUENCE: 59

```
atgtctggag ccaatagctc cagcttgacc ccagaattct ttatcctgaa tggtgttcct      60
gggctggaag atgcacatgt ctggatctct ctgccattct gcttcatgta catgattgct     120
gtggtgggga actgtgggct tatctacctc attggccatg aggaggctct gcaccggccc     180
atgttctact ccctggcctt actctccttc actgatgtta cctggtgtac taccactgtg     240
cccaatatgc tgtgtatatt ctggttcaat ttcaagaaga ttggatttaa ttcctgcctt     300
gcccaaatgt tctttgttca tatgttgact ggaatggagt ctggtgtgct catgctcatg     360
gccctggacc gctatgtagc catctgcaat cctctacgat atactaccat cctcaccaac     420
cctgtgattg ccaaggcttg tcttgcaaca ttcttgagga gtgtaatgct catctttcca     480
ttcactctcc tcaccaagcg cttgccctat gtagaagca ttcttatccc ccatacttac     540
tgtgaccaca gtctgtggc caaggtatcc tgtggcaatg ccaaggtcaa tgcaatctat     600
ggcctcatgg ttgcttatt gattggtgtg tttgatattt gttgtatctc tgtgtcttac     660
```

```
actatgatat tgagagcagt ggtgagtctg tcctctgctg atgctcgtca caaggccttc    720
agcacctgta catctcacat ctgtgctatt gtgatcactt atgtgcctgc ctttttact     780 tttttcactc atcgttttgg aggacacact attccccacc atgtccacat catagtggct    840
aacctctacc tgctactgcc ccctaccatg aacccaattg tttatggagt caagaccaag    900
cagattcggg aaagtgtaat caagttttta cttggagaca aatgggtttt tacctaa       957
```

<210> SEQ ID NO 60
<211> LENGTH: 318
<212> TYPE: PRT
<213> ORGANISM: Mus musculus

<400> SEQUENCE: 60

```
Met Ser Gly Ala Asn Ser Ser Leu Thr Pro Glu Phe Phe Ile Leu
1               5                   10                  15

Asn Gly Val Pro Gly Leu Glu Asp Ala His Val Trp Ile Ser Leu Pro
                20                  25                  30

Phe Cys Phe Met Tyr Met Ile Ala Val Val Gly Asn Cys Gly Leu Ile
            35                  40                  45

Tyr Leu Ile Gly His Glu Glu Ala Leu His Arg Pro Met Phe Tyr Phe
50                  55                  60

Leu Ala Leu Leu Ser Phe Thr Asp Val Thr Trp Cys Thr Thr Thr Val
65                  70                  75                  80

Pro Asn Met Leu Cys Ile Phe Trp Phe Asn Phe Lys Lys Ile Gly Phe
                85                  90                  95

Asn Ser Cys Leu Ala Gln Met Phe Phe Val His Met Leu Thr Gly Met
            100                 105                 110

Glu Ser Gly Val Leu Met Leu Met Ala Leu Asp Arg Tyr Val Ala Ile
        115                 120                 125

Cys Asn Pro Leu Arg Tyr Thr Thr Ile Leu Thr Asn Pro Val Ile Ala
130                 135                 140

Lys Ala Cys Leu Ala Thr Phe Leu Arg Ser Val Met Leu Ile Phe Pro
145                 150                 155                 160

Phe Thr Leu Leu Thr Lys Arg Leu Pro Tyr Cys Arg Ser Ile Leu Ile
                165                 170                 175

Pro His Thr Tyr Cys Asp His Met Ser Val Ala Lys Val Ser Cys Gly
            180                 185                 190

Asn Ala Lys Val Asn Ala Ile Tyr Gly Leu Met Val Ala Leu Leu Ile
        195                 200                 205

Gly Val Phe Asp Ile Cys Cys Ile Ser Val Ser Tyr Thr Met Ile Leu
210                 215                 220

Arg Ala Val Val Ser Leu Ser Ser Ala Asp Ala Arg His Lys Ala Phe
225                 230                 235                 240

Ser Thr Cys Thr Ser His Ile Cys Ala Ile Val Ile Thr Tyr Val Pro
                245                 250                 255

Ala Phe Phe Thr Phe Thr His Arg Phe Gly Gly His Thr Ile Pro
            260                 265                 270

His His Val His Ile Ile Val Ala Asn Leu Tyr Leu Leu Pro Pro
        275                 280                 285

Thr Met Asn Pro Ile Val Tyr Gly Val Lys Thr Lys Gln Ile Arg Glu
        290                 295                 300

Ser Val Ile Lys Phe Leu Leu Gly Asp Lys Met Gly Phe Thr
305                 310                 315
```

<210> SEQ ID NO 61
<211> LENGTH: 954
<212> TYPE: DNA
<213> ORGANISM: Mus musculus

<400> SEQUENCE: 61

```
atgctgattt ccaacaactc atatgaagcc ccgcagtctt tcattcttaa tggaattcct      60
ggtctcgaag cagtgcatat atggatctct cttccactct gtacaatgta catcatctcc     120
ctagtaggca accttggcct tgtatatctc atttactatg aggaatcctt acatcgccca     180
atgtatttct ttctggccat gctttctctc atagacctgt ttacttgcac aaccactgtc     240
cccaatgccc tcttcatttt ctggttcaaa ctcaaggaaa ttaacttcac tgcttgccta     300
gttcagatgt tctttgtgca cggattcaca ggtgtggagt ctggggtact catgctcatg     360
gccttggacc gctatgtggc catttgctac ccactacgct atgcaaccat acttaccaac     420
cctgtcattg ccaaagctgg gcttgccacc ttcttgagag gtgtgttact gatgattcct     480
tttccattct tggttaaacg tttgcccttc tgccgaagca atgtcatctc ccatacatat     540
tgtgaccaca tgtctgtggt aaagttatcc tgtgccagca tcaaaatcaa tgtcatctat     600
ggtctcatgg ttgcacttct gattggagtg tttgacatat gttgtatatc tgtgtcctac     660
actatgatcc tccgggcagt ggtcagcctg tcctctgcag atgctcggca gaaggccttc     720
agcacctgca cagcccacat atctgccatc atcattactt atgttccagc cttcttcacc     780
ttctttactc atcgttttgg aggtcacacc atccctcctt ctcttcatat cattgtggct     840
aatctttatc ttcttctccc tccaactcta aatcccattg tttatgggat gaagaccaaa     900
cagatcagag atagtatcat taaattcttt cacggtgaaa aaggttcaag gtga           954
```

<210> SEQ ID NO 62
<211> LENGTH: 317
<212> TYPE: PRT
<213> ORGANISM: Mus musculus

<400> SEQUENCE: 62

```
Met Leu Ile Ser Asn Asn Ser Tyr Glu Ala Pro Gln Ser Phe Ile Leu
1               5                   10                  15

Asn Gly Ile Pro Gly Leu Glu Ala Val His Ile Trp Ile Ser Leu Pro
            20                  25                  30

Leu Cys Thr Met Tyr Ile Ile Ser Leu Val Gly Asn Leu Gly Leu Val
        35                  40                  45

Tyr Leu Ile Tyr Tyr Glu Glu Ser Leu His Arg Pro Met Tyr Phe Phe
    50                  55                  60

Leu Ala Met Leu Ser Leu Ile Asp Leu Phe Thr Cys Thr Thr Thr Val
65                  70                  75                  80

Pro Asn Ala Leu Phe Ile Phe Trp Phe Lys Leu Lys Glu Ile Asn Phe
                85                  90                  95

Thr Ala Cys Leu Val Gln Met Phe Phe Val His Gly Phe Thr Gly Val
            100                 105                 110

Glu Ser Gly Val Leu Met Leu Met Ala Leu Asp Arg Tyr Val Ala Ile
        115                 120                 125

Cys Tyr Pro Leu Arg Tyr Ala Thr Ile Leu Thr Asn Pro Val Ile Ala
    130                 135                 140

Lys Ala Gly Leu Ala Thr Phe Leu Arg Gly Val Leu Leu Met Ile Pro
145                 150                 155                 160

Phe Pro Phe Leu Val Lys Arg Leu Pro Phe Cys Arg Ser Asn Val Ile
                165                 170                 175
```

Ser His Thr Tyr Cys Asp His Met Ser Val Val Lys Leu Ser Cys Ala
            180                 185                 190

Ser Ile Lys Ile Asn Val Ile Tyr Gly Leu Met Val Ala Leu Leu Ile
            195                 200                 205

Gly Val Phe Asp Ile Cys Cys Ile Ser Val Ser Tyr Thr Met Ile Leu
210                 215                 220

Arg Ala Val Val Ser Leu Ser Ser Ala Asp Ala Arg Gln Lys Ala Phe
225                 230                 235                 240

Ser Thr Cys Thr Ala His Ile Ser Ala Ile Ile Thr Tyr Val Pro
            245                 250                 255

Ala Phe Phe Thr Phe Phe Thr His Arg Phe Gly Gly Thr His Thr Ile Pro
            260                 265                 270

Pro Ser Leu His Ile Ile Val Ala Asn Leu Tyr Leu Leu Leu Pro Pro
            275                 280                 285

Thr Leu Asn Pro Ile Val Tyr Gly Met Lys Thr Lys Gln Ile Arg Asp
            290                 295                 300

Ser Ile Ile Lys Phe Phe His Gly Glu Lys Gly Ser Arg
305                 310                 315

<210> SEQ ID NO 63
<211> LENGTH: 972
<212> TYPE: DNA
<213> ORGANISM: Mus musculus

<400> SEQUENCE: 63
atggtcatgt cagtgcagaa tagcacagat ctgaccccag cttcctttgt tctgaatggg       60
atcccaggcc tggaagacat gcacatctgg atctccttcc ctttctgttc catgtatgca      120
gtggctatga tggggaactg tggactcctc tatctcatct tctttgagga ttccttacac      180
agacccatgt actacttttt agcaatgctt tctctaacag accttgtcat gtgctctagt      240
acaatcccca aaaccctgtg catcttctgg tttcatctca agaaattgg atttgatgac        300
tgtcttgtac agatgttctt catccatacc ttcacgggga tggagtctgg agtgctcatg      360
ctcatggctc tggaccgcta tgtagccatc tgctaccctc tgcgttactc caccattctc      420
accaatccta tcattgccaa gattgggtta gccaccttcc tgagggcgt tctgctaatt       480
attccattca catttctcac caagcgccta cctactgtc gaggcaatat aataaaccat        540
acctactgtg accacatgtc tgtagccaag ttgtcctgtg gcaatgtcaa ggtgaatgcc      600
atttatggtc tgatggttgc tctcttgatt gggggctttg acatcctgtg catcacaatc      660
tcctatacca tgattctgag ggcagtggtc agcttatcat cagcagatgc taggcagaag      720
gccttcagca cctgcactgc ccacatctgt gccattgttt tctcctatag cccagccttc      780
ttttccttct tttcccaccg ctttgggggg cacacaatac ctccatcttg ccacatcatt      840
gtggctaata tttatctgct tttgcctccc actatgaacc ctgttgtcta tggagtgaaa      900
accaaacaga tacgagactg tgtcataagg attctttcag ggtctaagga ttccaaagct      960
cacggtatat aa                                                          972

<210> SEQ ID NO 64
<211> LENGTH: 323
<212> TYPE: PRT
<213> ORGANISM: Mus musculus

<400> SEQUENCE: 64

Met Val Met Ser Val Gln Asn Ser Thr Asp Leu Thr Pro Ala Ser Phe

```
  1               5                  10                 15
Val Leu Asn Gly Ile Pro Gly Leu Glu Asp Met His Ile Trp Ile Ser
             20                 25                 30
Phe Pro Phe Cys Ser Met Tyr Ala Val Ala Met Met Gly Asn Cys Gly
             35                 40                 45
Leu Leu Tyr Leu Ile Phe Phe Glu Asp Ser Leu His Arg Pro Met Tyr
 50                 55                 60
Tyr Phe Leu Ala Met Leu Ser Leu Thr Asp Leu Val Met Cys Ser Ser
 65                 70                 75                 80
Thr Ile Pro Lys Thr Leu Cys Ile Phe Trp Phe His Leu Lys Glu Ile
             85                 90                 95
Gly Phe Asp Asp Cys Leu Val Gln Met Phe Phe Ile His Thr Phe Thr
             100                105                110
Gly Met Glu Ser Gly Val Leu Met Leu Met Ala Leu Asp Arg Tyr Val
             115                120                125
Ala Ile Cys Tyr Pro Leu Arg Tyr Ser Thr Ile Leu Thr Asn Pro Ile
             130                135                140
Ile Ala Lys Ile Gly Leu Ala Thr Phe Leu Arg Gly Val Leu Leu Ile
145                150                155                160
Ile Pro Phe Thr Phe Leu Thr Lys Arg Leu Pro Tyr Cys Arg Gly Asn
             165                170                175
Ile Ile Asn His Thr Tyr Cys Asp His Met Ser Val Ala Lys Leu Ser
             180                185                190
Cys Gly Asn Val Lys Val Asn Ala Ile Tyr Gly Leu Met Val Ala Leu
             195                200                205
Leu Ile Gly Gly Phe Asp Ile Leu Cys Ile Thr Ile Ser Tyr Thr Met
             210                215                220
Ile Leu Arg Ala Val Val Ser Leu Ser Ser Ala Asp Ala Arg Gln Lys
225                230                235                240
Ala Phe Ser Thr Cys Thr Ala His Ile Cys Ala Ile Val Phe Ser Tyr
             245                250                255
Ser Pro Ala Phe Phe Ser Phe Phe Ser His Arg Phe Gly His Gly His Thr
             260                265                270
Ile Pro Pro Ser Cys His Ile Ile Val Ala Asn Ile Tyr Leu Leu Leu
             275                280                285
Pro Pro Thr Met Asn Pro Val Val Tyr Gly Val Lys Thr Lys Gln Ile
             290                295                300
Arg Asp Cys Val Ile Arg Ile Leu Ser Gly Ser Lys Asp Ser Lys Ala
305                310                315                320
His Gly Ile
```

<210> SEQ ID NO 65
<211> LENGTH: 969
<212> TYPE: DNA
<213> ORGANISM: Mus musculus

<400> SEQUENCE: 65

| | | | | | |
|---|---|---|---|---|---|
| atgctcctgc | tgaatcaaac | agaggtgacc | ccagtctcat | ttattctgaa | tggaatccca | 60 |
| ggcctggaag | aaatgcacat | ctggatttcc | ttcccattct | gttctatgta | tgtaatagct | 120 |
| gtggtaggca | attgtggact | cctctacctc | atcttctttg | aagacagcct | tcacaggtca | 180 |
| atgtactact | tcttggctat | gctttccctt | acagaccttg | tcatgtgcag | tgcttcaata | 240 |
| cccaaaactc | tctgtatctt | ctggttctac | attaaggaaa | ttagctttac | tgattgtctg | 300 |

```
gtccagatgt tcttcatcca tactttcaca gcgatggagt ctggggtgct catgctcatg    360
gctctggacc gctatgtagc aatctgctac cctctgcact actccactat cctcaccaat    420
cctgtcattg caaaagctgg ccttgctaca ttcttgagag ctgtggtgct catcattcct    480
ttgattttca tcacaaagca tctgcccttc tgcagaagca atatattaat acaccatacc    540
tactgtgacc agttgtctgt agccaaggtc tcctgtggaa atatcaaggt caacattgtc    600
tatggtctga tgattgctct ctttattggg ggctttgata tcttgtgcat cacagtctcc    660
tacaccatga tcctgaaagc agtggtcagc ttatcttcag cagatgctag cagaaagct     720 ttcagcacct gcactgccca catctgtgcc attgttttct cctatagccc agccttcttt    780
tgtttctttt cccaccgctt tggggggcac atcatccctc atcttgcct catcattgtg     840 gctaaccttt atctgctttt gcctcccact atgaaccctg tggtctatgg agtgaaaacc    900
aagcagatac gagactgtgt cataaggatc ttttcaggtt ctaaggacat caaatcccac    960
agcatatga                                                            969

<210> SEQ ID NO 66
<211> LENGTH: 322
<212> TYPE: PRT
<213> ORGANISM: Mus musculus

<400> SEQUENCE: 66

Met Leu Leu Leu Asn Gln Thr Glu Val Thr Pro Val Ser Phe Ile Leu
1               5                   10                  15

Asn Gly Ile Pro Gly Leu Glu Glu Met His Ile Trp Ile Ser Phe Pro
            20                  25                  30

Phe Cys Ser Met Tyr Val Ile Ala Val Val Gly Asn Cys Gly Leu Leu
        35                  40                  45

Tyr Leu Ile Phe Phe Glu Asp Ser Leu His Arg Ser Met Tyr Tyr Phe
    50                  55                  60

Leu Ala Met Leu Ser Leu Thr Asp Leu Val Met Cys Ser Ala Ser Ile
65                  70                  75                  80

Pro Lys Thr Leu Cys Ile Phe Trp Phe Tyr Ile Lys Glu Ile Ser Phe
                85                  90                  95

Thr Asp Cys Leu Val Gln Met Phe Phe Ile His Thr Phe Thr Ala Met
            100                 105                 110

Glu Ser Gly Val Leu Met Leu Met Ala Leu Asp Arg Tyr Val Ala Ile
        115                 120                 125

Cys Tyr Pro Leu His Tyr Ser Thr Ile Leu Thr Asn Pro Val Ile Ala
    130                 135                 140

Lys Ala Gly Leu Ala Thr Phe Leu Arg Ala Val Val Leu Ile Ile Pro
145                 150                 155                 160

Leu Ile Phe Ile Thr Lys His Leu Pro Phe Cys Arg Ser Asn Ile Leu
                165                 170                 175

Ile His His Thr Tyr Cys Asp Gln Leu Ser Val Ala Lys Val Ser Cys
            180                 185                 190

Gly Asn Ile Lys Val Asn Ile Val Tyr Gly Leu Met Ile Ala Leu Phe
        195                 200                 205

Ile Gly Gly Phe Asp Ile Leu Cys Ile Thr Val Ser Tyr Thr Met Ile
    210                 215                 220

Leu Lys Ala Val Val Ser Leu Ser Ser Ala Asp Ala Arg Gln Lys Ala
225                 230                 235                 240

Phe Ser Thr Cys Thr Ala His Ile Cys Ala Ile Val Phe Ser Tyr Ser
                245                 250                 255
```

```
Pro Ala Phe Phe Cys Phe Phe Ser His Arg Phe Gly Gly His Ile Ile
            260                 265                 270

Pro Pro Ser Cys Leu Ile Ile Val Ala Asn Leu Tyr Leu Leu Pro
        275                 280                 285

Pro Thr Met Asn Pro Val Val Tyr Gly Val Lys Thr Lys Gln Ile Arg
        290                 295                 300

Asp Cys Val Ile Arg Ile Phe Ser Gly Ser Lys Asp Ile Lys Ser His
305                 310                 315                 320

Ser Ile

<210> SEQ ID NO 67
<211> LENGTH: 972
<212> TYPE: DNA
<213> ORGANISM: Mus musculus

<400> SEQUENCE: 67
atggtcatgt cagcgaggaa taacccagat ctgaccccag cttcctttgt tctgaatggg      60
atcccaggcc tggaacacat gcacatctgg atctccttcc ctttctgttc catgtatgca     120
gtggctatga tggggaactg tggactcctc tatctcatct tctttgagga ttccttacac     180
agacccatgt actactttt agcaatgctt tctctaacag accttgtcat gtgctctagt     240
acaatcccca agccctgtg catcttctgg tttcatctca agaaattgg atttgacgac      300
tgtcttgtac agatgttctt catccatacc ttcatgggga tggagtctgg agtgctcatg     360
ctcatggctc tggaccacta tgtagccatt tgctaccctc tgcattactc caccattctc     420
accaatccta tcattgccaa gattgggtta gccaccttcc tgagggggcgt tctgctaatt     480
attccattca tatttctctc caagtgccta ccctactttc gaggcaatat aataaaccat     540
acctactgtg accacatgtc tgtagccaag ttgccctgtg gcaatgtcaa ggtgaatgcc     600
atttatggtc taatggttgc tctcttgatt gggggttttg acatcctgtg tatcacaatc     660
tcctatatca tgattctgag ggcagtggtc agcttatcat cagcagatgc taggcagaag     720
gccttcagca cctgcactgc ccacatctgt gccattgttt ctcctatag cccaaccttc     780
ttgtccttct tttcccacca ctttggggg cacacaatcc ctccatcttg ccacatcatt     840
gtggctaata tttatctgct tttgcctccc actatgaacc ctgttgtcta tggagtgaaa     900
accaaacaga tacaagactg tgtcataagg attttttcag agtctaagga ttccaaagct     960
cacggtatat aa                                                        972

<210> SEQ ID NO 68
<211> LENGTH: 323
<212> TYPE: PRT
<213> ORGANISM: Mus musculus

<400> SEQUENCE: 68

Met Val Met Ser Ala Arg Asn Asn Pro Asp Leu Thr Pro Ala Ser Phe
1               5                   10                  15

Val Leu Asn Gly Ile Pro Gly Leu Glu His Met His Ile Trp Ile Ser
            20                  25                  30

Phe Pro Phe Cys Ser Met Tyr Ala Val Ala Met Met Gly Asn Cys Gly
        35                  40                  45

Leu Leu Tyr Leu Ile Phe Phe Glu Asp Ser Leu His Arg Pro Met Tyr
    50                  55                  60

Tyr Phe Leu Ala Met Leu Ser Leu Thr Asp Leu Val Met Cys Ser Ser
65                  70                  75                  80
```

```
Thr Ile Pro Lys Ala Leu Cys Ile Phe Trp Phe His Leu Lys Glu Ile
                85                  90                  95
Gly Phe Asp Asp Cys Leu Val Gln Met Phe Ile His Thr Phe Met
            100                 105                 110
Gly Met Glu Ser Gly Val Leu Met Leu Met Ala Leu Asp His Tyr Val
        115                 120                 125
Ala Ile Cys Tyr Pro Leu His Tyr Ser Thr Ile Leu Thr Asn Pro Ile
    130                 135                 140
Ile Ala Lys Ile Gly Leu Ala Thr Phe Leu Arg Gly Val Leu Leu Ile
145                 150                 155                 160
Ile Pro Phe Ile Phe Leu Ser Lys Cys Leu Pro Tyr Phe Arg Gly Asn
                165                 170                 175
Ile Ile Asn His Thr Tyr Cys Asp His Met Ser Val Ala Lys Leu Pro
            180                 185                 190
Cys Gly Asn Val Lys Val Asn Ala Ile Tyr Gly Leu Met Val Ala Leu
        195                 200                 205
Leu Ile Gly Gly Phe Asp Ile Leu Cys Ile Thr Ile Ser Tyr Ile Met
    210                 215                 220
Ile Leu Arg Ala Val Ser Leu Ser Ser Ala Asp Ala Arg Gln Lys
225                 230                 235                 240
Ala Phe Ser Thr Cys Thr Ala His Ile Cys Ala Ile Val Phe Ser Tyr
                245                 250                 255
Ser Pro Thr Phe Leu Ser Phe Phe Ser His His Phe Gly His Thr
            260                 265                 270
Ile Pro Pro Ser Cys His Ile Ile Val Ala Asn Ile Tyr Leu Leu Leu
        275                 280                 285
Pro Pro Thr Met Asn Pro Val Val Tyr Gly Val Lys Thr Lys Gln Ile
    290                 295                 300
Gln Asp Cys Val Ile Arg Ile Phe Ser Glu Ser Lys Asp Ser Lys Ala
305                 310                 315                 320
His Gly Ile

<210> SEQ ID NO 69
<211> LENGTH: 963
<212> TYPE: DNA
<213> ORGANISM: Homo sapiens

<400> SEQUENCE: 69
atgtcatttc taaatggcac cagcctaact ccagcttcat tcatcctaaa tggcatccct      60
ggtttggaag atgtgcattt gtggatctcc ttcccactgt gtaccatgta cagcattgct     120
attacaggga acttcggcct tatgtacctc atctactgtg atgaggcctt acacagacct     180
atgtatgtct tccttgccct tctttccttc acagatgtgc tcatgtgcac cagcacccct     240
cccaacactc tcttcatatt gtggtttaat ctcaaggaga ttgattttaa agcctgcctc     300
gcccagatgt tctttgtgca caccttcaca gggatggagt ctggggtgct catgctcatg     360
gccctggacc actgtgtggc catctgcttc cctctgcgtt atgccaccat cctcactaat     420
tcagtcattg ctaaagctgg gttcctcact tttcttaggg gtgtgatgct tgttatccct     480
tccactttcc tcaccaagcg ccttccatac tgcaagggca acgtcatacc ccacacctac     540
tgtgaccaca tgtctgtggc caagatatct tgtggtaatg tcaggttaa cgccatctat     600 ggtttgatag ttgccctgct gattgggggc tttgatatcc tgtgcattac aatctcctac     660
actatgattc ttcaagcagt tgtgagtcta tcatcagcag atgctcgaca gaaggccttc     720
```

```
agcacctgca ctgcccactt ctgtgccata gtcctcacct atgttccagc cttctttacc    780
ttctttacac accatttggg gggacacacc attcctctac acatacatat tattatggct    840
aatctctacc tactaatgcc tcccacaatg aaccctattg tgtatggggt gaaaaccagg    900
caggtacgag aaagtgtcat taggttcttt cttaagggaa aggacaattc tcataacttt    960
taa                                                                 963
```

<210> SEQ ID NO 70
<211> LENGTH: 320
<212> TYPE: PRT
<213> ORGANISM: Homo sapiens

<400> SEQUENCE: 70

```
Met Ser Phe Leu Asn Gly Thr Ser Leu Thr Pro Ala Ser Phe Ile Leu
1               5                   10                  15

Asn Gly Ile Pro Gly Leu Glu Asp Val His Leu Trp Ile Ser Phe Pro
            20                  25                  30

Leu Cys Thr Met Tyr Ser Ile Ala Ile Thr Gly Asn Phe Gly Leu Met
        35                  40                  45

Tyr Leu Ile Tyr Cys Asp Glu Ala Leu His Arg Pro Met Tyr Val Phe
    50                  55                  60

Leu Ala Leu Leu Ser Phe Thr Asp Val Leu Met Cys Thr Ser Thr Leu
65                  70                  75                  80

Pro Asn Thr Leu Phe Ile Leu Trp Phe Asn Leu Lys Glu Ile Asp Phe
                85                  90                  95

Lys Ala Cys Leu Ala Gln Met Phe Phe Val His Thr Phe Thr Gly Met
            100                 105                 110

Glu Ser Gly Val Leu Met Leu Met Ala Leu Asp His Cys Val Ala Ile
        115                 120                 125

Cys Phe Pro Leu Arg Tyr Ala Thr Ile Leu Thr Asn Ser Val Ile Ala
    130                 135                 140

Lys Ala Gly Phe Leu Thr Phe Leu Arg Gly Val Met Leu Val Ile Pro
145                 150                 155                 160

Ser Thr Phe Leu Thr Lys Arg Leu Pro Tyr Cys Lys Gly Asn Val Ile
                165                 170                 175

Pro His Thr Tyr Cys Asp His Met Ser Val Ala Lys Ile Ser Cys Gly
            180                 185                 190

Asn Val Arg Val Asn Ala Ile Tyr Gly Leu Ile Val Ala Leu Leu Ile
        195                 200                 205

Gly Gly Phe Asp Ile Leu Cys Ile Thr Ile Ser Tyr Thr Met Ile Leu
    210                 215                 220

Gln Ala Val Val Ser Leu Ser Ser Ala Asp Ala Arg Gln Lys Ala Phe
225                 230                 235                 240

Ser Thr Cys Thr Ala His Phe Cys Ala Ile Val Leu Thr Tyr Val Pro
                245                 250                 255

Ala Phe Phe Thr Phe Thr His His Phe Gly Gly His Thr Ile Pro
            260                 265                 270

Leu His Ile His Ile Met Ala Asn Leu Tyr Leu Leu Met Pro Pro
        275                 280                 285

Thr Met Asn Pro Ile Val Tyr Gly Val Lys Thr Arg Gln Val Arg Glu
    290                 295                 300

Ser Val Ile Arg Phe Phe Leu Lys Gly Lys Asp Asn Ser His Asn Phe
305                 310                 315                 320
```

<210> SEQ ID NO 71
<211> LENGTH: 966
<212> TYPE: DNA
<213> ORGANISM: Homo Sapiens

<400> SEQUENCE: 71

```
atgctaacac tgaataaaac agacctaata ccagcttcat ttattctgaa tggagtccca      60
ggactggaag acacacaact ctggatttcc ttcccattct gctctatgta tgttgtggct     120
atggtaggga attgtggact cctctacctc attcactatg aggatgccct gcacaaaccc     180
atgtactact tcttggccat gctttccttt actgacttg ttatgtgctc tagtacaatc      240
cctaaagccc tctgcatctt ctggtttcat ctcaaggaca ttggatttga tgaatgcctt     300
gtccagatgt tcttcaccca caccttcaca gggatggagt ctggggtgct tatgcttatg     360
gccctggatc gctatgtggc catctgctac cccttacgct attcaactat cctcaccaat     420
cctgtaattg caaaggttgg gactgccacc ttcctgagag gggtattact cattattccc     480
tttactttcc tcaccaagct cctgcccta tgcagaggca atatacttcc ccatacctac     540
tgtgaccaca tgtctgtagc caaattgtcc tgtggtaatg tcaaggtcaa tgccatctat     600
ggtctgatgg ttgccctcct gatttggggc tttgacatac tgtgtatcac caactcctat     660
accatgattc tccgggcagt ggtcagcctc cctcagcag atgctcggca gaaggccttt      720
aatacctgca ctgcccacat tgtgccatt gtttctcct atactccagc tttcttctcc       780
ttcttttccc accgctttgg ggaacacata atccccct cttgccacat cattgtagcc       840
aatatttatc tgctcctacc acccactatg aaccctattg tctatggggt gaaaaccaaa     900
cagatacgag actgtgtcat aaggatcctt tcaggttcta aggataccaa atcctacagc     960
atgtga                                                               966
```

<210> SEQ ID NO 72
<211> LENGTH: 321
<212> TYPE: PRT
<213> ORGANISM: Homo sapiens

<400> SEQUENCE: 72

```
Met Leu Thr Leu Asn Lys Thr Asp Leu Ile Pro Ala Ser Phe Ile Leu
1               5                   10                  15

Asn Gly Val Pro Gly Leu Glu Asp Thr Gln Leu Trp Ile Ser Phe Pro
            20                  25                  30

Phe Cys Ser Met Tyr Val Val Ala Met Val Gly Asn Cys Gly Leu Leu
        35                  40                  45

Tyr Leu Ile His Tyr Glu Asp Ala Leu His Lys Pro Met Tyr Tyr Phe
    50                  55                  60

Leu Ala Met Leu Ser Phe Thr Asp Leu Val Met Cys Ser Ser Thr Ile
65                  70                  75                  80

Pro Lys Ala Leu Cys Ile Phe Trp Phe His Leu Lys Asp Ile Gly Phe
                85                  90                  95

Asp Glu Cys Leu Val Gln Met Phe Phe Thr His Thr Phe Thr Gly Met
            100                 105                 110

Glu Ser Gly Val Leu Met Leu Met Ala Leu Asp Arg Tyr Val Ala Ile
        115                 120                 125

Cys Tyr Pro Leu Arg Tyr Ser Thr Ile Leu Thr Asn Pro Val Ile Ala
    130                 135                 140

Lys Val Gly Thr Ala Thr Phe Leu Arg Gly Val Leu Leu Ile Ile Pro
145                 150                 155                 160
```

```
Phe Thr Phe Leu Thr Lys Leu Leu Pro Tyr Cys Arg Gly Asn Ile Leu
                165                 170                 175

Pro His Thr Tyr Cys Asp His Met Ser Val Ala Lys Leu Ser Cys Gly
            180                 185                 190

Asn Val Lys Val Asn Ala Ile Tyr Gly Leu Met Val Ala Leu Leu Ile
        195                 200                 205

Trp Gly Phe Asp Ile Leu Cys Ile Thr Asn Ser Tyr Thr Met Ile Leu
    210                 215                 220

Arg Ala Val Val Ser Leu Ser Ser Ala Asp Ala Arg Gln Lys Ala Phe
225                 230                 235                 240

Asn Thr Cys Thr Ala His Ile Cys Ala Ile Val Phe Ser Tyr Thr Pro
                245                 250                 255

Ala Phe Phe Ser Phe Phe Ser His Arg Phe Gly Glu His Ile Ile Pro
            260                 265                 270

Pro Ser Cys His Ile Ile Val Ala Asn Ile Tyr Leu Leu Leu Pro Pro
        275                 280                 285

Thr Met Asn Pro Ile Val Tyr Gly Val Lys Thr Lys Gln Ile Arg Asp
    290                 295                 300

Cys Val Ile Arg Ile Leu Ser Gly Ser Lys Asp Thr Lys Ser Tyr Ser
305                 310                 315                 320

Met

<210> SEQ ID NO 73
<211> LENGTH: 975
<212> TYPE: DNA
<213> ORGANISM: Homo Sapiens

<400> SEQUENCE: 73
atgcctctat ttaattcatt atgctggttt ccaacaattc atgtgactcc tccatctttt      60
attcttaatg gaatacctgg tctggaaaga gtacatgtat ggatctccct cccactctgc     120
acaatgtaca tcatcttcct tgtggggaat cttggtcttg tgtacctcat ttattatgag     180
gagtccttac atcatccgat gtattttttt tttggccatg ctctctccct cattgacctc     240
cttacctgca ccaccactct acccaatgca ctctgcatct tctggttcag tctcaaagaa     300
attaacttca atgcttgctt ggcccagatg ttctttgttc atgggttcac aggtgtggag     360
tctggggtgc tcatgctcat ggctctagac cgctatgtag ccatttgcta cccttttgcgt     420 tatgctacca cactcaccaa ccctatcatt gccaaggctg agcttgccac cttcctgagg     480
ggtgtattgc tgatgattcc tttcccattc ttggttaagc gtttgccttt ctgccaaagc     540
aatattatct cccatacgta ctgcgaccac atgtctgtag taaagctatc ttgtgccagc     600
atcaaggtca atgtaatcta tggtctaatg gttgctctcc tgattggagt gtttgacatt     660
tgttgtatat ctttgtctta cactttgatc ctcaaggcag cgatcagcct ctcttcatca     720
gatgctcggc agaaggcttt cagcacctgc actgccccata tatctgccat catcatcacc     780
tatgttccag cattcttcac tttctttgcc accgttttg ggggacacac aattccccct     840
tctcttcaca tcattgtggc taatctttat cttcttcttc ccccaactct aaaccctatt     900
gtttatggag taaagacaaa acagatacgc aagagtgtca taagttcttt ccagggtgat     960
aagggtgcag gttga                                                     975

<210> SEQ ID NO 74
<211> LENGTH: 324
<212> TYPE: PRT
```

<213> ORGANISM: Homo sapiens

<400> SEQUENCE: 74

| | | | | | | | | | | | | | | |
|---|---|---|---|---|---|---|---|---|---|---|---|---|---|---|
| Met | Pro | Leu | Phe | Asn | Ser | Leu | Cys | Trp | Phe | Pro | Thr | Ile | His | Val | Thr |
| 1 | | | | 5 | | | | | 10 | | | | | 15 | |

| Pro | Pro | Ser | Phe | Ile | Leu | Asn | Gly | Ile | Pro | Gly | Leu | Glu | Arg | Val | His |
| 20 | | | | | 25 | | | | | 30 | | | | | |

| Val | Trp | Ile | Ser | Leu | Pro | Leu | Cys | Thr | Met | Tyr | Ile | Ile | Phe | Leu | Val |
| | | 35 | | | | | 40 | | | | | 45 | | | |

| Gly | Asn | Leu | Gly | Leu | Val | Tyr | Leu | Ile | Tyr | Tyr | Glu | Glu | Ser | Leu | His |
| | 50 | | | | | 55 | | | | | 60 | | | | |

| His | Pro | Met | Tyr | Phe | Phe | Gly | His | Ala | Leu | Ser | Leu | Ile | Asp | Leu |
| 65 | | | | | 70 | | | | 75 | | | | | 80 |

| Leu | Thr | Cys | Thr | Thr | Thr | Leu | Pro | Asn | Ala | Leu | Cys | Ile | Phe | Trp | Phe |
| | | | | 85 | | | | | 90 | | | | | 95 | |

| Ser | Leu | Lys | Glu | Ile | Asn | Phe | Asn | Ala | Cys | Leu | Ala | Gln | Met | Phe | Phe |
| | | | 100 | | | | | 105 | | | | | 110 | | |

| Val | His | Gly | Phe | Thr | Gly | Val | Glu | Ser | Gly | Val | Leu | Met | Leu | Met | Ala |
| | | 115 | | | | | 120 | | | | | 125 | | | |

| Leu | Asp | Arg | Tyr | Val | Ala | Ile | Cys | Tyr | Pro | Leu | Arg | Tyr | Ala | Thr | Thr |
| | 130 | | | | | 135 | | | | | 140 | | | | |

| Leu | Thr | Asn | Pro | Ile | Ile | Ala | Lys | Ala | Glu | Leu | Ala | Thr | Phe | Leu | Arg |
| 145 | | | | | 150 | | | | | 155 | | | | | 160 |

| Gly | Val | Leu | Leu | Met | Ile | Pro | Phe | Pro | Phe | Leu | Val | Lys | Arg | Leu | Pro |
| | | | | 165 | | | | | 170 | | | | | 175 | |

| Phe | Cys | Gln | Ser | Asn | Ile | Ile | Ser | His | Thr | Tyr | Cys | Asp | His | Met | Ser |
| | | | 180 | | | | | 185 | | | | | 190 | | |

| Val | Val | Lys | Leu | Ser | Cys | Ala | Ser | Ile | Lys | Val | Asn | Val | Ile | Tyr | Gly |
| | | 195 | | | | | 200 | | | | | 205 | | | |

| Leu | Met | Val | Ala | Leu | Leu | Ile | Gly | Val | Phe | Asp | Ile | Cys | Cys | Ile | Ser |
| | 210 | | | | | 215 | | | | | 220 | | | | |

| Leu | Ser | Tyr | Thr | Leu | Ile | Leu | Lys | Ala | Ala | Ile | Ser | Leu | Ser | Ser | Ser |
| 225 | | | | | 230 | | | | | 235 | | | | | 240 |

| Asp | Ala | Arg | Gln | Lys | Ala | Phe | Ser | Thr | Cys | Thr | Ala | His | Ile | Ser | Ala |
| | | | 245 | | | | | 250 | | | | | 255 | | |

| Ile | Ile | Ile | Thr | Tyr | Val | Pro | Ala | Phe | Phe | Thr | Phe | Phe | Ala | His | Arg |
| | | | 260 | | | | | 265 | | | | | 270 | | |

| Phe | Gly | Gly | His | Thr | Ile | Pro | Pro | Ser | Leu | His | Ile | Ile | Val | Ala | Asn |
| | | 275 | | | | | 280 | | | | | 285 | | | |

| Leu | Tyr | Leu | Leu | Leu | Pro | Pro | Thr | Leu | Asn | Pro | Ile | Val | Tyr | Gly | Val |
| | 290 | | | | | 295 | | | | | 300 | | | | |

| Lys | Thr | Lys | Gln | Ile | Arg | Lys | Ser | Val | Ile | Lys | Phe | Phe | Gln | Gly | Asp |
| 305 | | | | | 310 | | | | | 315 | | | | | 320 |

| Lys | Gly | Ala | Gly |
|---|---|---|---|

<210> SEQ ID NO 75
<211> LENGTH: 930
<212> TYPE: DNA
<213> ORGANISM: Homo sapiens

<400> SEQUENCE: 75

```
atggatatat cagagggaaa taagactctt gtgacagagt ttgttctcac aggacttaca      60
gatcgaccat ggctgcacgt cctcttcttt gttgtgtttt tggtggtcta tctcatcacc     120
atggtgggca accttggact gatagttcta atttggaacg accccatctt catatgccc      180
```

```
atgtacttat tccttggtgg tttagccttt tcagatgctt gtacttcaac ctctataacc    240
cctaggatgc tggtcaattt cttagacaag actgcaatga tatccctagc tgagtgcatc    300
acccagtttt acttttttgc ttccagtgca actacagaat gcttcctcct ggtgatgatg    360
gcctatgacc gctatgtagc catatgtaat cccttgcttt atccagtgat gatgtccaac    420
aaactcagcg ctcagttgct aagtatttca tatgtaattg gtttcctgca tcctctggtt    480
catgtgagtt tactattgcg actaactttc tgcaggttta acataataca ttatttctac    540
tgtgaaattt tacaactgtt caaaatttca tgcaatggtc catctattaa cgcactaatg    600
atatttattt ttggtgcttt tatacaaata cccactttaa tgactatcat aatctcttat    660
actcgtgtgc tctttgatat tctgaaaaaa aagtctgaaa agggcagaag caaagccttc    720
tccacatgcg gcgcccatct gctttctgtc tcattgtact acggaactct gatcttcatg    780
tatgtgcgtc ctgcatctgg cttagctgaa gaccaagaca aagtgtattc tctgttttac    840
acgattataa ttcccctgct aaacccattt atttacagct tgagaaataa aaaagtcatg    900
catgcattga agagagttat aaggaagtaa                                     930
```

<210> SEQ ID NO 76
<211> LENGTH: 309
<212> TYPE: PRT
<213> ORGANISM: Homo sapiens

<400> SEQUENCE: 76

```
Met Asp Ile Ser Glu Gly Asn Lys Thr Leu Val Thr Glu Phe Val Leu
1               5                   10                  15

Thr Gly Leu Thr Asp Arg Pro Trp Leu His Val Leu Phe Phe Val Val
                20                  25                  30

Phe Leu Val Val Tyr Leu Ile Thr Met Val Gly Asn Leu Gly Leu Ile
            35                  40                  45

Val Leu Ile Trp Asn Asp Pro His Leu His Met Pro Met Tyr Leu Phe
        50                  55                  60

Leu Gly Gly Leu Ala Phe Ser Asp Ala Cys Thr Ser Thr Ser Ile Thr
65                  70                  75                  80

Pro Arg Met Leu Val Asn Phe Leu Asp Lys Thr Ala Met Ile Ser Leu
                85                  90                  95

Ala Glu Cys Ile Thr Gln Phe Tyr Phe Phe Ala Ser Ser Ala Thr Thr
            100                 105                 110

Glu Cys Phe Leu Leu Val Met Met Ala Tyr Asp Arg Tyr Val Ala Ile
        115                 120                 125

Cys Asn Pro Leu Leu Tyr Pro Val Met Met Ser Asn Lys Leu Ser Ala
    130                 135                 140

Gln Leu Leu Ser Ile Ser Tyr Val Ile Gly Phe Leu His Pro Leu Val
145                 150                 155                 160

His Val Ser Leu Leu Arg Leu Thr Phe Cys Arg Phe Asn Ile Ile
                165                 170                 175

His Tyr Phe Tyr Cys Glu Ile Leu Gln Leu Phe Lys Ile Ser Cys Asn
            180                 185                 190

Gly Pro Ser Ile Asn Ala Leu Met Ile Phe Ile Phe Gly Ala Phe Ile
        195                 200                 205

Gln Ile Pro Thr Leu Met Thr Ile Ile Ser Tyr Thr Arg Val Leu
    210                 215                 220

Phe Asp Ile Leu Lys Lys Lys Ser Glu Lys Gly Arg Ser Lys Ala Phe
225                 230                 235                 240
```

```
Ser Thr Cys Gly Ala His Leu Leu Ser Val Ser Leu Tyr Tyr Gly Thr
                245                 250                 255

Leu Ile Phe Met Tyr Val Arg Pro Ala Ser Gly Leu Ala Glu Asp Gln
            260                 265                 270

Asp Lys Val Tyr Ser Leu Phe Tyr Thr Ile Ile Pro Leu Leu Asn
        275                 280                 285

Pro Phe Ile Tyr Ser Leu Arg Asn Lys Lys Val Met His Ala Leu Arg
    290                 295                 300

Arg Val Ile Arg Lys
305
```

<210> SEQ ID NO 77
<211> LENGTH: 918
<212> TYPE: DNA
<213> ORGANISM: Mus Musculus

<400> SEQUENCE: 77

```
atggaactga acaggaccca gctgactgaa tttgttctca gaggaataac agatcgttca      60
gagctgcaag tccccctgtt cctggtgttc tttctcatct atgttatcac catggtgggc     120
aaccttggct taatctttgt catctggaag accctcatc ttcacacacc catgtacctt     180
ttccttggaa atttggcctt tgctgatgcc tgtaattcat cctctgtgac accaaagatg     240
cttatgaaat tttaaataa gaatgacatg atatccatgg gtgagtgttt tgctcaattt     300
tatttctttt gttcaagtgt aactgcagaa gccttcattc tggtagctat ggcctatgac     360
cgctatgtag ccatatgcaa acctctgctc tatgtagtgg tgatgtccaa cagactctgt     420
attcagttca taggtgtatc ctatctaatt ggacttctac atggcttact tcatgtagga     480
ttgttattta ggttaacgtt ttgtagttcc aatgtaatag attatttcta ctgtgacatc     540
ctgccacttt ataggatttc ttgcactgac ccatcgatca atgtactggt agctttcatt     600
atgggtattt tattacaagt gagtaccttt atgagtatta tagtctccta tgtccgtgtc     660
ctctttgcca tcctgagaac aaagtctgag aggggcagaa acaaagcctt ctctacttgc     720
agttcccacc tgtcatctgt gtctttgttc tatggcactc tcttcatcat atatgtcctc     780
tctggctctg acacagataa ttatcagggt aaaatgtatt cactgttcta taccattatc     840
attcctctgc taaacccctt catttacagc ctaagaaata agaagtcat cggtgccttg     900
agaaaagtca gaaatga                                                    918
```

<210> SEQ ID NO 78
<211> LENGTH: 305
<212> TYPE: PRT
<213> ORGANISM: Mus musculus

<400> SEQUENCE: 78

```
Met Glu Leu Asn Arg Thr Gln Leu Thr Glu Phe Val Leu Arg Gly Ile
1               5                   10                  15

Thr Asp Arg Ser Glu Leu Gln Val Pro Leu Phe Leu Val Phe Phe Leu
            20                  25                  30

Ile Tyr Val Ile Thr Met Val Gly Asn Leu Gly Leu Ile Phe Val Ile
        35                  40                  45

Trp Lys Asp Pro His Leu His Thr Pro Met Tyr Leu Phe Leu Gly Asn
    50                  55                  60

Leu Ala Phe Ala Asp Ala Cys Asn Ser Ser Ser Val Thr Pro Lys Met
65                  70                  75                  80
```

```
Leu Met Lys Phe Leu Asn Lys Asn Asp Met Ile Ser Met Gly Glu Cys
            85                  90                  95

Phe Ala Gln Phe Tyr Phe Phe Cys Ser Ser Val Thr Ala Glu Ala Phe
        100                 105                 110

Ile Leu Val Ala Met Ala Tyr Asp Arg Tyr Val Ala Ile Cys Lys Pro
        115                 120                 125

Leu Leu Tyr Val Val Met Ser Asn Arg Leu Cys Ile Gln Phe Ile
        130                 135                 140

Gly Val Ser Tyr Leu Ile Gly Leu Leu His Gly Leu Leu His Val Gly
145                 150                 155                 160

Leu Leu Phe Arg Leu Thr Phe Cys Ser Ser Asn Val Ile Asp Tyr Phe
                165                 170                 175

Tyr Cys Asp Ile Leu Pro Leu Tyr Arg Ile Ser Cys Thr Asp Pro Ser
                180                 185                 190

Ile Asn Val Leu Val Ala Phe Ile Met Gly Ile Leu Leu Gln Val Ser
            195                 200                 205

Thr Phe Met Ser Ile Ile Val Ser Tyr Val Arg Val Leu Phe Ala Ile
        210                 215                 220

Leu Arg Thr Lys Ser Glu Arg Gly Arg Asn Lys Ala Phe Ser Thr Cys
225                 230                 235                 240

Ser Ser His Leu Ser Ser Val Ser Leu Phe Tyr Gly Thr Leu Phe Ile
                245                 250                 255

Ile Tyr Val Leu Ser Gly Ser Asp Thr Asp Asn Tyr Gln Gly Lys Met
                260                 265                 270

Tyr Ser Leu Phe Tyr Thr Ile Ile Ile Pro Leu Leu Asn Pro Phe Ile
            275                 280                 285

Tyr Ser Leu Arg Asn Lys Glu Val Ile Gly Ala Leu Arg Lys Val Arg
        290                 295                 300

Lys
305

<210> SEQ ID NO 79
<211> LENGTH: 1113
<212> TYPE: DNA
<213> ORGANISM: Homo sapiens

<400> SEQUENCE: 79
atgttctcaa tgacaacaga agcactcaat aattttgcac ttggatgtac caacttgtta      60
atgactatga taccacaaat tgatctgaag caaattttcc tttgtcctaa ttgcagacta     120
tacatgatcc ctgttggagc tttcatcttt tccttgggaa acatgcaaaa ccaaagcttt     180
gtaactgagt ttgtcctcct gggactttca cagaatccaa atgttcagga atagtatt      240 gttgtatttt tgtttgtcta cattgcaact gttgggggca acatgctaat tgtagtaacc     300
attctcagca gccctgctct tctggtgtct cctatgtact tcttcttggg cttcctgtcc     360
ttcctggatg cgtgcttctc atctgtcatc acccccaaga tgattgtaga ctccctctat     420
gtgacaaaaa ccatctcttt tgaaggctgc atgatgcagc tctttgctga acacttcttt     480
gctggggtgg aggtgattgt cctcacagcc atggcctatg atcgttatgt ggccatttgc     540
aagcccttgc attactcttc tatcatgaac aggaggctct gtggcattct gatggggta    600 gcctggacag ggggcctctt gcattccatg atacaaattc ttttttactt ccagcttccc     660
ttttgtggcc ccaatgtcat caatcacttt atgtgtgact tgtacccgtt actggagctt     720
gcctgcactg atactcacat ctttggcctc atggtggtca tcaacagtgg gtttatctgc     780
```

-continued

```
atcataaact tctccttgtt gcttgtctcc tatgctgtca tcttgctctc tctgagaaca    840
cacagttctg aagggcgctg gaaagctctc tccacctgtg gatctcacat tgctgttgtg    900
attttgttct ttgtcccatg catatttgta tatacacgac ctccatctgc ttttccctt    960 gacaaaatgg cggcaatatt ttatatcatc ttaaatccct tgctcaatcc tttgatttac   1020
actttcagga ataaggaagt aaaacaggcc atgaggagaa tatggaacag actgatggtg   1080
gtttctgatg agaagaaaa tattaaactt taa                                 1113
```

<210> SEQ ID NO 80
<211> LENGTH: 370
<212> TYPE: PRT
<213> ORGANISM: Homo sapiens

<400> SEQUENCE: 80

```
Met Phe Ser Met Thr Thr Glu Ala Leu Asn Asn Phe Ala Leu Gly Cys
1               5                   10                  15

Thr Asn Leu Leu Met Thr Met Ile Pro Gln Ile Asp Leu Lys Gln Ile
            20                  25                  30

Phe Leu Cys Pro Asn Cys Arg Leu Tyr Met Ile Pro Val Gly Ala Phe
        35                  40                  45

Ile Phe Ser Leu Gly Asn Met Gln Asn Gln Ser Phe Val Thr Glu Phe
    50                  55                  60

Val Leu Gly Leu Ser Gln Asn Pro Asn Val Gln Glu Ile Val Phe
65                  70                  75                  80

Val Val Phe Leu Phe Val Tyr Ile Ala Thr Val Gly Gly Asn Met Leu
                85                  90                  95

Ile Val Val Thr Ile Leu Ser Ser Pro Ala Leu Leu Val Ser Pro Met
            100                 105                 110

Tyr Phe Phe Leu Gly Phe Leu Ser Phe Leu Asp Ala Cys Phe Ser Ser
        115                 120                 125

Val Ile Thr Pro Lys Met Ile Val Asp Ser Leu Tyr Val Thr Lys Thr
    130                 135                 140

Ile Ser Phe Glu Gly Cys Met Met Gln Leu Phe Ala Glu His Phe Phe
145                 150                 155                 160

Ala Gly Val Glu Val Ile Val Leu Thr Ala Met Ala Tyr Asp Arg Tyr
                165                 170                 175

Val Ala Ile Cys Lys Pro Leu His Tyr Ser Ser Ile Met Asn Arg Arg
            180                 185                 190

Leu Cys Gly Ile Leu Met Gly Val Ala Trp Thr Gly Gly Leu Leu His
        195                 200                 205

Ser Met Ile Gln Ile Leu Phe Thr Phe Gln Leu Pro Phe Cys Gly Pro
    210                 215                 220

Asn Val Ile Asn His Phe Met Cys Asp Leu Tyr Pro Leu Leu Glu Leu
225                 230                 235                 240

Ala Cys Thr Asp Thr His Ile Phe Gly Leu Met Val Val Ile Asn Ser
                245                 250                 255

Gly Phe Ile Cys Ile Ile Asn Phe Ser Leu Leu Val Ser Tyr Ala
            260                 265                 270

Val Ile Leu Leu Ser Leu Arg Thr His Ser Ser Glu Gly Arg Trp Lys
        275                 280                 285

Ala Leu Ser Thr Cys Gly Ser His Ile Ala Val Val Ile Leu Phe Phe
    290                 295                 300

Val Pro Cys Ile Phe Val Tyr Thr Arg Pro Pro Ser Ala Phe Ser Leu
305                 310                 315                 320
```

Asp Lys Met Ala Ala Ile Phe Tyr Ile Ile Leu Asn Pro Leu Leu Asn
            325                 330                 335

Pro Leu Ile Tyr Thr Phe Arg Asn Lys Glu Val Lys Gln Ala Met Arg
        340                 345                 350

Arg Ile Trp Asn Arg Leu Met Val Val Ser Asp Glu Lys Glu Asn Ile
        355                 360                 365

Lys Leu
    370

<210> SEQ ID NO 81
<211> LENGTH: 936
<212> TYPE: DNA
<213> ORGANISM: Mus Musculus

<400> SEQUENCE: 81

```
atgcaaaacc agagttttgt aacagaattc atattccttg actttcaca gaaccctaaa      60
gtccagaaaa tagtttttat tgtatttta tttgtctaca ttgcaactgt tgggggcaac     120
atgataattg tggtgaccat tgtctgtagc ccagcattga tagactgccc catgtacttc    180
tttttggcat tcttgtccct attggatgca tgcttctctt ctgtcatcac accaaagatg    240
gttgtggact ccctgtatga agaaaaact atctcctttg aaggatgtat gatgcagtta    300
tttgctgagc acttccttgc agcagtagaa gtgattgtct tgacagccat ggcctatgac    360
cgctatgtag caatttgcaa gcccttgcac tactcttcca tcatgaactg gaggctctgt    420
ggcacactta tggggatagc atggacaggg ggcttcttgc attctatcat acaaattatc    480
ttcacgttgc aattgcccct ctgtggacca atgtcatcg atcatttcat gtgtgacttg    540
ttcccattac tggaacttgc ctgcactgat actcatatct ttggcctttt agtggttgcc    600
aacagtgggt ctatctgcat cataatcttc tctattttgc tggtctccta tggtgtcatc    660
ctgttctctc tgaaagctca cagttctgaa gggcgatgga agctctctc cacatgtgga    720
tcccacattg cagttgtggt tttgttcttt gtcccgtgta tatttattta tgcacgtcct    780
ccatctgctt tctcctttga taaaatggtg gcgatatttt atactatcct aactcccttg    840
ctcaatcctg tgatttatac ttttcggaat aaggacatga aaaatgctat gaagaaagtg    900
tggaagaggt tggcagtggt ttctgatgga aagtga                              936
```

<210> SEQ ID NO 82
<211> LENGTH: 311
<212> TYPE: PRT
<213> ORGANISM: Mus Musculus

<400> SEQUENCE: 82

Met Gln Asn Gln Ser Phe Val Thr Glu Phe Ile Phe Leu Gly Leu Ser
1               5                   10                  15

Gln Asn Pro Lys Val Gln Lys Ile Val Phe Ile Val Phe Leu Phe Val
            20                  25                  30

Tyr Ile Ala Thr Val Gly Gly Asn Met Ile Ile Val Val Thr Ile Val
        35                  40                  45

Cys Ser Pro Ala Leu Ile Asp Cys Pro Met Tyr Phe Phe Leu Ala Phe
    50                  55                  60

Leu Ser Leu Leu Asp Ala Cys Phe Ser Ser Val Ile Thr Pro Lys Met
65                  70                  75                  80

Val Val Asp Ser Leu Tyr Glu Lys Thr Ile Ser Phe Glu Gly Cys
                85                  90                  95

```
Met Met Gln Leu Phe Ala Glu His Phe Leu Ala Ala Val Glu Val Ile
            100                 105                 110
Val Leu Thr Ala Met Ala Tyr Asp Arg Tyr Val Ala Ile Cys Lys Pro
        115                 120                 125
Leu His Tyr Ser Ser Ile Met Asn Trp Arg Leu Cys Gly Thr Leu Met
    130                 135                 140
Gly Ile Ala Trp Thr Gly Gly Phe Leu His Ser Ile Ile Gln Ile Ile
145                 150                 155                 160
Phe Thr Leu Gln Leu Pro Phe Cys Gly Pro Asn Val Ile Asp His Phe
                165                 170                 175
Met Cys Asp Leu Phe Pro Leu Leu Glu Leu Ala Cys Thr Asp Thr His
            180                 185                 190
Ile Phe Gly Leu Leu Val Val Ala Asn Ser Gly Ser Ile Cys Ile Ile
        195                 200                 205
Ile Phe Ser Ile Leu Leu Val Ser Tyr Gly Val Ile Leu Phe Ser Leu
    210                 215                 220
Lys Ala His Ser Ser Glu Gly Arg Trp Lys Ala Leu Ser Thr Cys Gly
225                 230                 235                 240
Ser His Ile Ala Val Val Leu Phe Phe Val Pro Cys Ile Phe Ile
                245                 250                 255
Tyr Ala Arg Pro Pro Ser Ala Phe Ser Phe Asp Lys Met Val Ala Ile
            260                 265                 270
Phe Tyr Thr Ile Leu Thr Pro Leu Leu Asn Pro Val Ile Tyr Thr Phe
        275                 280                 285
Arg Asn Lys Asp Met Lys Asn Ala Met Lys Lys Val Trp Lys Arg Leu
    290                 295                 300
Ala Val Val Ser Asp Gly Lys
305                 310

<210> SEQ ID NO 83
<211> LENGTH: 1080
<212> TYPE: DNA
<213> ORGANISM: Homo sapiens

<400> SEQUENCE: 83
atggccttgg ggaatcacag caccatcacc gagttcctcc tccttgggct gtctgccgac      60
cccaacatcc gggctctgct ctttgtgctg ttcctgggga tttacctcct gaccataatg     120
gaaaacctga tgctgctgct catgatcagg gctgattctt gtctccataa gcccatgtat     180
ttcttcctga gtcacctctc ttttgttgat ctctgcttct cttcagtcat tgtgcccaag     240
atgctggaga acctcctgtc acagaggaaa accatttcag tagagggctg cctggctcag     300
gtcttctttg tgtttgtcac tgcagggact gaagcctgcc ttctctcagg atggcctat      360 gaccgccatg ctgccatctg ccgcccacta ctttatggac agatcatggg taaacagctg     420
tatatgcacc ttgtgtgggg ctcatgggga ctgggctttc tggacgcact catcaatgtc     480
ctcctagctg taaacatggt cttttgtgaa gccaaaatca ttcaccacta cagctatgag     540
atgccatccc tcctccctct gtcctgctct gatatctcca gaagcctcat cgccttgctc     600
tgctccactc tcctacatgg gctgggaaac ttccttttgg tcttcttatc ctacacccgt     660
ataatctcta ccatcctaag catcagctct acctcgggca aagcaaggc cttctccacc     720 tgctctgccc acctcactgc agtgacactt tactatggct caggtttgct ccgccatctc     780
atgccaaact caggttcccc catagagttg atcttctctg tgcagtatac tgtagtcact     840
cccatgctga attccctcat ctatagcctg aaaaataagg aagtgaaggg ggaaagaagc     900
```

```
ctccgggaca gcagtcattt gcctcagctg cacaaaggcc aggccagatg gaagagacca    960
gccttcaccg aaggccgcag ggagcccgga cacccggagc tgagcattcc ggtcacgcct   1020
caaccccaag gggcctgcgc atgctccgcg ctgcgcgcgg cgcccacggc cctgccctga   1080
```

<210> SEQ ID NO 84
<211> LENGTH: 359
<212> TYPE: PRT
<213> ORGANISM: Homo sapiens

<400> SEQUENCE: 84

```
Met Ala Leu Gly Asn His Ser Thr Ile Thr Glu Phe Leu Leu Gly
1               5                   10                  15

Leu Ser Ala Asp Pro Asn Ile Arg Ala Leu Leu Phe Val Leu Phe Leu
                20                  25                  30

Gly Ile Tyr Leu Leu Thr Ile Met Glu Asn Leu Met Leu Leu Met
            35                  40                  45

Ile Arg Ala Asp Ser Cys Leu His Lys Pro Met Tyr Phe Phe Leu Ser
50                  55                  60

His Leu Ser Phe Val Asp Leu Cys Phe Ser Ser Val Ile Val Pro Lys
65                  70                  75                  80

Met Leu Glu Asn Leu Leu Ser Gln Arg Lys Thr Ile Ser Val Glu Gly
                85                  90                  95

Cys Leu Ala Gln Val Phe Phe Val Phe Val Thr Ala Gly Thr Glu Ala
            100                 105                 110

Cys Leu Leu Ser Gly Met Ala Tyr Asp Arg His Ala Ala Ile Cys Arg
        115                 120                 125

Pro Leu Leu Tyr Gly Gln Ile Met Gly Lys Gln Leu Tyr Met His Leu
    130                 135                 140

Val Trp Gly Ser Trp Leu Gly Phe Leu Asp Ala Leu Ile Asn Val
145                 150                 155                 160

Leu Leu Ala Val Asn Met Val Phe Cys Glu Ala Lys Ile Ile His His
                165                 170                 175

Tyr Ser Tyr Glu Met Pro Ser Leu Leu Pro Leu Ser Cys Ser Asp Ile
            180                 185                 190

Ser Arg Ser Leu Ile Ala Leu Leu Cys Ser Thr Leu His Gly Leu
        195                 200                 205

Gly Asn Phe Leu Leu Val Phe Leu Ser Tyr Thr Arg Ile Ile Ser Thr
    210                 215                 220

Ile Leu Ser Ile Ser Ser Thr Ser Gly Arg Ser Lys Ala Phe Ser Thr
225                 230                 235                 240

Cys Ser Ala His Leu Thr Ala Val Thr Leu Tyr Tyr Gly Ser Gly Leu
                245                 250                 255

Leu Arg His Leu Met Pro Asn Ser Gly Ser Pro Ile Glu Leu Ile Phe
            260                 265                 270

Ser Val Gln Tyr Thr Val Val Thr Pro Met Leu Asn Ser Leu Ile Tyr
        275                 280                 285

Ser Leu Lys Asn Lys Glu Val Lys Gly Glu Arg Ser Leu Arg Asp Ser
    290                 295                 300

Ser His Leu Pro Gln Leu His Lys Gly Gln Ala Arg Trp Lys Arg Pro
305                 310                 315                 320

Ala Phe Thr Glu Gly Arg Arg Glu Pro Gly His Pro Glu Leu Ser Ile
                325                 330                 335

Pro Val Thr Pro Gln Pro Gln Gly Ala Cys Ala Cys Ser Ala Leu Arg
```

Ala Ala Pro Thr Ala Leu Pro
                355

<210> SEQ ID NO 85
<211> LENGTH: 960
<212> TYPE: DNA
<213> ORGANISM: Mus Musculus

<400> SEQUENCE: 85
atgaggaact tcagtgttgc ctctgagttc atcctccttg gtctgtctga agatgcacag      60
gtccaggctc tactctttgt ggctttcctt gtgatctatg tcctgaccct gacagggaac     120
tccatgattc tgttggtgat aagggtggat gctcacctcc gctctcccat gtactttttt     180
ctgggtcacc tctccttcct ggatcttttg tattcatcag tctccacacc caagatgctg     240
gagaatctgg tgtctgagac aaaaaccatc cctgtgaagg gttgtctggc ccaggccttc     300
tttgtgtttg ccattggggg taccgaggct ttgcttcttg ctgtcatggc ctatgatcga     360
tatgcagcca tttgccaccc tctactctat ggtcagatga tgagtgactg gttctgccag     420
gtgctagtgt ggggatcctg gatcctggcc atcctgaact cactcattaa taccctccta     480
gctgtgagtt tggactttg tcactatgga accatacaca actacaactg tgagtttccc     540
tccctcttcc ctctctcctg ctccgatgtc tccactaatg ccactgccat agtctgtagt     600
tttgtcatac acgcctctgg aaccttcctt ctcgtggtag gttcttatgg ctgcattttc     660
tccactatcc tgaacatgag ctccaccagg ggtaggagca aggcattttc cacctgctcc     720
tcccacctca ccgtagtgat gttgtacttt ggttcggcct gcctgcgcta cgtcatgccc     780
acctcaggtt ctccagtgga aatgtacttc tctgtgcagt acagcgtcat cacccccatg     840
ctgaatccct ttatctacag tctgaagaac caggaggtga aggcggccat gagaaagctg     900
ctggcaagat gctaccagca ttttgggggat gttgatcaga gacacaggga caagtgttga     960

<210> SEQ ID NO 86
<211> LENGTH: 319
<212> TYPE: PRT
<213> ORGANISM: Mus Musculus

<400> SEQUENCE: 86

Met Arg Asn Phe Ser Val Ala Ser Glu Phe Ile Leu Leu Gly Leu Ser
1               5                   10                  15

Glu Asp Ala Gln Val Gln Ala Leu Leu Phe Val Ala Phe Leu Val Ile
            20                  25                  30

Tyr Val Leu Thr Leu Thr Gly Asn Ser Met Ile Leu Leu Val Ile Arg
        35                  40                  45

Val Asp Ala His Leu Arg Ser Pro Met Tyr Phe Phe Leu Gly His Leu
    50                  55                  60

Ser Phe Leu Asp Leu Leu Tyr Ser Ser Val Ser Thr Pro Lys Met Leu
65                  70                  75                  80

Glu Asn Leu Val Ser Glu Thr Lys Thr Ile Pro Val Lys Gly Cys Leu
                85                  90                  95

Ala Gln Ala Phe Phe Val Phe Ala Ile Gly Gly Thr Glu Ala Leu Leu
            100                 105                 110

Leu Ala Val Met Ala Tyr Asp Arg Tyr Ala Ala Ile Cys His Pro Leu
        115                 120                 125

Leu Tyr Gly Gln Met Met Ser Asp Trp Phe Cys Gln Val Leu Val Trp
    130                 135                 140

```
Gly Ser Trp Ile Leu Ala Ile Leu Asn Ser Leu Ile Asn Thr Leu Leu
145                 150                 155                 160

Ala Val Ser Leu Asp Phe Cys His Tyr Gly Thr Ile His Asn Tyr Asn
                165                 170                 175

Cys Glu Phe Pro Ser Leu Phe Pro Leu Ser Cys Ser Asp Val Ser Thr
                180             185                 190

Asn Ala Thr Ala Ile Val Cys Ser Phe Val Ile His Ala Ser Gly Thr
            195             200                 205

Phe Leu Leu Val Val Gly Ser Tyr Gly Cys Ile Phe Ser Thr Ile Leu
        210             215                 220

Asn Met Ser Ser Thr Arg Gly Arg Ser Lys Ala Phe Ser Thr Cys Ser
225                 230                 235                 240

Ser His Leu Thr Val Val Met Leu Tyr Phe Gly Ser Ala Cys Leu Arg
                245                 250                 255

Tyr Val Met Pro Thr Ser Gly Ser Pro Val Glu Met Tyr Phe Ser Val
                260             265                 270

Gln Tyr Ser Val Ile Thr Pro Met Leu Asn Pro Phe Ile Tyr Ser Leu
        275             280                 285

Lys Asn Gln Glu Val Lys Ala Ala Met Arg Lys Leu Leu Ala Arg Cys
        290             295                 300

Tyr Gln His Phe Gly Asp Val Asp Gln Arg His Arg Asp Lys Cys
305             310             315
```